US012648945B2

(12) United States Patent
Zhai et al.

(10) Patent No.: US 12,648,945 B2
(45) Date of Patent: Jun. 9, 2026

(54) COMPOSITIONS AND METHODS FOR TREATING SYSTEMIC LUPUS ERYTHEMATOSUS

(71) Applicants: ASCENTAGE PHARMA (SUZHOU) CO., LTD., Suzhou (CN); ASCENTAGE PHARMA GROUP CORP LIMITED, Central (CN)

(72) Inventors: Yifan Zhai, Suzhou (CN); Dajun Yang, Suzhou (CN); Dong Fang, Suzhou (CN); Saijie Zhu, Suzhou (CN)

(73) Assignees: ASCENTAGE PHARMA (SUZHOU) CO., LTD., Suzhou (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 462 days.

(21) Appl. No.: 18/042,252

(22) PCT Filed: Aug. 20, 2021

(86) PCT No.: PCT/CN2021/113832
§ 371 (c)(1),
(2) Date: Feb. 20, 2023

(87) PCT Pub. No.: WO2022/037684
PCT Pub. Date: Feb. 24, 2022

(65) Prior Publication Data

US 2023/0301989 A1 Sep. 28, 2023

(30) Foreign Application Priority Data

Aug. 21, 2020 (WO) ................ PCT/CN2020/110516

(51) Int. Cl.

| | |
|---|---|
| ***A61K 31/496*** | (2006.01) |
| ***A61K 31/444*** | (2006.01) |
| ***A61K 31/4545*** | (2006.01) |
| ***A61P 13/12*** | (2006.01) |
| ***A61P 37/06*** | (2006.01) |

(52) U.S. Cl.
CPC .......... *A61K 31/496* (2013.01); *A61K 31/444* (2013.01); *A61K 31/4545* (2013.01); *A61P 13/12* (2018.01); *A61P 37/06* (2018.01)

(58) Field of Classification Search
CPC .............. A61K 31/444; A61K 31/4545; A61K 31/496; C07D 471/04; A61P 9/00; A61P 13/12; A61P 17/00; A61P 29/00; A61P 37/00; A61P 37/02; A61P 37/06; A61P 43/00
See application file for complete search history.

(56) References Cited

U.S. PATENT DOCUMENTS

2012/0129853 A1* 5/2012 Elmore ..................... A61P 1/00
514/253.09

FOREIGN PATENT DOCUMENTS

| | | | |
|---|---|---|---|
| WO | WO2012071374 | A1 | 5/2012 |
| WO | WO2014158528 | A1 | 10/2014 |
| WO | WO2018027097 | A1 | 2/2018 |
| WO | WO2020024834 | A1 | 2/2020 |
| WO | WO2020024916 | A1 | 2/2020 |
| WO | WO2020103921 | A1 | 5/2020 |
| WO | WO2020228695 | A1 | 11/2020 |
| WO | WO2021000899 | A1 | 1/2021 |
| WO | WO2021110097 | A1 | 6/2021 |

OTHER PUBLICATIONS

Nader, A., et al. "Exposure-response analyses of the effects of venetoclax, a selective BCL-2 inhibitor, on B-lymphocyte and total lymphocyte counts in women with systemic lupus erythematosus." Clinical pharmacokinetics., vol. 59, No. 3, Sep. 21, 2019; pp. 335-347.

Minocha, M., et al. "Pharmacokinetics of the B-cell lymphoma 2 (Bcl-2) inhibitor venetoclax in female subjects with systemic lupus erythematosus." Clinical pharmacokinetics., vol. 57, No. 19, Jan. 15, 2018; pp. 1185-1198.

Nov. 19, 2021 PCT ISR & Written Opinion for PCT/CN2021/113832, 16 pages.

* cited by examiner

*Primary Examiner* — Sarah Pihonak
(74) *Attorney, Agent, or Firm* — Goodwin Procter LLP

(57) ABSTRACT

Methods for treating systemic lupus erythematosus using compounds or pharmaceutical compositions that modulate the activity of Bcl-2 family proteins are disclosed. In some methods, the patient to be treated is diagnosed with lupus nephritis. In some methods, the compound or pharmaceutical composition is administered to the patient in need thereof at a therapeutically effective dose sufficient to elicit one or more effects selected from: reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced vasculitis severity in the patient, reduced lymphocyte cell counts in a peripheral blood mononuclear cell (PMBC) panel taken from the patient, reduced lymphocyte cell counts in the spleen of the patient, and reduced lymphocyte infiltration of the kidneys of the patient.

17 Claims, 5 Drawing Sheets

| | % of reduction (v.s. Vehicle) |
|---|---|
| CD45+ cells | 71.0 |
| T cells | 88.2 |
| CD4+ T cells | 73.6 |
| CD8+ T cells | 75.6 |
| DN T cells | 94.9 |
| B cells | 87.2 |
| Activated B cells | 78.8 |
| Plasmablast | 91.3 |
| CD138+ cells | 89.7 |

| | % of reduction (v.s. Vehicle) |
|---|---|
| CD45+ cells | 93.9 |
| T cells | 95.3 |
| CD4+ T cells | 90.7 |
| CD8+ T cells | 94.9 |
| DN T cells | 98.1 |
| B cells | 95.2 |
| Activated B cells | 96.9 |
| Plasmablast | 98.1 |
| Plasma cells | 96.9 |
| CD138+ cells | 97.1 |

COMPOSITIONS AND METHODS FOR TREATING SYSTEMIC LUPUS ERYTHEMATOSUS

This application is a 35 U.S.C. § 371 United States National Phase Stage of, and claims priority to, PCT International Application No. PCT/CN2021/113832 filed Aug. 20, 2021, which in turn claims the priority of PCT/CN2020/110516 filed Aug. 21, 2020 under 35 U.S.C. § 119. The entire contents of the aforementioned applications are incorporated herein by reference.

TECHNICAL FIELD

The present disclosure relates to methods of treating systemic lupus erythematosus (SLE) using Bcl-2 inhibitor compounds or compositions comprising the same.

BACKGROUND

Apoptosis, the process of programmed cell death, is an essential biological process for tissue homeostasis. In mammals, it has been shown to regulate early embryonic development. Later in life, cell death is a default mechanism by which potentially dangerous cells, e.g., cells carrying cancerous defects, are removed. Several apoptotic pathways are known. One of the most important apoptotic pathways involves the Bcl-2 family of proteins which are key regulators of the mitochondrial (also called "intrinsic") pathway of apoptosis. See Danial and Korsmeyer, *Cell* 116:205-219 (2004). The structural homology domains BH1, BH2, BH3 and BH4 are characteristic of Bcl-2 family proteins. The Bcl-2 family of proteins can be further classified into three subfamilies depending on how many of the homology domains each protein contains and on its biological activity, i.e., whether it has pro- or anti-apoptotic function.

The first subgroup of Bcl-2 proteins contains proteins having all four homology domains, i.e., BH1, BH2, BH3 and BH4. Their general effect is anti-apoptotic, that is to preserve a cell from starting a cell death process. Proteins such as Bcl-2, Bcl-w, Bcl-xL, Mcl-1, and Bfl-l/Al are members of this first subgroup. Proteins belonging to the second subgroup of Bcl-2 proteins contain the three homology domains BH1, BH2, and BH3, and have a pro-apoptotic effect. The two main representative proteins of this second subgroup are Bax and Bak. The third subgroup of Bcl-2 proteins is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is not entirely known. In one hypothesis of regulation of cell death by Bcl-2 family proteins, the BH3-only proteins are further categorized as either "activator," e.g., Bim and Bid, or "sensitizer," e.g., Bad, Bik, Noxa, Hrk, Bmf, and Puma, proteins depending on their regulatory function.

One of the keys to tissue homeostasis is achieving a balance in the interactions among the three subgroups of Bcl-2 proteins in cells. Studies have elucidated the mechanisms by which pro-apoptotic and anti-apoptotic subgroups of Bcl-2 family proteins interact to allow a cell to undergo programmed cell death. After receiving intra- or extracellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins, e.g., Puma, Bim, Bid, are "activators" in that these proteins directly engage pro-apoptotic proteins Bax and Bak to initiate MOMP, while other BH3-only proteins, e.g., Bad, Bik and Noxa, are "sensitizers" and induce Bax and Bak oligomerization indirectly by binding anti-apoptotic proteins, e.g., Bcl-2, Bcl-xL, Bcl-w, Mcl-1, and displacing and "freeing-up" the "activator" BH3-only proteins, which subsequently bind to and activate pro-apoptotic proteins, e.g., Bax, Bak, to induce cell death. Other research suggests that anti-apoptotic proteins engage and sequester Bax and Bak directly and all BH3-only proteins regulates this interaction by binding to anti-apoptotic proteins, e.g., Bcl-2, Bcl-xL, Bcl-w, Mcl-1, which results in the release Bax and Bak. See Adams and Cory, *Oncogene* 26:1324-1337 (2007) and Willis et al., *Science* 315:856-859 (2007). Although the exact interactions through which the anti- and pro-apoptotic Bcl-2 family proteins regulate apoptosis remain under investigation, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In particular, Bcl-2 may be an attractive therapeutic target for the treatment of autoimmune disorders, including systemic lupus erythematosus (SLE). Dysregulated apoptosis in patients diagnosed with SLE, resulting from improper Bcl-2 function, for example, may lead to the survival of autoreactive immune cells that contribute to SLE-related complications, including lupus nephritis, which is the most common manifestation of advanced SLE. Some studies have shown that kidney-infiltrating B and T cells express aberrantly high levels of Bcl-2, compared to activated lymphocytes from healthy lymphoid tissues. See, for example, Ko et al., *Arthritis & Rheumatology* 68:2740-2751 (2016).

There is an ongoing need for small molecules that selectively inhibit the activity of one type or a subset of Bcl-2 proteins for the treatment of proliferative diseases such as autoimmune diseases, including systemic lupus erythematosus.

SUMMARY

Disclosed herein are methods of treating systemic lupus erythematosus in a patient comprising administering to the patient in need thereof a therapeutically effective amount of a compound of formula (I):

(I)

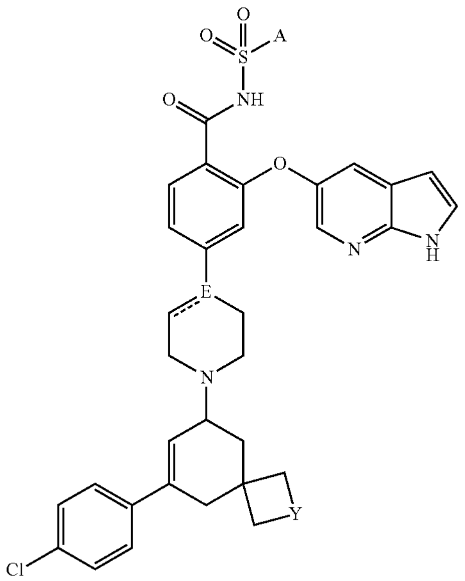

or a pharmaceutically acceptable salt, hydrate, solvate, stereoisomer, or tautomer thereof, wherein A, E, and Y are as defined herein.

Also disclosed herein are methods of treating systemic lupus erythematosus in a patient comprising administering to the patient in need thereof a therapeutically effective amount of a pharmaceutical composition comprising a compound of formula (I), as depicted above, or a pharmaceutically acceptable salt, hydrate, solvate, stereoisomer, or tautomer thereof.

In one embodiment, a method of treating systemic lupus erythematosus in a patient comprises administering to the patient in need thereof a therapeutically effective amount of a compound of formula (I):

(I)

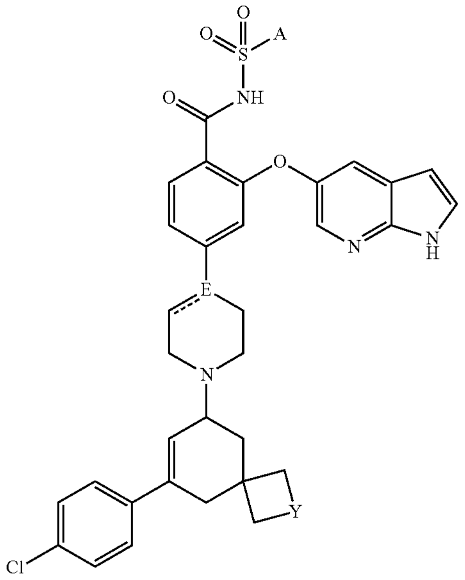

or a pharmaceutically acceptable salt, solvate, hydrate, stereoisomer, or tautomer thereof wherein:

A is selected from the group consisting of:

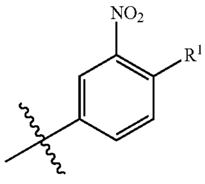

,

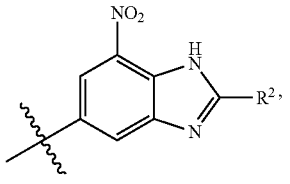

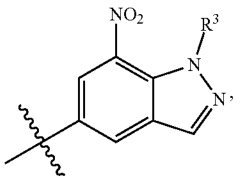

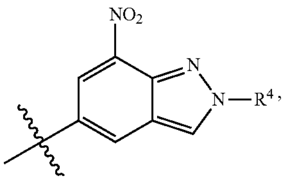

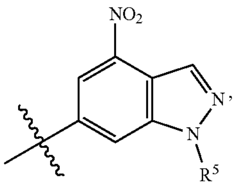

and

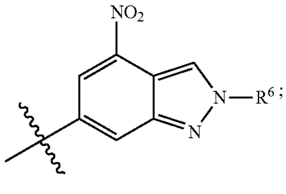

E is selected from the group consisting of:

a carbon atom, wherein $\overline{---}$ is a double bond;

—C(H)—, wherein $\overline{---}$ is a single bond; and a nitrogen atom, wherein $\overline{---}$ is a single bond;

Y is selected from —C(H)— and —O—;

$R^1$ is selected from hydrogen and —$N(R^{7a})(R^{7b})$;

$R^2$, $R^3$, $R^4$, $R^5$, and $R^6$ are each independently selected from the group consisting of hydrogen, optionally substituted $C_{1-6}$ alkyl, optionally substituted $C_{3-6}$ cycloalkyl, heterocyclo, optionally substituted heteroaryl, (heterocyclo)alkyl;

$R^{7a}$ is selected from optionally substituted $C_{1-6}$ alkyl and optionally substituted (heterocyclo)alkyl; and $R^{7b}$ is selected from hydrogen and $C_{1-4}$ alkyl.

In one embodiment, the method comprises administering to the patient in need thereof a therapeutically effective amount of a compound of formula (I) that is further given by formula (II):

(II)

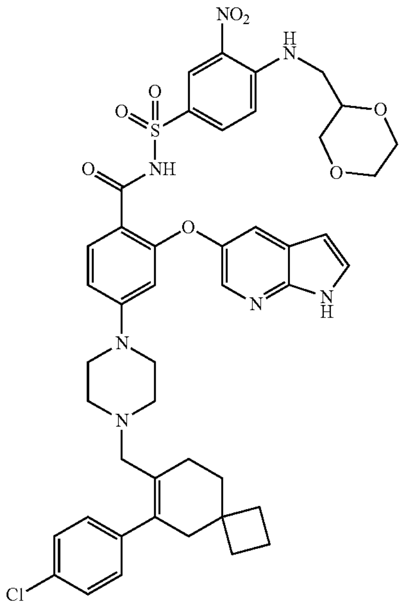

or a pharmaceutically acceptable salt, solvate, hydrate, stereoisomer, or tautomer thereof.

In one embodiment, the method comprises administering to the patient in need thereof a therapeutically effective amount of a compound selected from the group consisting of:

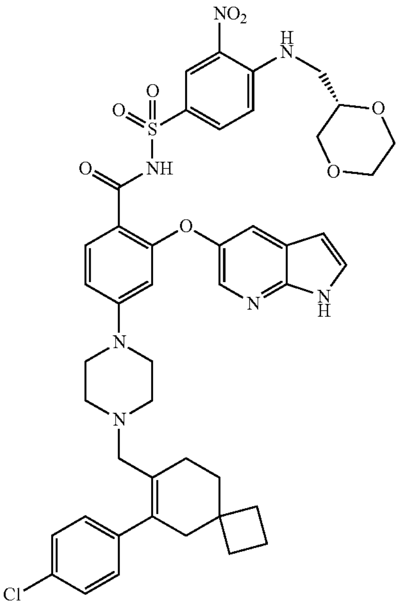

and

-continued

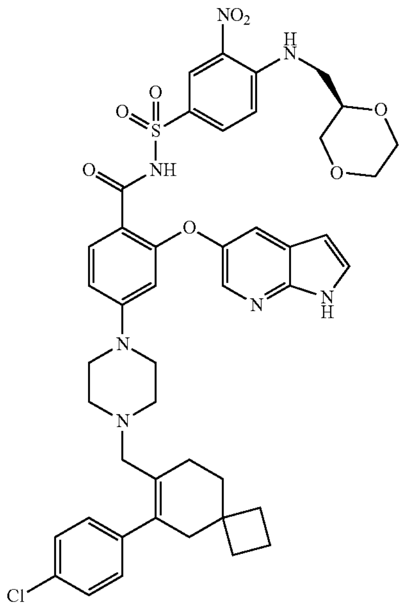

, or a pharmaceutically acceptable salt, solvate, hydrate, or tautomer thereof.

In one embodiment, the method comprises administering to the patient in need thereof a therapeutically effective amount of a compound, wherein the compound is:

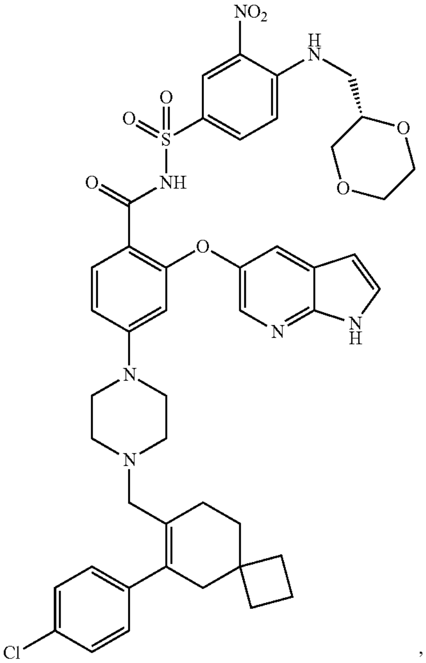 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

, or a pharmaceutically acceptable salt, solvate, hydrate, or tautomer thereof.

In one embodiment, the method comprises administering to the patient in need thereof a therapeutically effective amount of a compound, wherein the compound is:

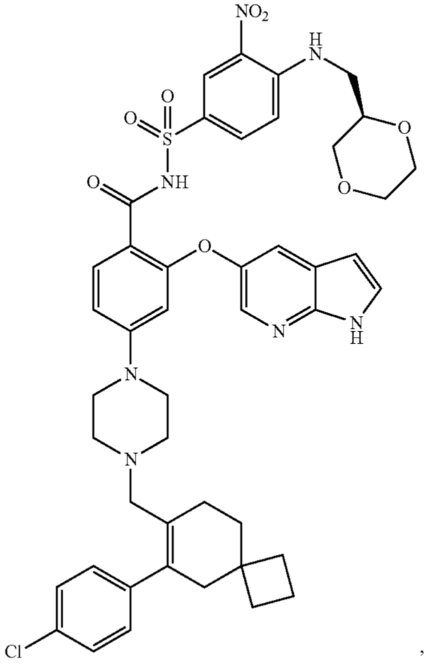 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]
, or a pharmaceutically acceptable salt, solvate, hydrate, or tautomer thereof.

In one embodiment, the method comprises administering to the patient in need thereof a therapeutically effective amount of a compound selected from a group consisting of the compounds recited in Table 1, as disclosed herein.

In one embodiment, a method of treating systemic lupus erythematosus in a patient comprises administering to the patient in need thereof a therapeutically effective amount of a pharmaceutical composition comprising a compound of formula (I):

(I)

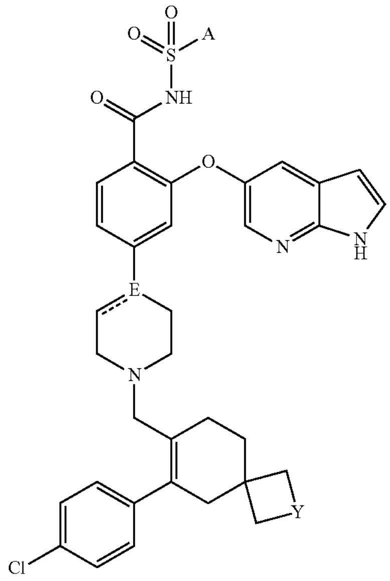

or a pharmaceutically acceptable salt, solvate, hydrate, stereoisomer, or tautomer thereof wherein:

A is selected from the group consisting of:

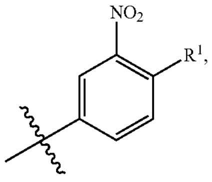
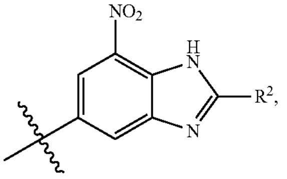
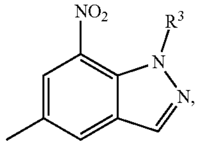
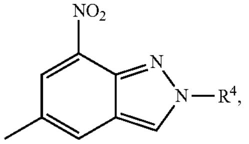
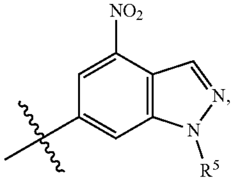
and
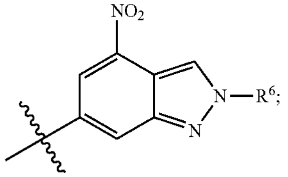

E is selected from the group consisting of:
- a carbon atom, wherein ⎓ is a double bond;
- —C(H)—, wherein ⎓ is a single bond; and
- a nitrogen atom, wherein ⎓ is a single bond;

Y is selected from —C(H)— and —O—;

$R^1$ is selected from hydrogen and —$N(R^{7a})(R^{7b})$;

$R^2$, $R^3$, $R^4$, $R^5$, and $R^6$ are each independently selected from the group consisting of hydrogen, optionally substituted $C_{1-6}$ alkyl, optionally substituted $C_{3-6}$ cycloalkyl, heterocyclo, optionally substituted heteroaryl, (heterocyclo)alkyl;

$R^{7a}$ is selected from optionally substituted $C_{1-6}$ alkyl and optionally substituted (heterocyclo)alkyl; and $R^{7b}$ is selected from hydrogen and $C_{1-4}$ alkyl.

In one embodiment, the method comprises administering to the patient in need thereof a therapeutically effective amount of a pharmaceutical composition comprising a compound of formula (I) that is further given by formula (II):

(II)

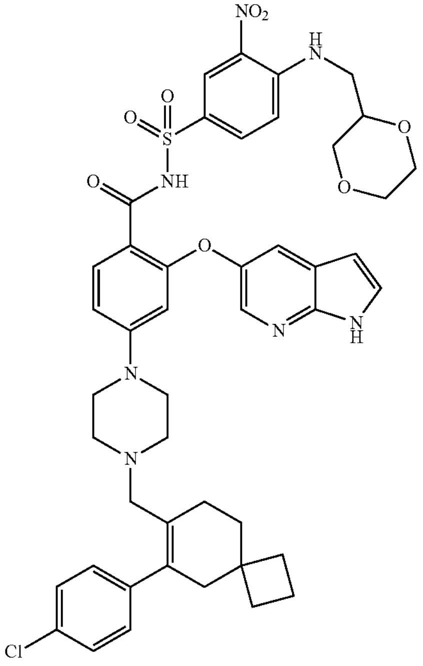

or a pharmaceutically acceptable salt, solvate, hydrate, stereoisomer, or tautomer thereof.

In one embodiment, the method comprises administering to the patient in need thereof a therapeutically effective amount of a pharmaceutical composition comprising a compound selected from:

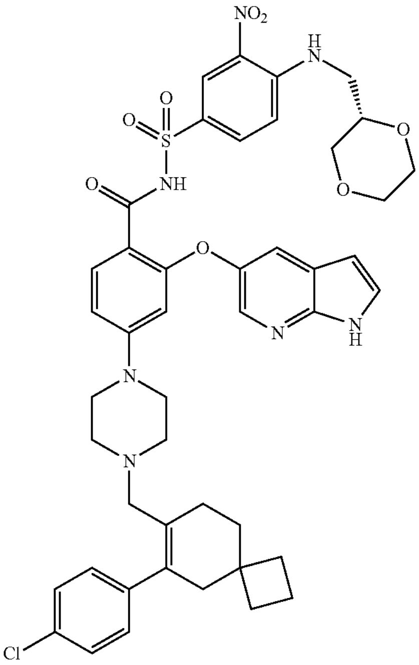 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

and

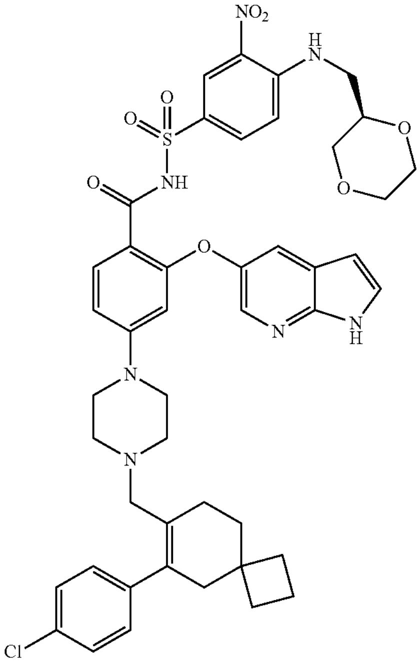 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

, or a pharmaceutically acceptable salt, solvate, hydrate, or tautomer thereof.

In one embodiment, the method comprises administering to the patient in need thereof a therapeutically effective amount of a pharmaceutical composition comprising

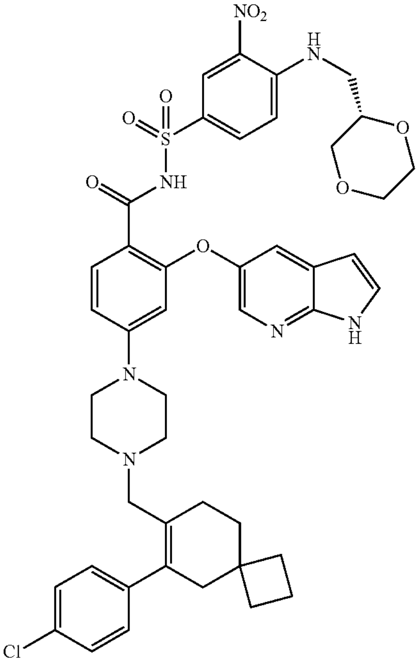 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, solvate, hydrate, or tautomer thereof.

In one embodiment, the method comprises administering to the patient in need thereof a therapeutically effective amount of a pharmaceutical composition comprising

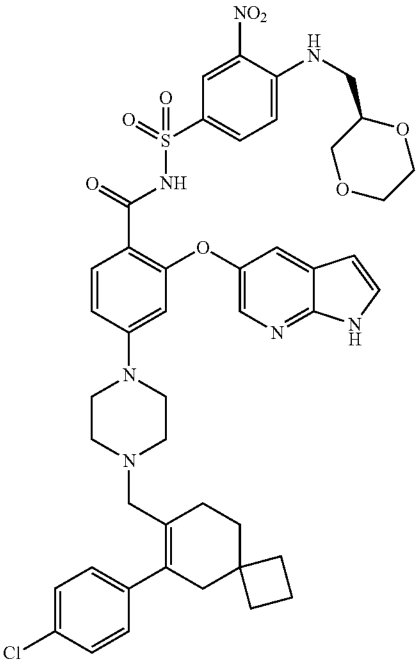

or a pharmaceutically acceptable salt, solvate, hydrate, or tautomer thereof.

In one embodiment, the method comprises administering to the patient in need thereof a therapeutically effective amount of a pharmaceutical composition comprising a compound selected from a group consisting of the compounds recited in Table 1, as described herein.

In one embodiment, a method of treating systemic lupus erythematosus in a patient comprises administering to the patient in need thereof a therapeutically effective amount of a compound, wherein the compound is (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl) benzamide.

In one embodiment, the patient in need thereof is diagnosed as having lupus nephritis.

In one embodiment, the compound or pharmaceutical composition is administered to the patient in need thereof at a dose sufficient to elicit one or more effects selected from the group consisting of: reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced vasculitis severity in the patient, reduced lymphocyte cell counts in a peripheral blood mononuclear cell (PBMC) panel taken from the patient, reduced lymphocyte cell counts in the spleen of the patient, and reduced lymphocyte infiltration of the kidneys of the patient.

In one embodiment, the compound or pharmaceutical composition is administered to the patient in need thereof at a dose sufficient to reduce excretion of protein in the urine of the patient.

In one embodiment, the compound or pharmaceutical composition is administered to the patient in need thereof at a dose sufficient to reduce serum anti-dsDNA autoantibody levels in the patient.

In one embodiment, the compound or pharmaceutical composition is administered to the patient in need thereof at a dose sufficient to reduce skin lesion severity in the patient.

In one embodiment, the compound or pharmaceutical composition is administered to the patient in need thereof at a dose sufficient to reduce severity of lymphadenopathy in the patient.

In one embodiment, the compound or pharmaceutical composition is administered to the patient in need thereof at a dose sufficient to reduce severity of glomerulonephritis in the patient.

In one embodiment, the compound or pharmaceutical composition is administered to the patient in need thereof at a dose sufficient to reduce severity of interstitial nephritis in the patient.

In one embodiment, the compound or pharmaceutical is administered to the patient in need thereof at a dose sufficient to reduce severity of vasculitis in the patient.

In one embodiment, the compound or pharmaceutical composition is administered to the patient in need thereof at a dose sufficient to reduce lymphocyte cell counts in a peripheral blood mononuclear cell (PBMC) panel taken from the patient.

In one embodiment, the compound or pharmaceutical composition is administered to the patient in need thereof at a dose sufficient to reduce lymphocyte cell counts in the spleen of the patient.

In one embodiment, the compound pharmaceutical composition is administered to the patient in need thereof at a dose sufficient to reduce lymphocyte infiltration in the kidneys of the patient.

In one embodiment, a compound of formula (I):

(I)

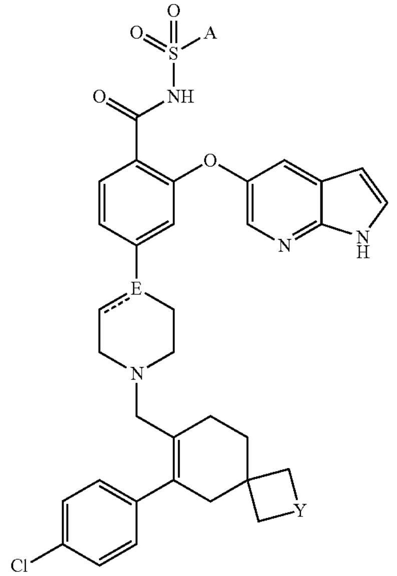

or a pharmaceutically acceptable salt, solvate, hydrate, stereoisomer or tautomer thereof, is used in the manufacture of a medicament for treating systemic lupus erythematosus in a patient in need thereof, wherein:

A is selected from the group consisting of:

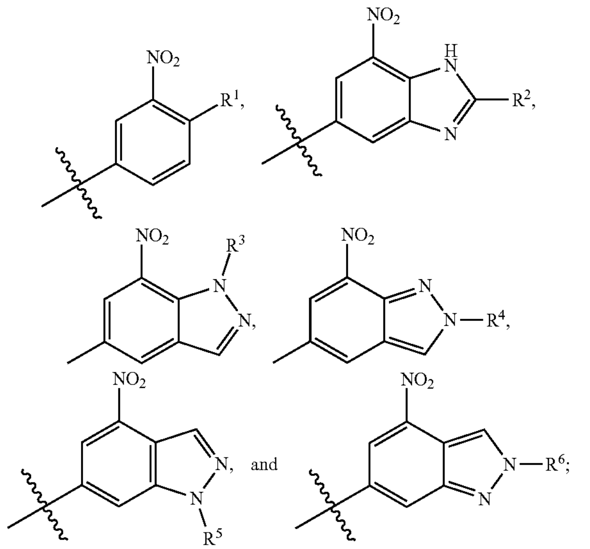

E is selected from the group consisting of:
- a carbon atom, wherein ⎓ is a double bond;
- —C(H)—, wherein ⎓ is a single bond; and
- a nitrogen atom, wherein ⎓ is a single bond;

Y is selected from —C(H)— and —O—;

$R^1$ is selected from hydrogen and —N($R^{7a}$)($R^{7b}$);

$R^2$, $R^3$, $R^4$, $R^5$, and $R^6$ are each independently selected from the group consisting of hydrogen, optionally substituted $C_{1-6}$ alkyl, optionally substituted $C_{3-6}$ cycloalkyl, heterocyclo, optionally substituted heteroaryl, (heterocyclo)alkyl;

$R^{7a}$ is selected from optionally substituted $C_{1-6}$ alkyl and optionally substituted (heterocyclo)alkyl; and $R^{7b}$ is selected from hydrogen and $C_{1-4}$ alkyl.

In one embodiment, the compound for use in the manufacture of the medicament is a compound of formula (I) that is further given by formula (II):

(II)

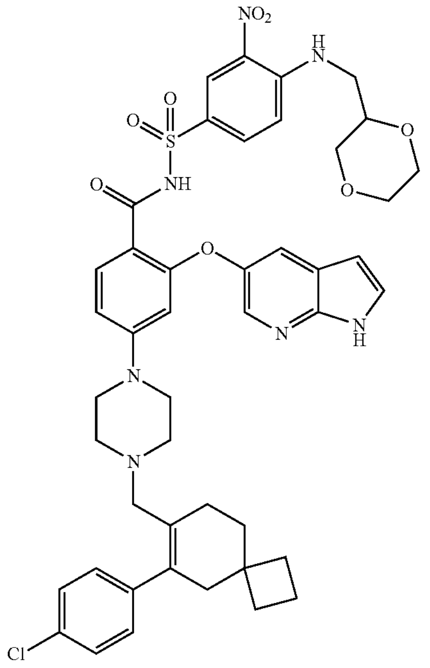

or a pharmaceutically acceptable salt, solvate, hydrate, stereoisomer, or tautomer thereof.

In one embodiment, the compound for use in the manufacture of the medicament is selected from the group consisting of:

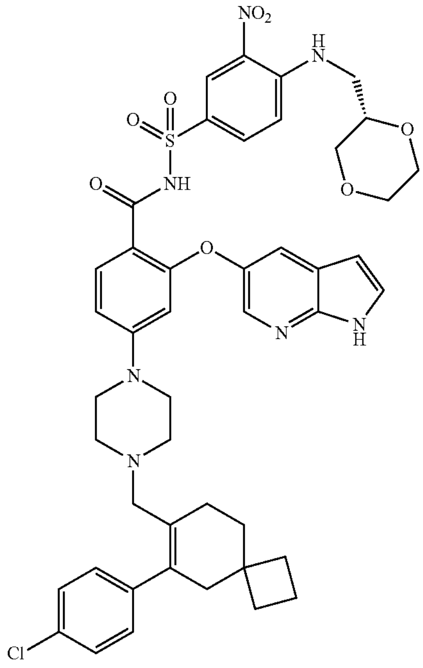

and

-continued

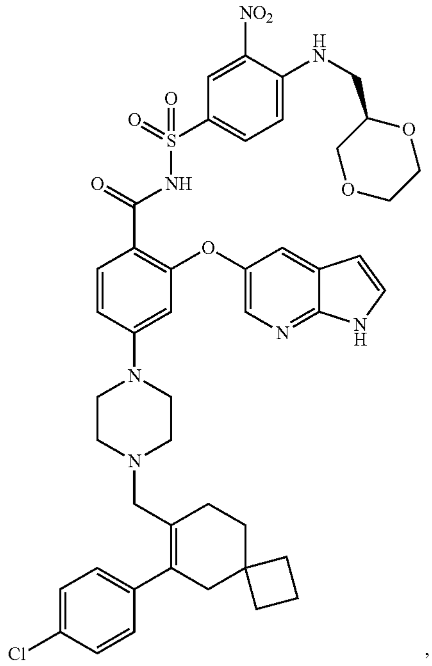

, or a pharmaceutically acceptable salt, solvate, hydrate, or tautomer thereof.

In one embodiment, the compound for use in the manufacture of the medicament is:

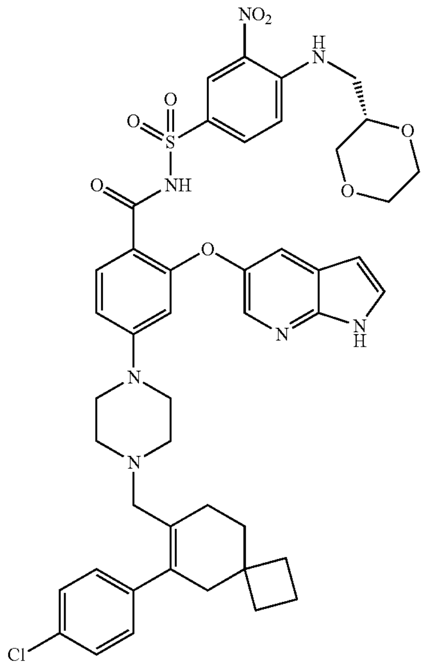

or a pharmaceutically acceptable salt, solvate, hydrate, or tautomer thereof.

In one embodiment, the compound for use in the manufacture of the medicament is:

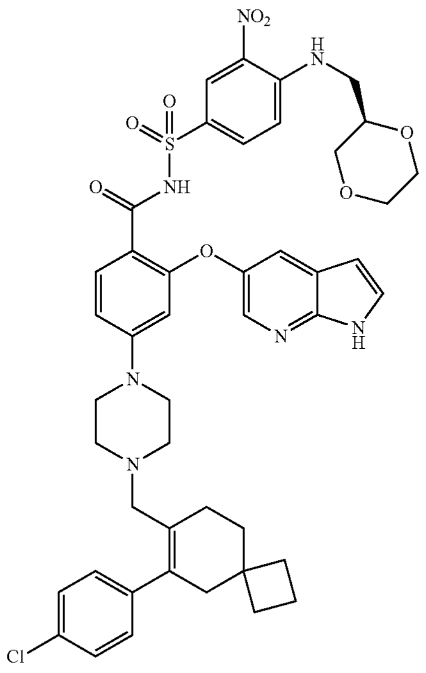 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, solvate, hydrate, or tautomer thereof.

In one embodiment, the compound for use in the manufacture of the medicament is selected from a group of compounds consisting of the compounds recited in Table 1, as described herein.

In one embodiment, (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide is used in the manufacture of a medicament for treating systemic lupus erythematosus in a patient in need thereof.

In one embodiment, the medicament is for treating systemic lupus erythematosus in a patient diagnosed as having lupus nephritis.

In one embodiment, the compound or pharmaceutical composition is used for the manufacture of a medicament for treating systemic lupus erythematosus, wherein the compound or pharmaceutical composition is administered to the patient in need thereof at a dose sufficient to elicit one or more effects selected from the group consisting of: reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced vasculitis severity in the patient, reduced lymphocyte cell counts in a peripheral blood mononuclear cell (PBMC) panel taken from the patient, reduced lymphocyte cell counts in the spleen of the patient, and reduced lymphocyte infiltration of the kidneys of the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce excretion of protein in the urine of the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce serum anti-dsDNA autoantibody levels in the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce skin lesion severity in the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce severity of lymphadenopathy in the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce severity of glomerulonephritis in the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce severity of intertitial nephritis in the patient.

In one embodiment, the compound or pharmaceutical composition is used for the manufacture of a medicament for treating systemic lupus erythematosus, wherein the compound or pharmaceutical is administered to the patient in need thereof at a dose sufficient to reduce severity of vasculitis in the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce lymphocyte cell counts in a peripheral blood mononuclear cell (PBMC) panel taken from the patient.

In one embodiment, the compound or pharmaceutical composition is used for the manufacture of a medicament for treating systemic lupus erythematosus, wherein the compound or pharmaceutical composition is administered to the patient in need thereof at a dose sufficient to reduce lymphocyte cell counts in the spleen of the patient.

In one embodiment, the compound or pharmaceutical composition is used for the manufacture of a medicament for treating systemic lupus erythematosus, wherein the compound pharmaceutical composition is administered to the patient in need thereof at a dose sufficient to reduce lymphocyte infiltration in the kidneys of the patient.

In one embodiment, a compound for use in the treatment of systemic lupus erythematosus in a patient in need thereof comprises a compound of formula (I):

(I)

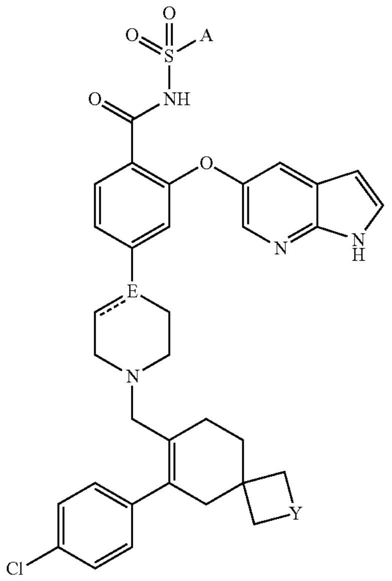

or a pharmaceutically acceptable salt, solvate, hydrate, stereoisomer, or tautomer thereof, wherein:

A is selected from the group consisting of:

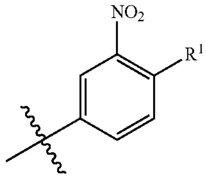
,
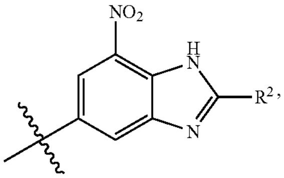
,
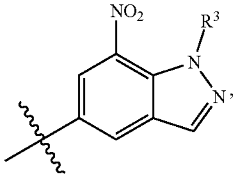
,
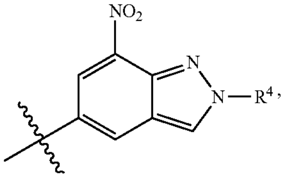
,
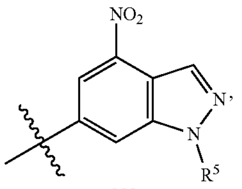
and
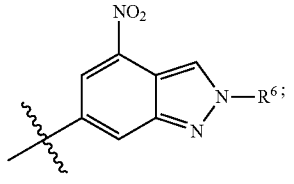
;

E is selected from the group consisting of:
- a carbon atom, wherein ⎓ is a double bond;
- —C(H)—, wherein ⎓ is a single bond; and
- a nitrogen atom, wherein ⎓ is a single bond;

Y is selected from —C(H)— and —O—;

$R^1$ is selected from hydrogen and —$N(R^{7a})(R^{7b})$;

$R^2$, $R^3$, $R^4$, $R^5$, and $R^6$ are each independently selected from the group consisting of hydrogen, optionally substituted $C_{1-6}$ alkyl, optionally substituted $C_{3-6}$ cycloalkyl, heterocyclo, optionally substituted heteroaryl, (heterocyclo)alkyl;

$R^{7a}$ is selected from optionally substituted $C_{1-6}$ alkyl and optionally substituted (heterocyclo)alkyl; and $R^{7b}$ is selected from hydrogen and $C_{1-4}$ alkyl.

In one embodiment, the compound for use in in the treatment of systemic lupus erythematosus in a patient in need thereof comprises a compound of formula (I) that is further given by formula (II):

(II)

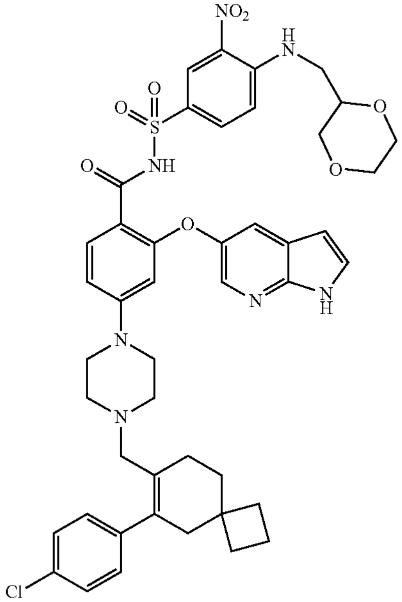

or a pharmaceutically acceptable salt, hydrate, solvate, stereoisomer, or tautomer thereof.

In one embodiment, the compound for use in in the treatment of systemic lupus erythematosus in a patient in need thereof comprises a compound selected from:

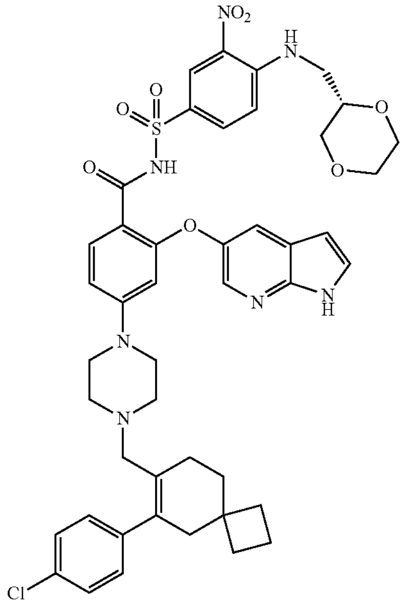 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]
and

-continued

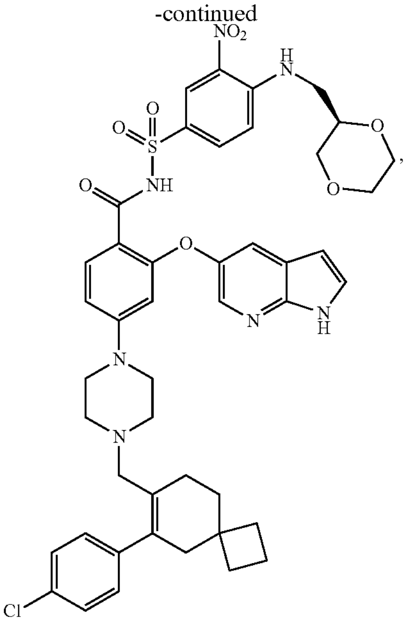

or a pharmaceutically acceptable salt, solvate, hydrate, or tautomer thereof.

In one embodiment, the compound for use in in the treatment of systemic lupus erythematosus in a patient in need thereof comprises:

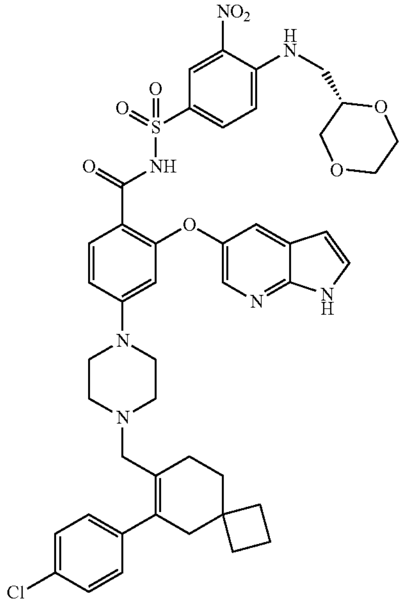

or a pharmaceutically acceptable salt, hydrate, solvate, or tautomer thereof.

In one embodiment, the compound for use in in the treatment of systemic lupus erythematosus in a patient in need thereof comprises:

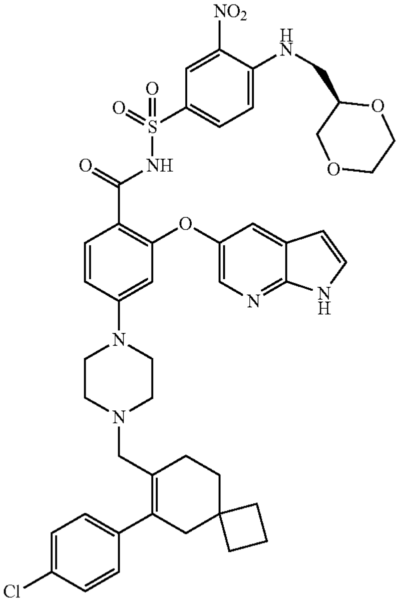 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, hydrate, solvate, or tautomer thereof.

In one embodiment, the compound for use in in the treatment of systemic lupus erythematosus in a patient in need thereof comprises a compound selected from a group consisting of the compounds recited in Table 1, as described herein.

In one embodiment, a compound for use in the treatment of systemic lupus erythematosus in a patient in need thereof comprises (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide.

In one embodiment, the compound is for use in the treatment of systemic lupus erythematosus in a patient, wherein the patient is diagnosed as having lupus nephritis.

In one embodiment, the compound is for use in the treatment of systemic lupus erythematosus in a patient, wherein the compound or pharmaceutical composition is administered to the patient in need thereof at a dose sufficient to elicit one or more effects selected from the group consisting of: reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced vasculitis severity in the patient, reduced lymphocyte cell counts in a peripheral blood mononuclear cell (PBMC) panel taken from the patient, reduced lymphocyte cell counts in the spleen of the patient, and reduced lymphocyte infiltration of the kidneys of the patient.

In one embodiment, the compound is for use in the treatment of systemic lupus erythematosus in a patient, wherein the compound or pharmaceutical composition is administered to the patient in need thereof at a dose sufficient to reduce excretion of protein in the urine of the patient.

In one embodiment, the compound is for use in the treatment of systemic lupus erythematosus in a patient, wherein the compound or pharmaceutical composition is administered to the patient in need thereof at a dose sufficient to reduce serum anti-dsDNA autoantibody levels in the patient.

In one embodiment, the compound is for use in the treatment of systemic lupus erythematosus in a patient, wherein the compound or pharmaceutical composition is administered to the patient in need thereof at a dose sufficient to reduce skin lesion severity in the patient.

In one embodiment, the compound is for use in the treatment of systemic lupus erythematosus in a patient, wherein the compound or pharmaceutical composition is administered to the patient in need thereof at a dose sufficient to reduce severity of lymphadenopathy in the patient.

In one embodiment, the compound is for use in the treatment of systemic lupus erythematosus in a patient, wherein the compound or pharmaceutical composition is administered to the patient in need thereof at a dose sufficient to reduce severity of glomerulonephritis in the patient.

In one embodiment, the compound is for use in the treatment of systemic lupus erythematosus in a patient, wherein the compound or pharmaceutical composition is administered to the patient in need thereof at a dose sufficient to reduce severity of interstitial nephritis in the patient.

In one embodiment, the compound is for use in the treatment of systemic lupus erythematosus in a patient, wherein the compound or pharmaceutical is administered to the patient in need thereof at a dose sufficient to reduce severity of vasculitis in the patient.

In one embodiment, the compound is for use in the treatment of systemic lupus erythematosus in a patient, wherein the compound or pharmaceutical composition is administered to the patient in need thereof at a dose sufficient to reduce lymphocyte cell counts in a peripheral blood mononuclear cell (PBMC) panel taken from the patient.

In one embodiment, the compound is for use in the treatment of systemic lupus erythematosus in a patient, wherein the compound or pharmaceutical composition is administered to the patient in need thereof at a dose sufficient to reduce lymphocyte cell counts in the spleen of the patient.

In one embodiment, the compound is for use in the treatment of systemic lupus erythematosus in a patient, wherein the compound pharmaceutical composition is administered to the patient in need thereof at a dose sufficient to reduce lymphocyte infiltration in the kidneys of the patient.

DETAILED DESCRIPTION

Figure 1:
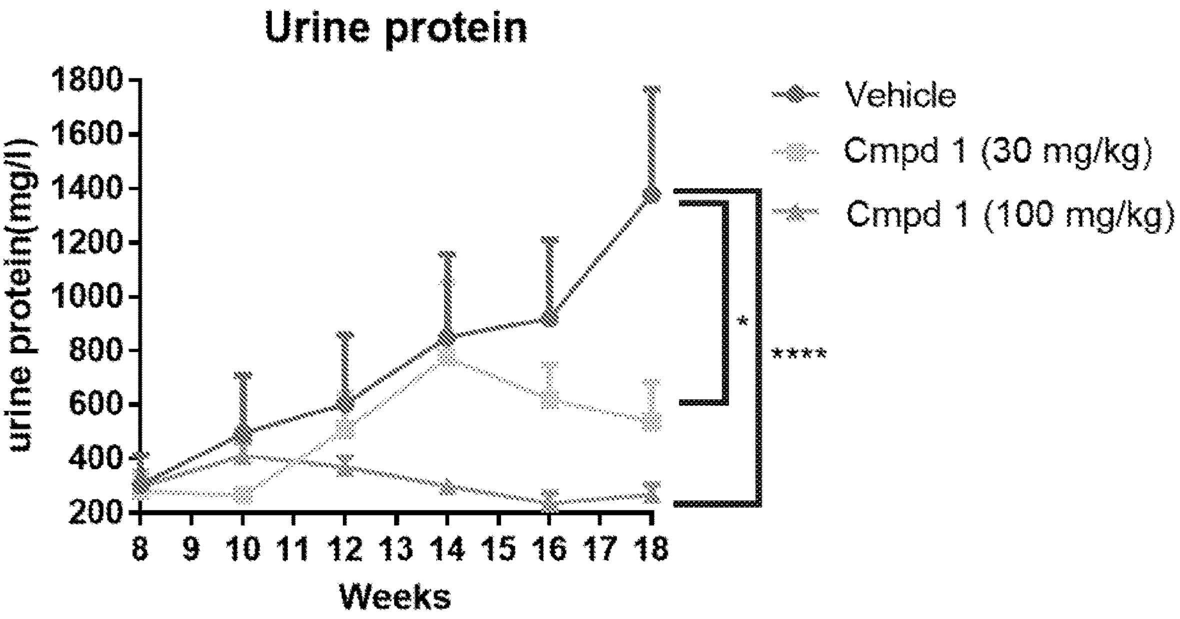
FIG. 1 is a line chart showing the concentration of protein in the urine of MRL/lpr mice over time following treatment with vehicle or Compound 1.

The present disclosure relates to compounds, or pharmaceutically acceptable salt, solvates, hydrates, tautomers, and stereoisomers thereof, capable of modulated Bcl-2 family proteins. Compounds capable of modulating Bcl-2 family proteins are useful in treating, preventing, or ameliorating diseases and disorders associated with the activity of Bcl-2 family proteins.

In some aspects, the disclosure features methods of treating or ameliorating systemic lupus erythematosus (SLE) in a patient by administering to the patient in need thereof a therapeutically effective amount of a compound capable of modulating Bcl-2 family proteins, or a pharmaceutical composition comprising a compound capable of modulating Bcl-2 family proteins.

Definitions

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. In another embodiment, the alkyl group is a branched chain $C_{3-4}$ alkyl group. In another embodiment, the alkyl group is a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-12}$ alkyl groups include methyl, $—CD_3$, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tertbutyl, and iso-butyl. Non-limiting exemplary $C_{1-4}$ groups include methyl, ethyl, propyl, isopropyl, and tert-butyl.

In the present disclosure, the term "optionally substituted alkyl" as used by itself or as part of another group refers to an alkyl that is unsubstituted or substituted with one, two, or three substituents independently selected from the group consisting of halo, nitre, cyano, hydroxy, alkoxy, amino, alkylamino, dialkylamino, and optionally substituted aryl. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary optionally substituted alkyl groups include $—CH_2Ph$, $—CH_2CH_2NO_2$, $—CH_2CH_2OH$, $—CH_2CH_2OCH_3$, and $—CH_2CH_2F$.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is a $C_{3-8}$ cycloalkyl. In another embodiment, the cycloalkyl group is a $C_{3-6}$ cycloalkyl. In another embodiment, the cycloalkyl group is a $C_{3-5}$ cycloalkyl. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclopentanone, spiro[3.3]heptane, and bicyclo[3.3.1]nonane.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl attached to a terminal oxygen atom. In one embodiment, the alkoxy group is a $C_{1-6}$ alkyl attached to a terminal oxygen atom. In another embodiment, the alkoxy group is a $C_{1-4}$ alkyl attached to a terminal oxygen atom. Nonlimiting exemplary alkoxy groups include methoxy, ethoxy, and tert-butoxy.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. The term "heterocyclo" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. In one embodiment, the heterocyclo group is a 4-, 5-, 6-, 7- or 8-membered cyclic group containing one ring and one or two oxygen and/or nitrogen atoms. In one embodiment, the heterocyclo group is a 5- or 6-membered cyclic group containing one ring and one or two nitrogen atoms. In one embodiment, the heterocyclo group is an 8-, 9-, 10-, 11-, or 12-membered cyclic group containing two rings and one or two nitrogen atoms. In one embodiment, the heterocyclo group is a 4- or 5-membered cyclic group containing one ring and one oxygen atom. The heterocyclo can be optionally linked to the rest of the molecule through a carbon or nitrogen atom. Non-limiting exemplary heterocyclo groups include 1,4-dioxane, 2-oxopyrrolidin-3-yl, 2-imidazolidinone, piperidinyl, morpholinyl, piperazinyl, pyrrolidinyl, 8-azabicyclo[3.2.1]octane (nortropane), 6-azaspiro[2.5]octane, 6-azaspiro[3.4]octane, indolinyl, indolinyl-2-one, and 1,3-dihydro-2H-benzo[d]imidazol-2-one.

In the present disclosure, the term "optionally substituted heterocyclo" as used herein by itself or part of another group refers to a heterocyclo that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo.

In the present disclosure, the term "(heterocyclo)alkyl" as used by itself or as part of another group refers to an alkyl substituted with one optionally substituted heterocyclo group. In one embodiment, the (heterocyclo)alkyl is a $C_{1-4}$ alkyl substituted with one optionally substituted 4- to 6-membered heterocyclo group. The heterocyclo can be linked to the alkyl group through a carbon or nitrogen atom. Non-limiting exemplary (heterocyclo)alkyl groups include:

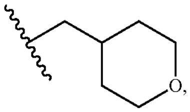,
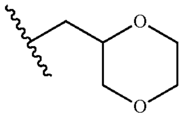,
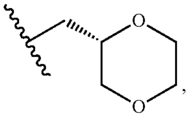,
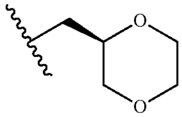,
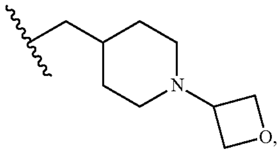,
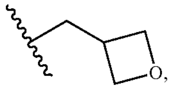,
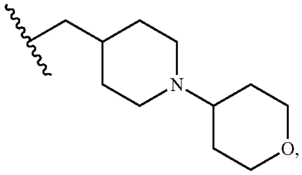,
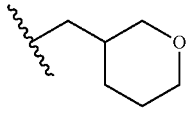,
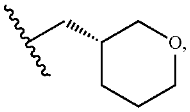,
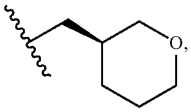,
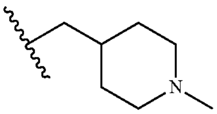
and
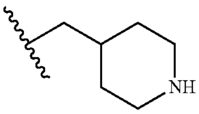.

As used herein, the term "heteroaryl" refers to a monocyclic aromatic radical of 5 to 14 ring atoms, containing one or more ring heteroatoms selected from the group consisting of N, O, and S, the remaining ring atoms being C. Examples include, but are not limited to, furyl, thienyl, pyrrolyl, pyridinyl, pyrazolyl, pyrimidinyl, imidazolyl, isoxazolyl, oxazolyl, oxadiazolyl, pyrazinyl, thiophen-2-yl, isothiazolyl, thiazolyl, thiadiazolyl, triazolyl, triazinyl.

As used herein, the term "optionally substituted heteroaryl" refers to a heteroaryl that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo.

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "about," as used herein, includes the recited number ±10%. Thus, "about 10" means 9 to 11.

As used herein, the term "isomer" refers to compounds that have the same composition and molecular weight but differ in physical and/or chemical properties. The structural difference may be in constitution (e.g., geometric isomers) or in the ability to rotate a plane of polarized light (stereoisomers). With regard to stereoisomers, the compounds of the disclosure may have one or more asymmetric carbon atoms and may occur as racemates, racemic mixtures or as individual enantiomers or diastereomers.

As used herein, the term "stereoisomers" or "stereoisomeric forms" are general terms for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense. In one embodiment, Compounds of the Disclosure having one or more chiral centers are enantiopure.

The terms "enantiomerically enriched" or "enantioenriched" refer to a sample of a chiral substance whose enantiomeric excess is greater than 50%, e.g., about 60% or more, about 70% or more, about 80% or more, about 90% or more, about 95% or more, about 98% or more, or about 99% or more. Enantiomerically enriched compounds may be enantiomerically pure.

The term "pharmaceutically acceptable salt" as used herein, refers to any salt, e.g., obtained by reaction with an acid or a base, of a compound of the disclosure that is physiologically tolerated in the target patient (e.g., a mammal, e.g., a human).

The use of the terms "salt" and the like, is intended to equally apply to the salt of enantiomers, stereoisomers, rotamers, tautomers, positional isomers, and racemates of the inventive compounds.

The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

A "patient" or "subject" is a mammal, e.g., a human, mouse, rat, guinea pig, dog, cat, horse, cow, pig, or non-human primate, such as a monkey, chimpanzee, baboon, or rhesus.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a compound of the disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

The term "administer", "administering", or "administration" as used in this disclosure refers to either directly administering a disclosed compound, a pharmaceutically acceptable salt of a disclosed compound or a composition to a subject, a pharmaceutically acceptable salt of a compound, or a composition to a subject, which can form an equivalent amount of active compound within the subject's body.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a proliferative disorder, e.g. an autoimmune disorder, the therapeutically effective amount of the agent may reduce (i.e., retard to some extent and preferably stop) unwanted cellular proliferation.

The term "carrier", as used in this disclosure, encompasses carriers, excipients, and diluents and means a material, composition or vehicle, such as a liquid or solid filler, diluent, excipient, solvent, or encapsulating material, involved in carrying or transporting a pharmaceutical agent from one organ, or portion of the body, to another organ, or portion of the body of a subject.

In the present disclosure, the term "Bcl-2 proteins" or "Bcl-2 family of proteins" refers to any one or more of the following proteins: Bax, Bak, Bid, Bcl-2, Bcl-xL, Mcl-1, Bcl-w, Bfl-l/Al, Bim, Puma, Bad, Bik/Blk, Noxa, Bmf, Hrk/DP5, and Beclin-1. See *Cold Spring Harb Perspect Biol* 2013; 5:a008714.

The term "disease" or "condition" or "disorder" denotes disturbances and/or anomalies that as a rule are regarded as being pathological conditions or functions, and that can manifest themselves in the form of particular signs, symptoms, and/or malfunctions. Compounds of the disclosure inhibit Bcl-2 proteins, such as Bcl-2 and/or Bcl-xL, and can be used in treating or preventing diseases, conditions, or disorders such as hyperproliferative diseases, wherein inhibition of Bcl-2 proteins provides a benefit.

The term "proliferative disease" refers to any condition in which a localized population of proliferating cells in an animal is not governed by the usual limitations of normal growth. In one embodiment, the proliferative disease is an autoimmune disorder, e.g. systemic lupus erythematosus.

In some embodiments, the compounds of the disclosure can be used to treat a "Bcl-2 protein mediated disorder," e.g., a Bcl-2-mediated disorder and/or a Bcl-xL-mediated disorder. A Bcl-2 protein mediated disorder is any pathological condition in which a Bcl-2 protein is known to play a role. In one embodiment, a Bcl-2 mediated disorder is a proliferative disease. In one embodiment, a Bcl-2 mediated disorder is systemic lupus erythematosus.

Compounds of the Disclosure

In one aspect, the disclosure relates to compounds of formula (I):

(I)

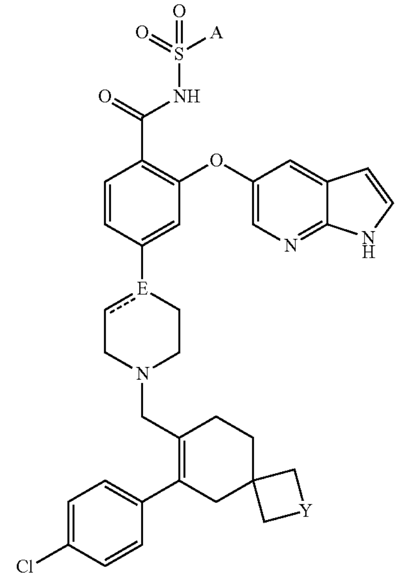

or pharmaceutically acceptable salts, hydrates, solvates, stereoisomers, or tautomers thereof, wherein:

A is selected from the group consisting of:

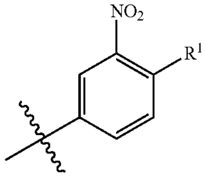
,
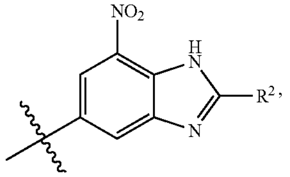

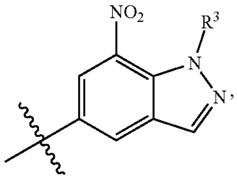

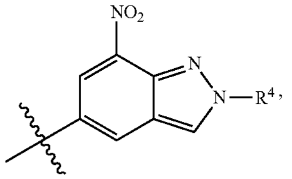

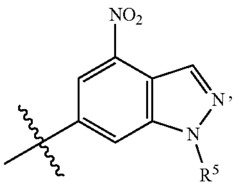
and

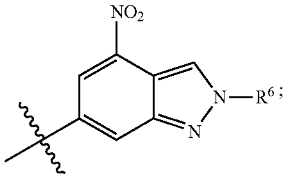

E is selected from the group consisting of:

a carbon atom, wherein ⎓ is a double bond;

—C(H)—, wherein ⎓ is a single bond; and a nitrogen atom, wherein ⎓ is a single bond;

Y is selected from —C(H)— and —O—;

$R^1$ is selected from hydrogen and —$N(R^{7a})(R^{7b})$;

$R^2$, $R^3$, $R^4$, $R^5$, and $R^6$ are each independently selected from the group consisting of hydrogen, optionally substituted $C_{1-6}$ alkyl, optionally substituted $C_{3-6}$ cycloalkyl, heterocyclo, optionally substituted heteroaryl, (heterocyclo)alkyl;

$R^{7a}$ is selected from optionally substituted $C_{1-6}$ alkyl and optionally substituted (heterocyclo)alkyl; and $R^{7b}$ is selected from hydrogen and $C_{1-4}$ alkyl.

In some embodiments, A is

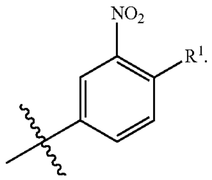

In some embodiments, A is

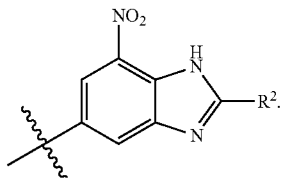

In some embodiments, A is

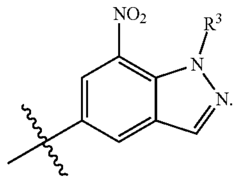

In some embodiments, A is

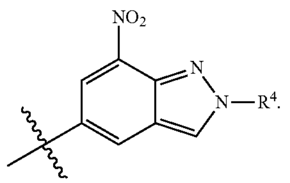

In some embodiments, A is

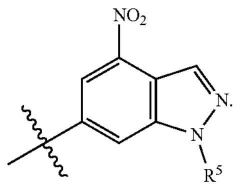

In some embodiments, A is

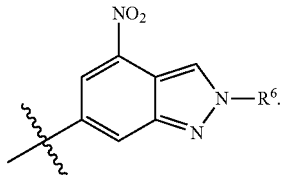

In some embodiments, E is a carbon atom, wherein $\overline{- - -}$ is a double bond. In some embodiments, E is —C(H)—, wherein $\overline{- - -}$ is a single bond. In some embodiments, E is a nitrogen atom, wherein $\overline{- - -}$ is a single bond.

In some embodiments, $R^1$ is hydrogen. In some embodiments, $R^1$ is —N($R^{7a}$)($R^{7b}$).

In some embodiments, $R^2$ is an optionally substituted $C_{1-6}$ alkyl. In some embodiments, $R^2$ is an optionally substituted $C_{1-4}$ alkyl. In some embodiments, $R^2$ is an optionally substituted $C_3$ alkyl. In some embodiments, $R^2$ is isopropyl. In some embodiments, $R^2$ is an optionally substituted $C_{3-6}$ cycloalkyl. In some embodiments, $R^2$ is an optionally substituted $C_{3-5}$ cycloalkyl. In some embodiments, $R^2$ is cyclopropyl. In some embodiments, $R^2$ is an optionally substituted heteroaryl. In some embodiments, $R^2$ is pyridinyl.

In some embodiments, $R^3$ is a (heterocyclo)alkyl. In some embodiments, $R^3$ is

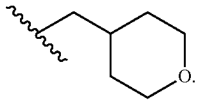 [SMILES: *CC1CCOCC1]

In some embodiments, $R^4$ is a (heterocyclo)alkyl. In some embodiments, $R^4$ is

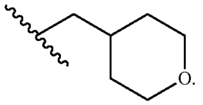

In some embodiments, $R^5$ is a (heterocyclo)alkyl. In some embodiments, $R^5$ is

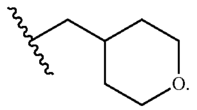 [SMILES: *CC1CCOCC1]

In some embodiments, $R^5$ is a heterocyclo. In some embodiments, $R^5$ is tetrahydro-2H-pyranyl.

In some embodiments, $R^6$ is a (heterocyclo)alkyl. In some embodiments, $R^6$ is

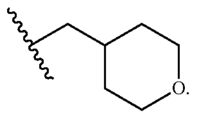 [SMILES: *CC1CCOCC1]

In some embodiments, $R^6$ is a heterocyclo. In some embodiments, $R^6$ is tetrahydro-2H-pyranyl.

In some embodiments, $R^{7a}$ is an optionally substituted $C_{1-6}$ alkyl. In some embodiments, $R^{7a}$ is an optionally substituted $C_{1-4}$ alkyl. In some embodiments, $R^{7a}$ is an optionally substituted methyl. In some embodiments, $R^{7a}$ is methyl. In some embodiments, $R^{7a}$ is an optionally substituted (heterocyclo)alkyl. In some embodiments, $R^{7a}$ is

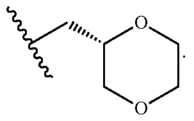 [SMILES: *C[C@H]1COCCO1]

In some embodiments, $R^{7a}$ is

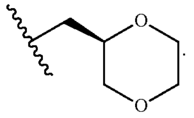 [SMILES: *C[C@@H]1COCCO1]

In some embodiments, $R^{7a}$ is

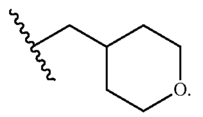 [SMILES: *CC1CCOCC1]

In some embodiments, $R^{7b}$ is hydrogen. In some embodiments, $R^{7b}$ is $C_{1-4}$ alkyl. In some embodiments, $R^{7b}$ is $C_{1-3}$ alkyl. In some embodiments, $R^{7b}$ is methyl.

In some embodiments, the disclosure relates to a compound of formula (I), selected from Table 1, or a pharmaceutically acceptable salt, hydrate, solvate, stereoisomer, or tautomer thereof.

TABLE 1

| Cpd. No. | Structure | Name |
|---|---|---|
| 1 | 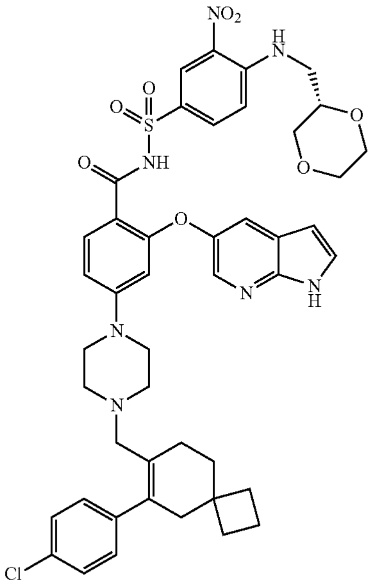 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 2 | 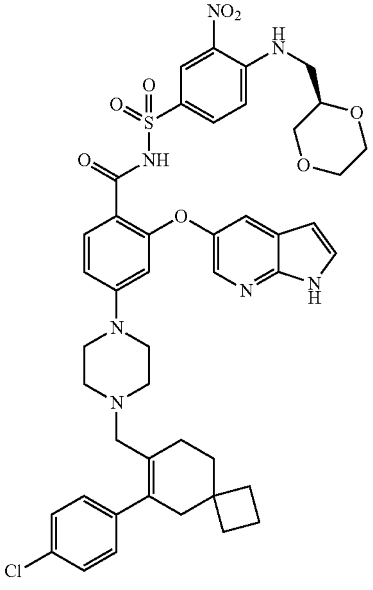 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued
| Cpd. No. | Structure | Name |
|---|---|---|
| 3 | 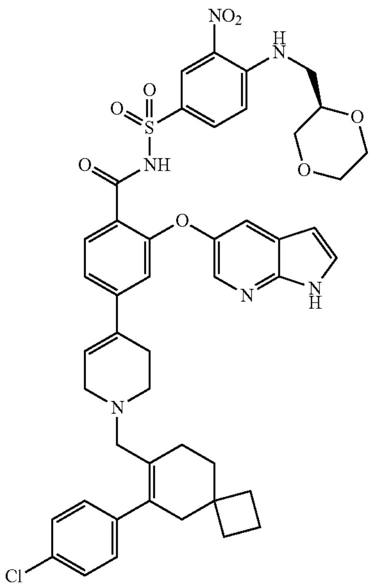 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 4 | 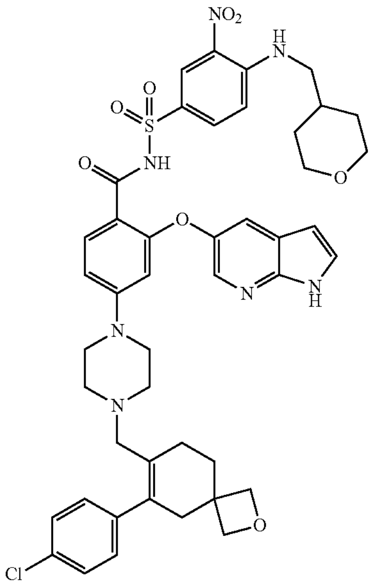 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued
| Cpd. No. | Structure | Name |
| --- | --- | --- |
| 5 | 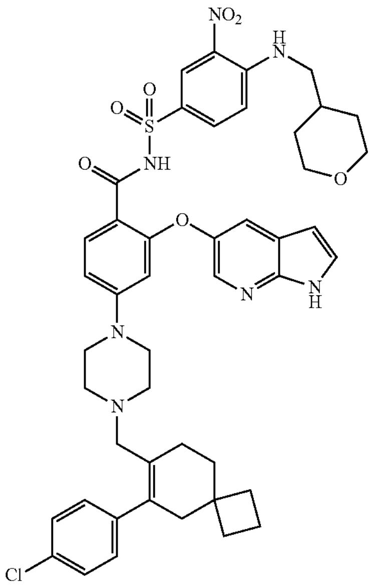 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 6 | 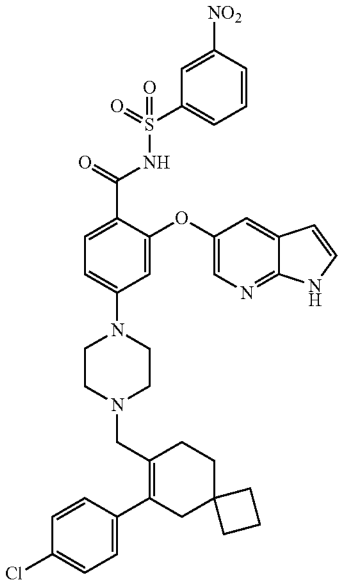 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |

TABLE 1-continued
| Cpd. No. | Structure | Name |
|---|---|---|
| 7 | 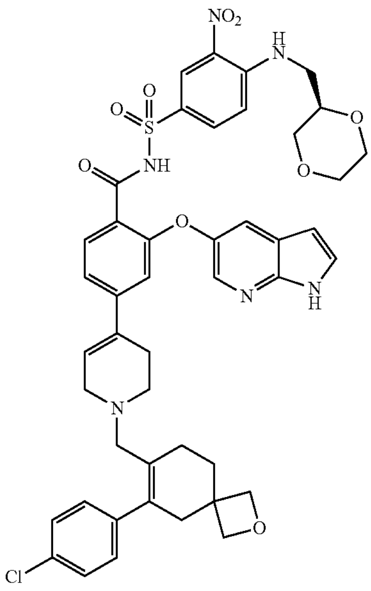 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 8 | 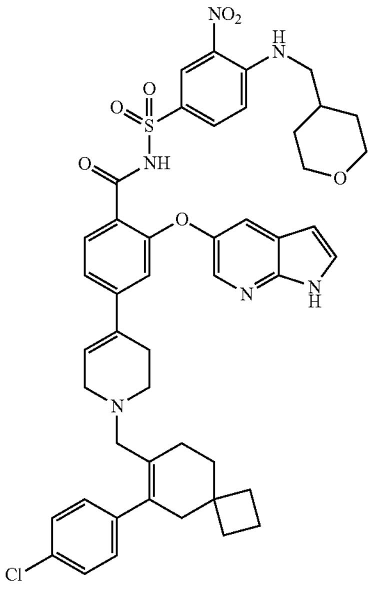 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 9 | 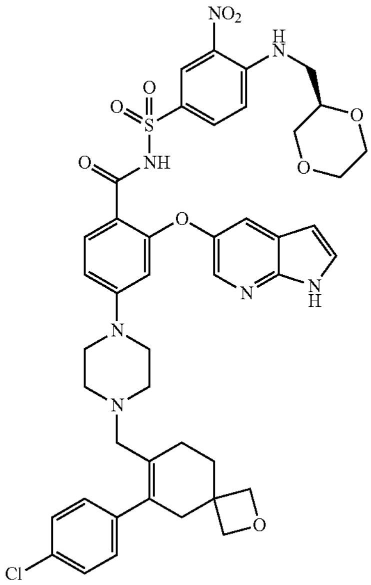 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |
| 10 | 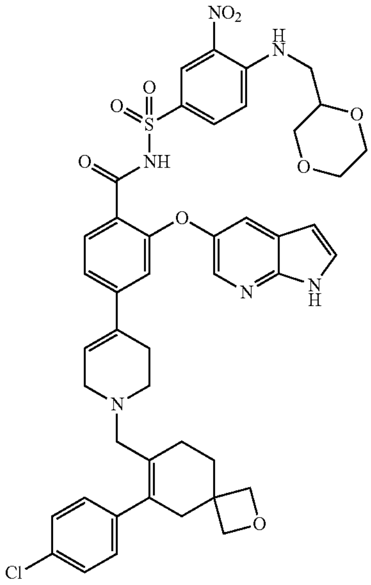 [SMILES: O=C(NS(=O)(=O)c1ccc(NCC2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 11 | 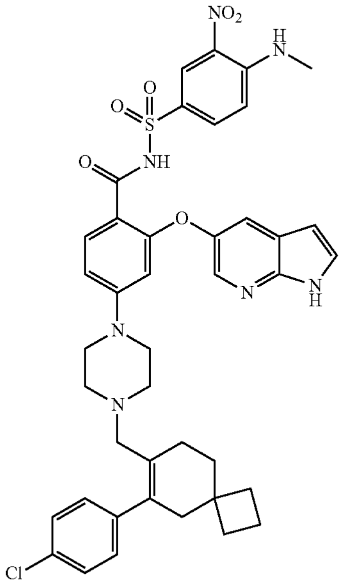 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |
| 12 | 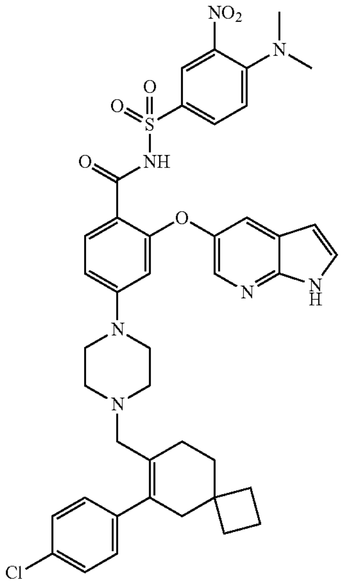 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |

TABLE 1-continued
| Cpd. No. | Structure | Name |
|---|---|---|
| 13 | 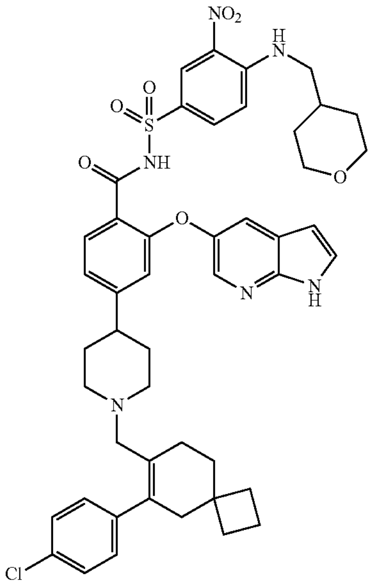 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |
| 14 | 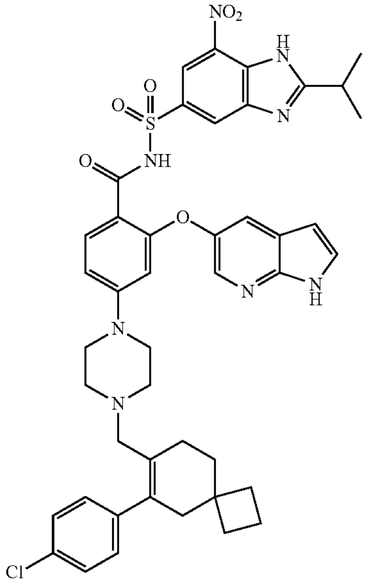 [SMILES: CC(C)c1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2[nH]1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-isopropyl-7-nitro-1H-benzo[d]imidazol-5-yl)sulfonyl)benzamide |

TABLE 1-continued
| Cpd. No. | Structure | Name |
| --- | --- | --- |
| 15 | 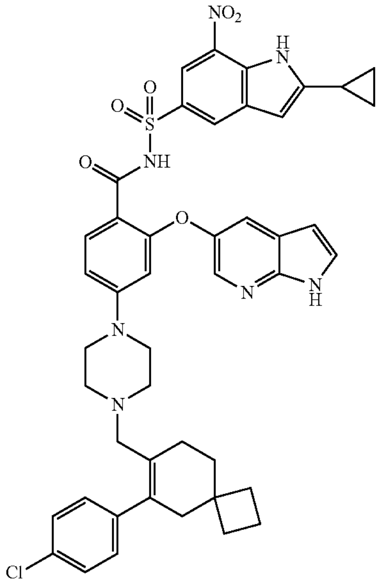 [SMILES: O=C(NS(=O)(=O)c1cc([N+](=O)[O-])c2[nH]c(C3CC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-cyclopropyl-7-nitro-1H-benzo[d]imidazol-5-yl)sulfonyl)benzamide |
| 16 | 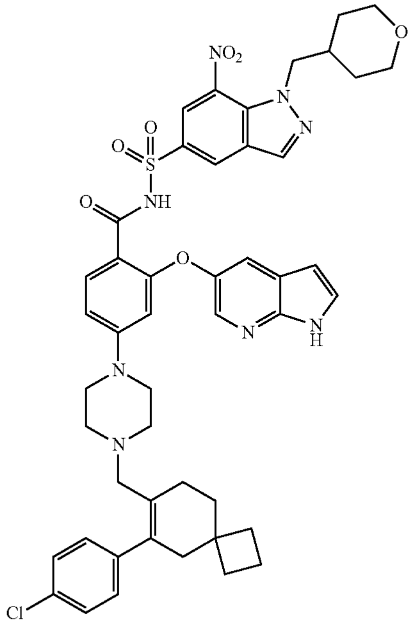 [SMILES: O=C(NS(=O)(=O)c1cc([N+](=O)[O-])c2c(cnn2CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1-((tetrahydro-2H-pyran-4-yl)methyl)-1H-indazol-5-yl)sulfonyl)benzamide |

TABLE 1-continued
| Cpd. No. | Structure | Name |
|---|---|---|
| 17 | 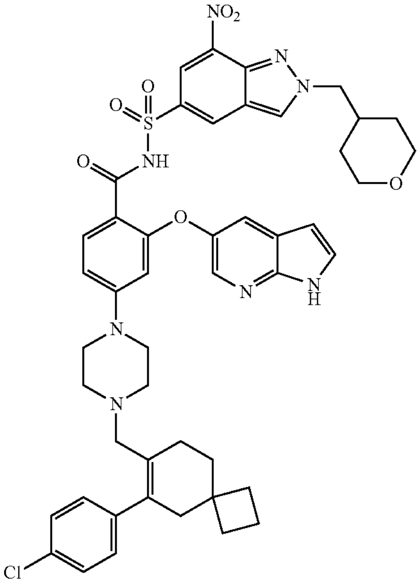 [SMILES: O=C(NS(=O)(=O)c1cc([N+](=O)[O-])c2nn(CC3CCOCC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-2H-indazol-5-yl)sulfonyl)benzamide |
| 18 | 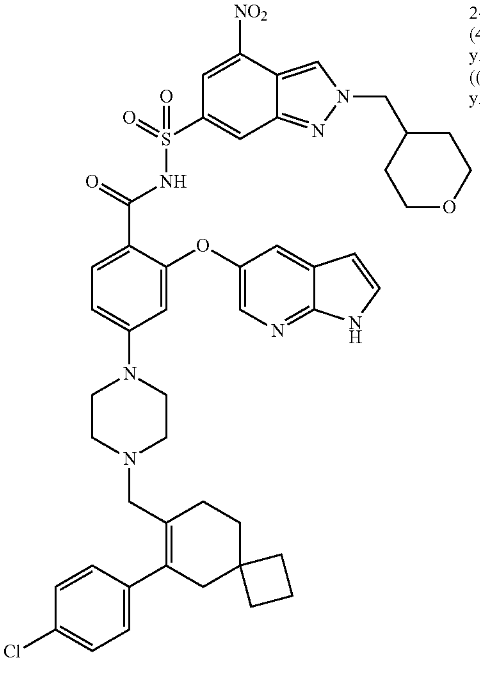 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-((tetrahydro-2H-pyran-4-yl)methyl)-2H-indazol-6-yl)sulfonyl)benzamide |

TABLE 1-continued

| Cpd. No. | Structure | Name |
| --- | --- | --- |
| 19 | 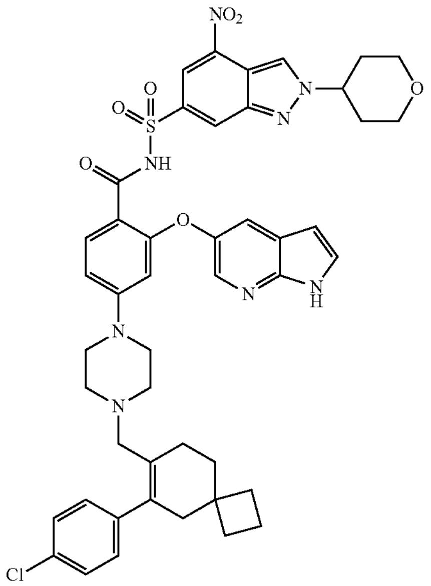 [SMILES: O=C(NS(=O)(=O)c1cc([N+](=O)[O-])c2cn(C3CCOCC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-(tetrahydro-2H-pyran-4-yl)-2H-indazol-6-yl)sulfonyl)benzamide |
| 20 | 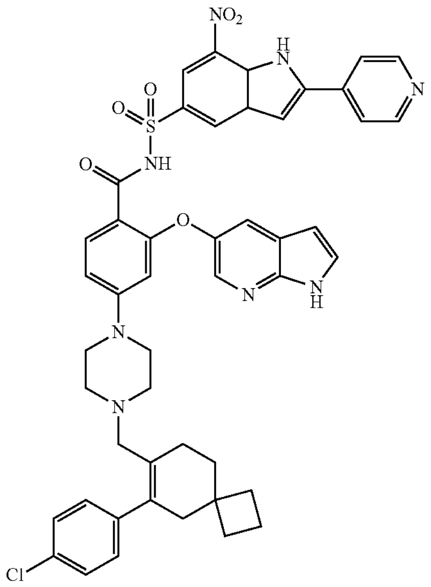 [SMILES: O=C(NS(=O)(=O)C1=CC2C=C(c3ccncc3)NC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(pyridin-4-yl)-1H-benzo[d]imidazol-5-yl)sulfonyl)benzamide |

Compounds of formula (I) may contain one or more asymmetric centers and may thus give rise to enantiomers, diastereomers, and other stereoisomeric forms. The present disclosure is meant to encompass the use of all such possible forms including racemic and resolved forms, and mixtures thereof. The individual stereoisomers, e.g., enantiomers, can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also intended to be encompassed by the present disclosure. The assay results may reflect the data collected for the racemic form, the enantiomerically pure form, or any other form in terms of stereochemistry. Individual stereoisomers of the compounds of the disclosure may be, for example, substantially free of other isomers, or may be admixed, for example, as racemates or with all other, or other selected, stereoisomers.

In some embodiments, compounds of formula (I) having one or more chiral centers are enantioenriched.

In addition, the present disclosure embraces all geometric and positional isomers. For example, if a compound of formulas (I) incorporates a double bond or a fused ring, both the cis- and trans-forms, as well as mixtures, are embraced within the scope of the disclosure. If the compound contains a double bond, the substituent may be in the E or Z configuration, unless otherwise indicated. If the compound contains a disubstituted cycloalkyl, the cycloalkyl substituent may have a cis- or trans configuration, unless otherwise indicated.

In some embodiments, the disclosure relates to compounds of formula (I) that are further given by formula (II):

(II)

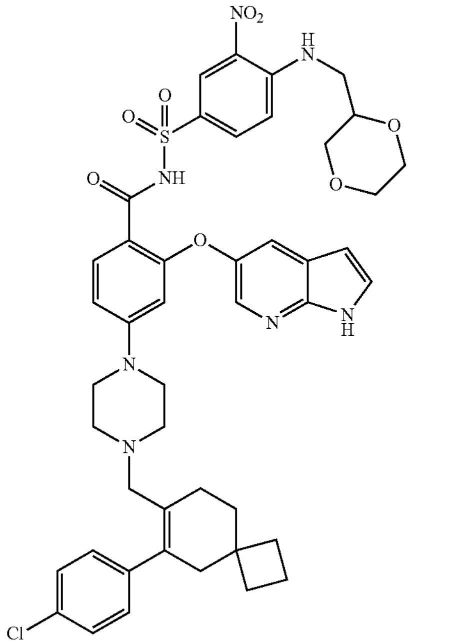

or pharmaceutically acceptable salts, hydrates, solvates, stereoisomers, or tautomers thereof.

In some embodiments, the disclosure relates to a compound of formula (II) selected from the group consisting of Compound (1) and Compound (2):

(1)

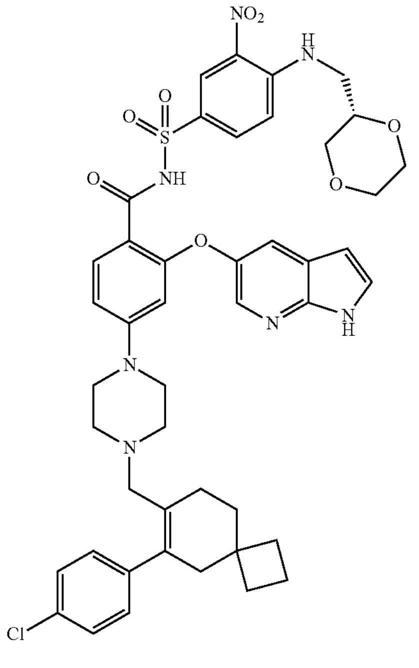

and

-continued (2)

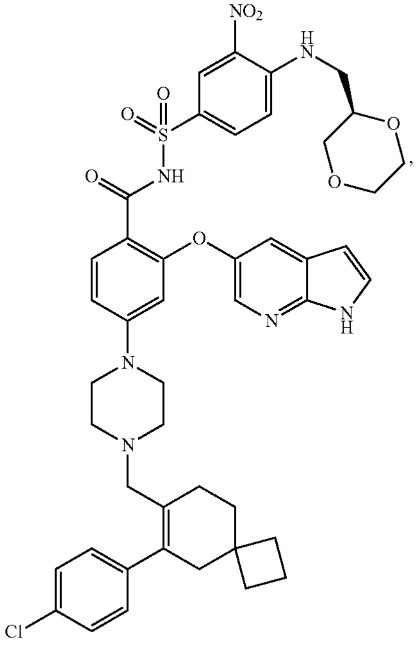

, or a pharmaceutically acceptable salt, hydrate, solvate, or tautomer thereof.

In some embodiments, the disclosure relates to Compound (1)

(1)

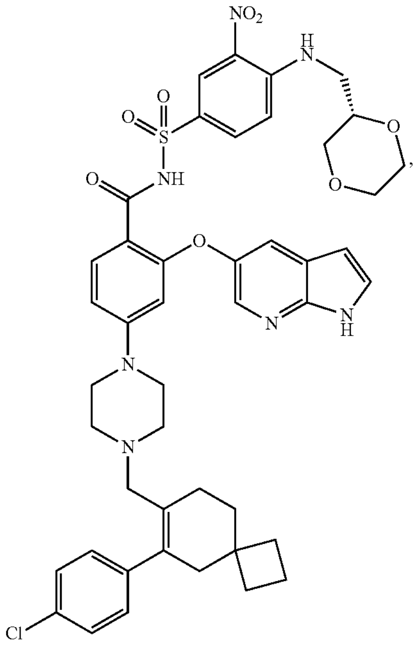

, or a pharmaceutically acceptable salt, hydrate, solvate, or tautomer thereof.

In some embodiments, the disclosure relates to Compound (2)

(2)

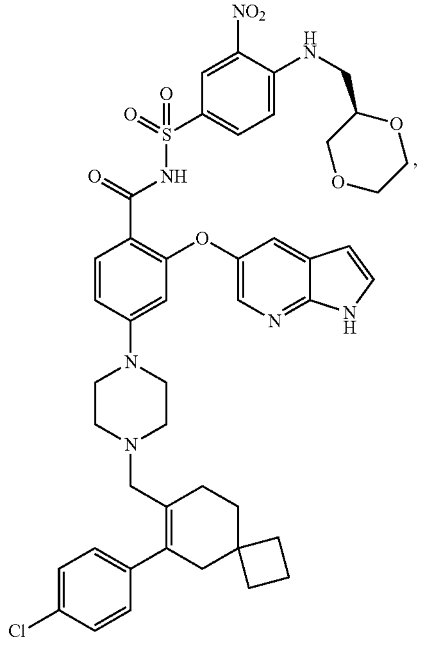

or a pharmaceutically acceptable salt, hydrate, solvate, or tautomer thereof.

In some embodiments, the disclosure relates to a mixture of Compound (1) and Compound (2).

In some embodiments, the disclosure relates to a compound selected from:

(S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide; and (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, or a pharmaceutically acceptable salt, hydrate, solvate, or tautomer thereof.

In some embodiments, the disclosure relates to (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, or a pharmaceutically acceptable salt, hydrate, solvate, or tautomer thereof.

In some embodiments, the disclosure relates to (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, or a pharmaceutically acceptable salt, hydrate, solvate, or tautomer thereof.

In some embodiments, the disclosure relates to a mixture of (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide and (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, or pharmaceutically acceptable salts, hydrates, solvates, or tautomers thereof.

The present disclosure encompasses any of the compounds of formula (I) being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, sulfur, and chlorine, such as 2H (or deuterium (D)), $^3H$, $^{11}C$, $^{13}C$, $^{14}C$, $^{15}N$, $^{18}O$, $^{17}O$, $^{35}S$, and $^{36}Cl$, respectively, e.g., $^3H$, $^{11}C$, and $^{14}C$. In one embodiment, provided is a composition wherein substantially all of the atoms at a position within the compound of formula (I) are replaced by an atom having a different atomic mass or mass number. In another embodiment, provided is a composition wherein a portion of the atoms at a position within the compound of formula (I) are replaced, i.e., the compound of formula (I) is enriched at a position with an atom having a different atomic mass or mass number. Isotopically-labelled compounds of formula (I) can be prepared by methods known in the art.

The present disclosure encompasses the preparation and use of salts of compounds of formula (I), including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparaginate, glutamate and the like.

When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, iron(III), iron(II), lithium, magnesium, manganese, potassium, sodium, zinc, and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When compounds of the present invention contain relatively basic functionalities, acid addition salts can be obtained by contacting the neutral form of such compounds with a sufficient amount of the desired acid, either neat or in a suitable inert solvent. Acids suitable for the preparation of pharmaceutically acceptable acid addition salts include acetic, ascorbic, benzenesulfonic, benzoic, camphorsulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic, and the like.

The compounds of the disclosure may form acid addition salts or base addition salts, which may be pharmaceutically acceptable salts.

The present disclosure encompasses the preparation and use of solvates of compounds of formula (I). Solvates typically do not significantly alter the physiological activity or toxicity of the compounds, and as such may function as pharmacological equivalents. Compounds of formula (I) can be present as solvated forms with a pharmaceutically acceptable solvent, such as water, methanol, ethanol, and the like, and it is intended that the disclosure includes both solvated and unsolvated forms of compounds of formula (I).

In some embodiments, the solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.* 603-604 (2001). A typical, non-limiting, process of preparing a solvate would involve dissolving a compound of formula (I) in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of formula (I) are capable of modulating the activity of Bcl-2 family proteins. In some embodiments, compounds of formula (I) are capable of modulating the activity of Bcl-2 and/or
Bcl-xL. In some embodiments, compounds of formula (I) are capable of inhibiting Bcl-2 and/or Bcl-xL.

Compound (1), (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, is capable of modulating the activity of Bcl-2 family proteins. In some embodiments, Compound (1) is capable of modulating the activity of Bcl-2 and/or Bcl-xL. In some embodiments, Compound (1) is capable of inhibiting Bcl-2 and/or Bcl-xL.

Compound (2), (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, is capable of modulating the activity of Bcl-2 family proteins. In some embodiments, Compound (2) is capable of modulating the activity of Bcl-2 and/or Bcl-xL. In some embodiments, Compound (2) is capable of inhibiting Bcl-2 and/or Bcl-xL.

The present disclosure includes the discovery that compounds of formula (I), and pharmaceutically acceptable salts, solvates, hydrates, stereoisomers, and tautomers thereof, or pharmaceutical compositions comprising a compound of formula (I), are useful for the treatment of diseases or disorders associated with the activity of Bcl-2 family proteins, such as proliferative diseases like systemic lupus erythematosus.

The present disclosure includes the discovery that Compound (1), (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, and pharmaceutically acceptable salts, solvates, hydrates, stereoisomers, and tautomers thereof, or pharmaceutical compositions comprising a Compound (1), are useful for the treatment of diseases or disorders associated with the activity of Bcl-2 family proteins, such as proliferative diseases like systemic lupus erythematosus.

The present disclosure includes the discovery that Compound (2), (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide, and pharmaceutically acceptable salts, solvates, hydrates, stereoisomers, and tautomers thereof, or pharmaceutical compositions comprising Compound (2), are useful for the treatment of diseases or disorders associated with the activity of Bcl-2 family proteins, such as proliferative diseases like systemic lupus erythematosus.

Methods of Preparing the Compounds of the Disclosure

The compounds of the present disclosure may be made by a variety of methods, including standard chemistry. Suitable synthetic routes are depicted in the examples given below.

The compounds of the present disclosure, i.e., compounds of formula (I), or a pharmaceutically acceptable salt, hydrate, solvate, stereoisomer, or tautomer thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize stereocenters exist in the compounds of formula (I). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Compounds of the disclosure are prepared using methods known to those skilled in the art in view of this disclosure, or by the illustrative methods shown in the General Schemes below. For example, methods of preparing the compounds of the disclosure are disclosed in U.S. Pat. No. 10,221,174, the contents of which are incorporated herein in their entirety.

In General Schemes 1-4, presented below, Y, $R^2$, and $R^{4a}$ are defined as follows:

Y=$CH_2$ or O $R^2$=—$NO_2$ $R^{4a}$=A, as defined above with respect to formula (I).

General Scheme 1

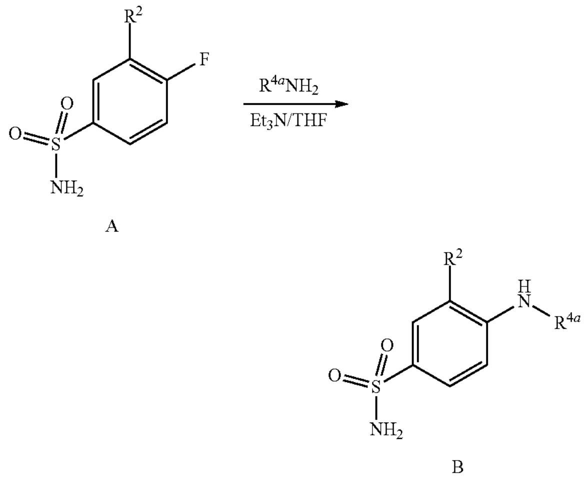

A
B

In General Scheme 1, Compound A is reacted with $R^{4a}NH_2$ in the presence of a base, e.g., triethylamine, to give Compound B.

General Scheme 2

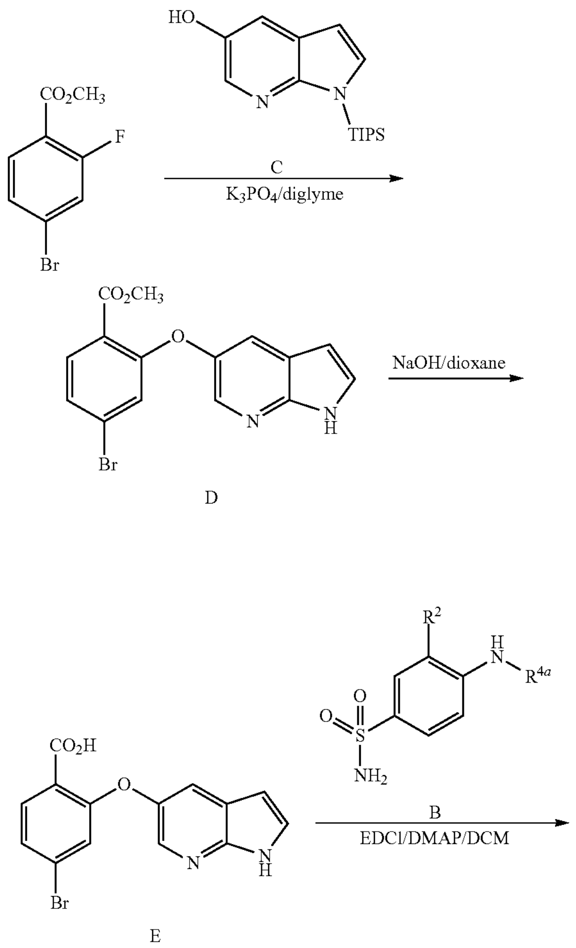

C
D
E
B

-continued

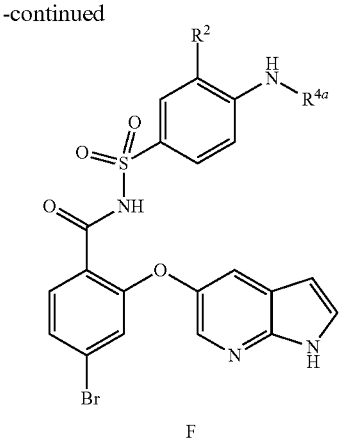
F

In General Scheme 2, methyl 4-bromo-2-fluorobenzoate is reacted with Compound C to give Compound D, and the ester of Compound D is hydrolyzed to give Compound E. Compound E is coupled with Compound B from General Scheme 1 to give Compound F.

General Scheme 3

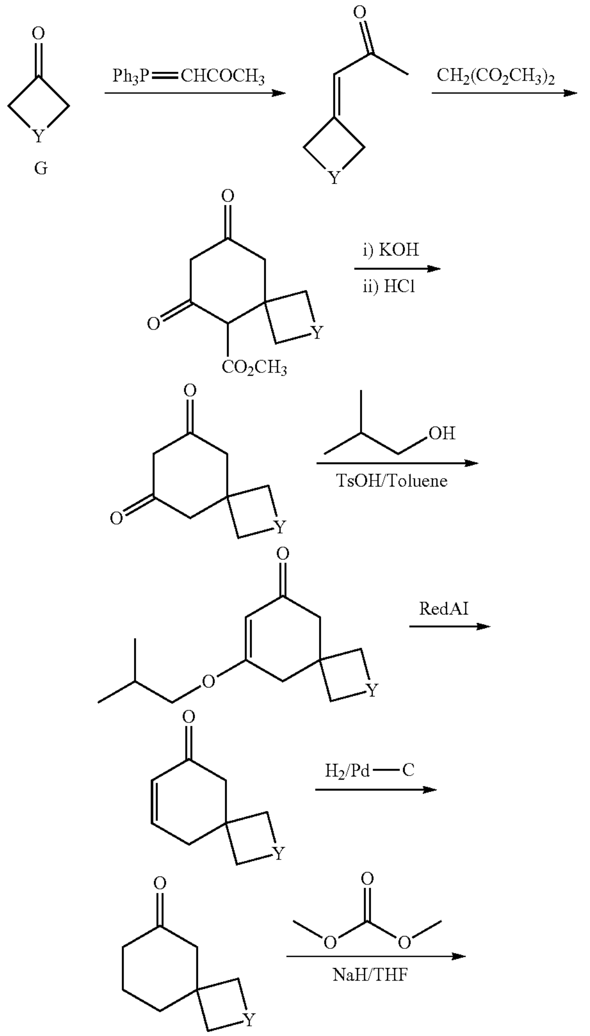

G

-continued
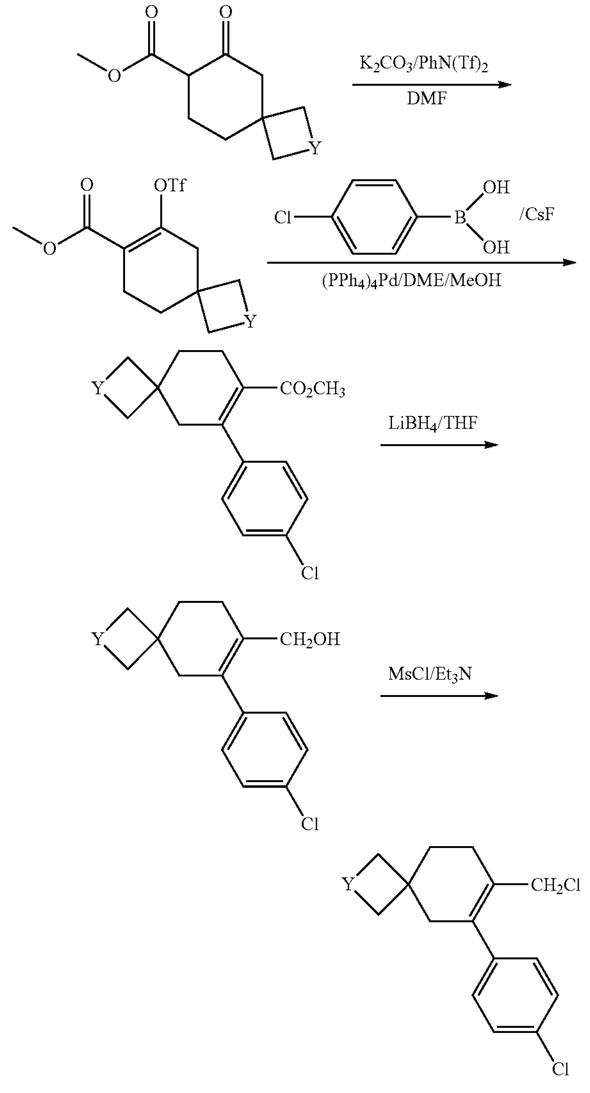
H
Y = $-CH_2-$ or $-O-$
In General Scheme 3, Compound G is transformed Compound H.
General Scheme 4
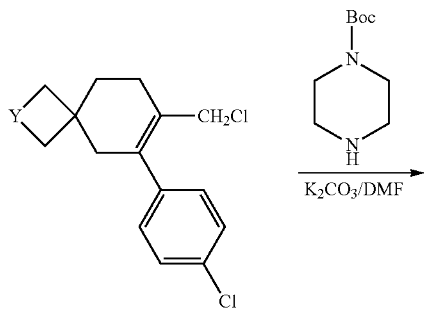
H
-continued
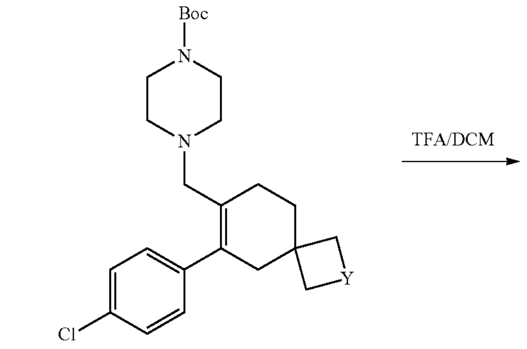
J
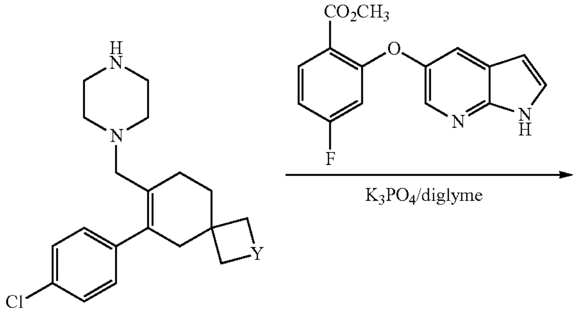
K
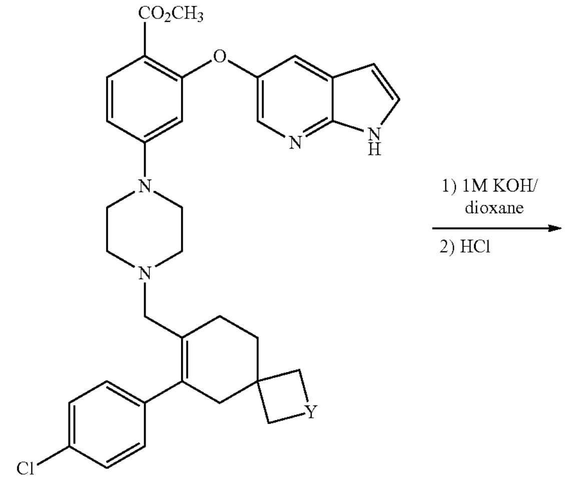
L
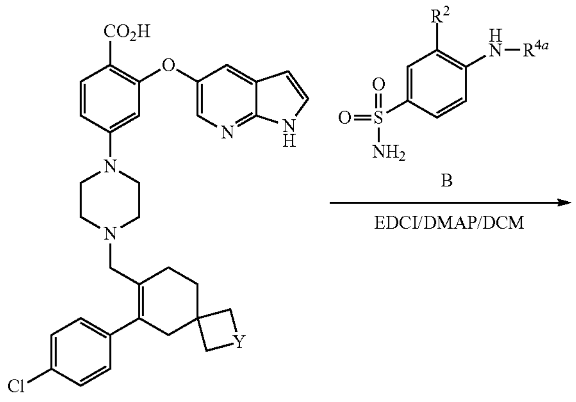
M -continued

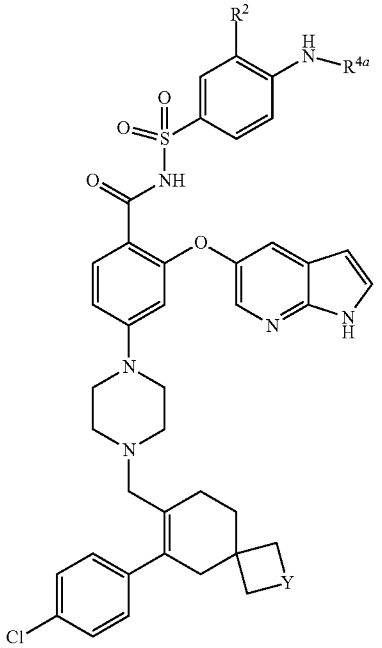

In General Scheme 4, Compound H from General Scheme 3 is reacted with Boc-protected piperidine to give Compound J, and the Boc group is removed to give Compound K. Compound K is reacted with methyl 2-((1H-pyrrolo[2,3-b]pyridin-5-yl)oxy)-4-fluorobenzoate to give Compound L, and the ester of Compound L is hydrolyzed to give Compound M. Compound M is coupled with Compound B from General Scheme 1 to give a compound of formula (I), wherein E is a nitrogen atom and wherein ═ is a single bond.

General Scheme 5

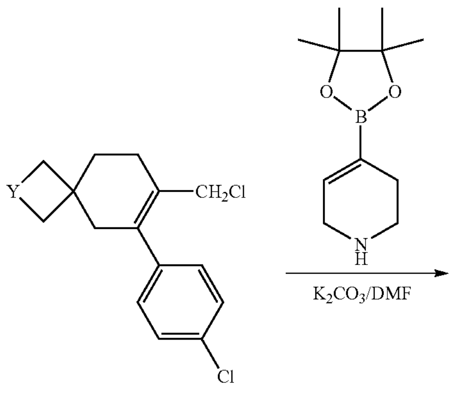

H

-continued

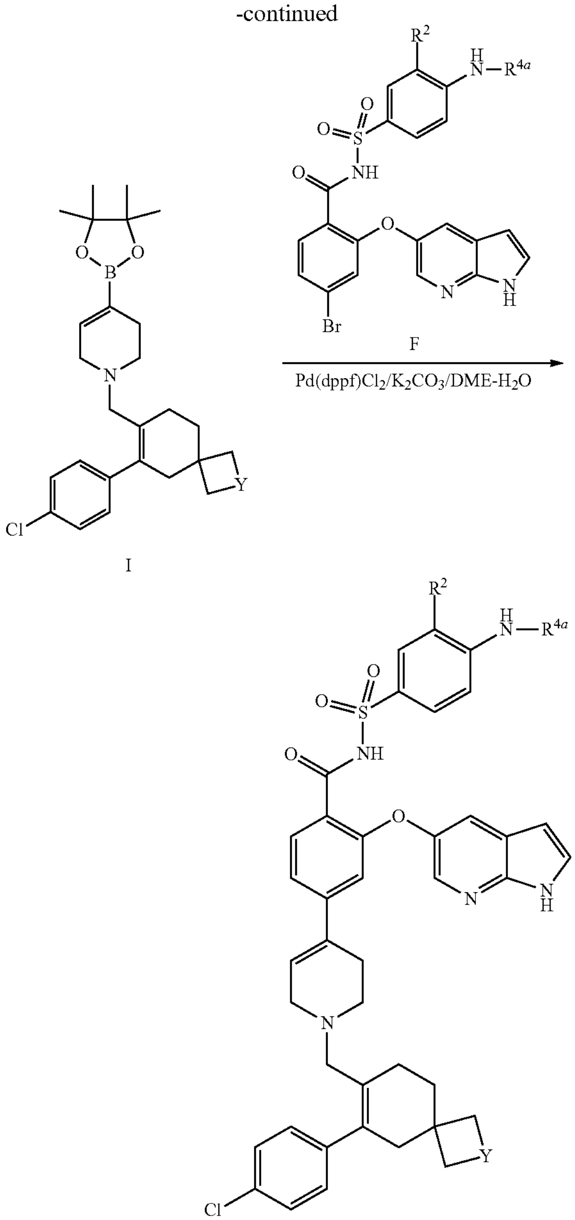

In General Scheme 5, Compound H from General Scheme 3 is reacted with 4-(4,4,5,5-tetramethyl-1,3,2-dioxaborolan-2-yl)-1,2,3,6-tetrahydropyridine to give Compound I. Compound I is coupled with Compound F from General Scheme 2 to give a compound of formula (I), wherein E is a carbon atom and wherein ═ is a double bond.

Methods of Using the Compounds of the Disclosure

Compounds of formula (I) are inhibitors of Bcl-2 proteins, such as Bcl-2, and/or Bcl-xL, and thus, in some embodiments, the compounds are tool compounds useful for studying processes mediated by Bcl-2 proteins in vitro or in vivo. In vitro, the tool compounds of formula (I) may be useful for studying the effects of Bcl-2 family protein inhibition on purified proteins, cellular extracts, in intact cells and cell line models, and the like. In vivo, the tool compounds of formula (I) may be useful for studying the effects of Bcl-2 family protein inhibition in cell line derived xenografts, in patient derived xenografts, in knock-in mouse model, in knock-out mouse models, and the like.

Compounds of formula (I) are inhibitors of Bcl-2 proteins, such as Bcl-2, and/or Bcl-xL, and thus a number of diseases, conditions, or disorders mediated by Bcl-2 proteins can be treated or prevented by administering these compounds to a subject. The present disclosure is thus directed generally to a method for treating or preventing a disease, condition, or disorder responsive to the inhibition of Bcl-2 proteins, such as Bcl-2, and/or Bcl-xL, in an animal suffering from, or at risk of suffering from, the disease, condition, or disorder The method comprises administering to the animal an effective amount of one or more compounds of the disclosure.

In one embodiment, compounds of the disclosure have a Bcl-2 and/or Bcl-xL $IC_{50}$ of less than about 10 μM. In another embodiment, compounds of the disclosure have a Bcl-2 and/or Bcl-xL $IC_{50}$ of less than about 5 μM. In another embodiment, compounds of the disclosure have a Bcl-2 and/or Bcl-xL $IC_{50}$ of less than about 1 μM. In another embodiment, compounds of the disclosure have a Bcl-2 and/or Bcl-xL $IC_{50}$ of less than about 0.5 μM. In another embodiment, compounds of the disclosure have a Bcl-2 and/or Bcl-xL $IC_{50}$ of less than about 0.1 μM. In another embodiment, compounds of the disclosure have a Bcl-2 and/or Bcl-xL $IC_{50}$ of less than about 0.05 μM. In another embodiment, compounds of the disclosure have a Bcl-2 and/or Bcl-xL $IC_{50}$ of less than about 0.025 μM. In another embodiment, compounds of the disclosure have a Bcl-2 and/or Bcl-xL $IC_{50}$ of less than about 0.010 μM. In another embodiment, compounds of the disclosure have a Bcl-2 and/or Bcl-xL $IC_{50}$ of less than about 0.005 μM. In another embodiment, compounds of the disclosure have a Bcl-2 and/or Bcl-xL $IC_{50}$ of less than about 0.0025 μM. In another embodiment, compounds of the disclosure have a Bcl-2 and/or Bcl-xL $IC_{50}$ of less than about 0.001 μM.

The present disclosure is further directed to a method of inhibiting Bcl-2 family proteins in an animal, e.g., a human, in need thereof, the method comprising administering to the animal a therapeutically effective amount of at least one compound of the disclosure. In another embodiment, the present disclosure is directed to a method of inhibiting Bcl-2 family proteins in an animal, e.g., a human, in need thereof, the method comprising administering to the animal a therapeutically effective amount of a pharmaceutical composition comprising at least one compound of the disclosure.

The present disclosure is further directed to a method of inhibiting Bcl-2 in an animal, e.g., a human, in need thereof, the method comprising administering to the animal a therapeutically effective amount of at least one compound of the disclosure. In another embodiment, the present disclosure is directed to a method of inhibiting Bcl-2 in an animal, e.g., a human, in need thereof, the method comprising administering to the animal a therapeutically effective amount of a pharmaceutical composition comprising at least one compound of the disclosure.

The present disclosure is further directed to a method of inhibiting Bcl-xL in an animal, e.g., a human, in need thereof, the method comprising administering to the animal a therapeutically effective amount of at least one compound of the disclosure. In another embodiment, the present disclosure is directed to a method of inhibiting Bcl-xL in an animal, e.g., a human, in need thereof, the method comprising administering to the animal a therapeutically effective amount of a pharmaceutical composition comprising at least one compound of the disclosure.

In one aspect, the present disclosure provides a method of treating or preventing a proliferative disease in a subject, e.g., a human, comprising administering a therapeutically effective amount of a compound of the disclosure or a pharmaceutical composition comprising at least one compound of the disclosure. In some embodiments, the present disclosure provides a method of treating, preventing, or ameliorating an autoimmune disorder in a subject, e.g. a human, comprising administering a therapeutically effect amount of a compound of the disclosure or a pharmaceutical composition comprising at least one compound of the disclosure.

The present disclosure provides a method of treating or ameliorating systemic lupus erythematosus in a subject, e.g. a human, comprising administering a therapeutically effective amount of a compound of the disclosure, or a pharmaceutical composition comprising at least one compound of the disclosure, to the patient in need thereof. In one embodiment, the patient is further diagnosed as having lupus nephritis. In one embodiment, the patient is diagnosed as having an elevated level of circulating
anti-dsDNA antibodies.

Compounds of the disclosure can be administered to a subject in the form of a raw chemical without any other components present. Compounds of the disclosure can also be administered to a subject as part of a pharmaceutical composition containing the compound combined with one or more suitable pharmaceutically acceptable carriers. Such carriers can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

Pharmaceutical compositions within the scope of the present disclosure include all compositions where a compound of the disclosure is combined with one or more pharmaceutically acceptable carriers. In one embodiment, the compound of the disclosure is present in the composition in an amount that is effective to achieve its intended therapeutic purpose. While individual needs may vary, a determination of optimal ranges of effective amounts of each compound is within the skill of the art. Typically, a compound of the disclosure can be administered to a mammal, e.g., a human, orally at a dose of from about 0.0025 to about 1500 mg per kg body weight of the mammal, or an equivalent amount of a pharmaceutically acceptable salt, hydrate, solvate, stereoisomer, or tautomer thereof, per day to treat the particular disorder. A useful oral dose of a compound of the disclosure administered to a mammal is from about 0.0025 to about 200 mg per kg body weight of the mammal, or an equivalent amount of the pharmaceutically acceptable salt or solvate thereof. For intramuscular injection, the dose is typically about one-half of the oral dose. In some embodiments, the compound of the disclosure, or a pharmaceutically acceptable salt, hydrate, solvate, stereoisomer, or tautomer thereof is administered once per day.

A unit oral dose may comprise from about 0.01 mg to about 1 g of the compound of the disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt, hydrate, solvate, stereoisomer, or tautomer thereof.

In some embodiments, the compound of the disclosure, or a pharmaceutical composition comprising at least one compound of the disclosure, is administered to the patient in need thereof at a dose sufficient to elicit one or more effects selected from the group consisting of reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced vasculitis severity in the patient, reduced lymphocyte cell counts in a peripheral blood mononuclear cell (PBMC) panel taken from the patient, reduced lymphocyte cell counts in the spleen of the patient, and reduced lymphocyte infiltration of the kidneys of the patient.

In one embodiment, the compound of the disclosure, or a pharmaceutical composition comprising at least one compound of the disclosure, is administered to the patient in need thereof at a dose sufficient to reduce excretion of protein in the urine of the patient.

In one embodiment, the compound of the disclosure, or a pharmaceutical composition comprising at least one compound of the disclosure, is administered to the patient in need thereof at a dose sufficient to reduce serum anti-dsDNA autoantibody levels in the patient.

In one embodiment, the compound of the disclosure, or a pharmaceutical composition comprising at least one compound of the disclosure, is administered to the patient in need thereof at a dose sufficient to reduce skin lesion severity in the patient.

In one embodiment, the compound of the disclosure, or a pharmaceutical composition comprising at least one compound of the disclosure, is administered to the patient in need thereof at a dose sufficient to reduce lymphadenopathy severity in the patient.

In one embodiment, the compound of the disclosure, or a pharmaceutical composition comprising at least one compound of the disclosure, is administered to the patient in need thereof at a dose sufficient to reduce glomerulonephritis severity in the patient.

In one embodiment, the compound of the disclosure, or a pharmaceutical composition comprising at least one compound of the disclosure, is administered to the patient in need thereof at a dose sufficient to reduce interstitial nephritis severity in the patient.

In one embodiment, the compound of the disclosure, or a pharmaceutical composition comprising at least one compound of the disclosure, is administered to the patient in need thereof at a dose sufficient to reduce vasculitis severity in the patient.

In one embodiment, the compound of the disclosure, or a pharmaceutical composition comprising at least one compound of the disclosure, is administered to the patient in need thereof at a dose sufficient to reduce lymphocyte cell counts in a peripheral blood mononuclear cell (PBMC) panel taken from the patient.

In one embodiment, the compound of the disclosure, or a pharmaceutical composition comprising at least one compound of the disclosure, is administered to the patient in need thereof at a dose sufficient to reduce lymphocyte cell counts in the spleen of the patient.

In one embodiment, the compound of the disclosure, or a pharmaceutical composition comprising at least one compound of the disclosure, is administered to the patient in need thereof at a dose sufficient to reduce lymphocyte infiltration in the kidneys of the patient.

A compound of the disclosure or a pharmaceutical composition comprising a compound of the disclosure can be administered to any patient or subject that may experience the beneficial effects of a compound of the disclosure. Foremost among such patients or subject are mammals, e.g., humans and companion animals, although the disclosure is not intended to be so limited. In one embodiment, the patient or subject is a human.

A compound of the disclosure or a pharmaceutical composition comprising a compound of the disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a compound of the disclosure or a pharmaceutical composition comprising a compound of the disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the compound of the disclosure.

Alternatively, a compound of the disclosure or a pharmaceutical composition comprising a compound of the disclosure can be administered rectally, and is formulated in suppositories.

Alternatively, a compound of the disclosure or a pharmaceutical composition comprising a compound of the disclosure can be administered by injection.

Alternatively, a compound of the disclosure or a pharmaceutical composition comprising a compound of the disclosure can be administered transdermally.

Alternatively, a compound of the disclosure or a pharmaceutical composition comprising a compound of the disclosure can be administered by inhalation or by intranasal or transmucosal administration.

Alternatively, a compound of the disclosure or a pharmaceutical composition comprising a compound of the disclosure can be administered by the intravaginal route.

A pharmaceutical composition of the present disclosure can contain from about 0.01 to 99 percent by weight, e.g., from about 0.25 to 75 percent by weight, of a compound of the disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a compound of the disclosure.

A pharmaceutical composition of the present disclosure can contain one or more of a compound of formula (I). In some embodiments, the pharmaceutical composition contains Compound 1 and Compound 2 of the foregoing structures, or a pharmaceutically acceptable salt, hydrate, solvate, or tautomer thereof. In one embodiment, the pharmaceutical composition contains Compound 1 of the foregoing structure, or a pharmaceutically acceptable salt, solvate, hydrate, or tautomer thereof, at a purity of at least 90%, wherein the composition comprises less than 10%, e.g. less than 9%, less than 8%, less than 7%, less than 6%, less than 5%, less than 4%, less than 3%, less than 2% or less than 1% of Compound 2 of the foregoing structure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate can be used. Dye stuffs or pigments can be added to the tablets or dragee coatings, for example, for identification orin order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a compound of the disclosure (or a pharmaceutical composition comprising a compound of the disclosure) packaged in a manner that facilitates their use to practice methods of the present disclosure. In one embodiment, the kit includes a compound of the disclosure (or a pharmaceutical composition comprising a compound of the disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

In another embodiment, a compound of the disclosure, or a pharmaceutical composition comprising a compound of the disclosure, is administered to a subject in conjunction with a second therapeutic agent. The second therapeutic agent is different from the compound of the disclosure. A compound of the disclosure and the second therapeutic agent can be administered simultaneously or sequentially to achieve the desired effect. In some embodiments, the second therapeutic agent is administered before the compound of the disclosure, or a pharmaceutical composition comprising the compound of the disclosure. In some embodiments, the second therapeutic agent is administered after the compound of the disclosure, or a pharmaceutical composition comprising the compound of the disclosure. In some embodiments, the second therapeutic agent is administered simultaneously with the compound of the disclosure, or a pharmaceutical composition comprising the compound of the disclosure. In addition, the compound of the disclosure and second therapeutic agent can be administered as a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of the disclosure and the second therapeutic agent can be administered together as a single-unit dose or separately as multi-unit doses, wherein the compound of the disclosure is administered before the second therapeutic agent or vice versa. One or more doses of the compound of the disclosure and/or one or more dose of the second therapeutic agent can be administered. The compound of the disclosure therefore can be used in conjunction with one or more second therapeutic agents, for example, but not limited to, autoimmune disorder therapeutic agents.

In some embodiments, the second therapeutic agent is an autoimmune disorder therapeutic agent.

In some embodiments, the second therapeutic agent is a systemic lupus erythematosus therapeutic agent. For example, systemic lupus erythematosus therapeutic agents may include, but are not limited to, non-steroidal anti-inflammatory drugs, anti-malarials, steroids, immunosuppressants, and dehydroepiandrosterone (DHEA).

Non-limiting examples of non-steroidal anti-inflammatory drugs used as systemic lupus erythematosus therapeutic agents include celecoxib, diflunisal, etodolac, ibuprofen, indomethacin, meloxicam, midrin, nabumetone, naproxen, oxaprozin, piroxicam, salsalate, sulindac, tolmetin, trilisate, and ketoprofen.

Non-limiting examples of anti-malarials used as systemic lupus erythematosus therapeutic agents include hydroxychloroquine, chloroquine, and quinacrine.

Non-limiting examples of steroids used as systemic lupus erythematosus therapeutic agents include prednisone, prednisolone, hydrocortisone, methylprednisolone, dexamethasone, triamcinolone, and topical steroids.

Non-limiting examples of immunosuppressants used as systemic lupus erythematosus therapeutic agents include azathioprine, mycophenolate mofetil, cyclosporine, methotrexate, leflunomide, cyclophosphamide, chlorambucil, and nitrogen mustard.

The above-mentioned second therapeutically active agents, one or more of which can be used in combination with a compound of the disclosure, are prepared and administered as described in the art.

EXAMPLES

Example 1—Synthesis of Intermediates

Intermediate 1

Synthesis of 1-cyclobutylidenepropan-2-one

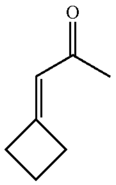

To a solution of cyclobutanone (5.0 g, 71.4 mmol) in toluene (200 ml) was added 1-(triphenylphosphoranylidene)-2-propanone (22.7 g, 71.4 mmol) and the mixture was refluxed overnight. Solvent was removed under reduced pressure and the residue was purified by silica gel column chromatography (ethyl acetate/hexane 1/10-1/5) to afford 1-cyclobutylidenepropan-2-one (5.0 g) as yellow oil. $^1$H NMR (400 MHz, $CDCl_3$) δ 5.95-5.93 (m, 1H), 3.19-3.13 (m, 2H), 2.91-2.84 (m, 2H), 2.21 (s, 3H), 2.21-2.11 (m, 2H).

Intermediate 2

Synthesis of Spiro[3.5]nonane-6,8-dione

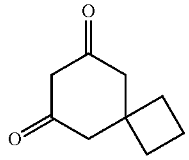 [SMILES: O=C1CC(=O)CC2(CCC2)C1]

To a solution of 1-cyclobutylidenepropan-2-one (23.1 g, 0.21 mol) and methyl malonate (30.3 g, 0.23 mol) in methanol (150 ml) was added sodium methoxide (41.4 g, 30% in methanol). The mixture was heated to reflux under nitrogen for 4 h and concentrated. The resulting residue was hydrolyzed in 2N potassium hydroxide (200 ml) at 70° C. for 4 h. The mixture was extracted with ethyl acetate (100 ml), then titrated to pH 3-5 with 1N hydrochloric acid. The resulting solution was heated to 70° C. for 5 h and extracted with ethyl acetate (100 ml×3). The combined organic layers were dried over magnesium sulfate and concentrated to afford spiro[3.5]nonane-6,8-dione (19.8 g, 62.3%) as yellow solid. This product was used directly in the next step without further purification. $^1$H NMR (400 MHz, DMSO-d6) δ 11.05 (s, 1H), 5.17 (s, 1H), 2.50-2.35 (m, 4H), 1.92-1.79 (m, 2H), 1.79-1.72 (m, 4H).

Intermediate 3

8-isobutoxyspiro[3.5]non-7-en-6-one

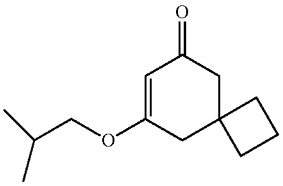

To a solution of spiro[3.5]nonane-6,8-dione (19.8 g, 0.13 mol) in toluene (150 ml) was added 4-toluenesulfonic acid (248 mg, 0.0013 mol) and iso-butyl alcohol (14.5 g, 0.2 mol). The mixture was heated to reflux and water was removed by azeotropic distillation. Solvent was removed under vacuum and the residue was purified by silica gel column chromatography (ethyl acetate/petrol ether 1/10-1/3) to afford 8-isobutoxyspiro[3.5]non-7-en-6-one (25.0 g, 92.7%) as light yellow oil. $^1$H NMR (400 MHz, $CDCl_3$) δ 5.31 (s, 1H), 3.59 (d, J=6.8 Hz, 2H), 2.51 (s, 2H), 2.45 (s, 2H), 2.12-1.96 (m, 1H), 1.93-1.83 (m, 6H), 0.99 (d, J=6.8 Hz, 6H).

Intermediate 4

Synthesis of Spiro[3.5]non-7-en-6-one

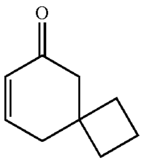

To a solution of 8-isobutoxyspiro[3.5]non-7-en-6-one (25.0 g, 0.12 mol) in toluene (100 mL) was added Red-Al® (40 ml, 70% in toluene, 0.18 mol) dropwise at room temperature. The mixture was heated to 45° C. for 4 h, then quenched by 1N hydrochloric acid. The mixture was filtered and the filtrate was concentrated and purified by silica gel column chromatography (ethyl acetate/petrol ether 1/10) to afford spiro[3.5]non-7-en-6-one (9.0 g, 55%) as light yellow oil.

Intermediate 5

Synthesis of Spiro[3.5]nonan-6-one

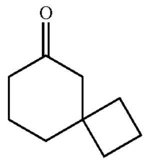

Spiro[3.5]non-7-en-6-one (9.0 g) was hydrogenated under 1 atm hydrogen, catalyzed by 10% Pd/C (1.0 g) in methanol (80 ml) for 5.5 h. Pd/C was removed by filtration and the filtrate was concentrated to afford spiro[3.5]nonan-6-one (8.8 g, 96.4%) as colorless oil which was used directly in the next step without further purification. $^1$H NMR (400 MHz, $CDCl_3$) δ 2.38 (s, 2H), 2.23-2.20 (m, 2H), 1.89-1.75 (m, 10H).

Intermediate 6

Synthesis of Methyl 6-oxospiro[3.5]nonane-7-carboxylate

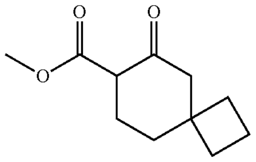

To a suspension of sodium hydride (5.1 g, 0.13 mol) in tetrahydrofuran (150 mL) was added methyl carbonate (28.7 g, 0.32 mol) at room temperature, followed by spiro[3.5]nonan-6-one in tetrahydrofuran (30 mL). The mixture was refluxed for 2 h. The reaction was quenched by saturated aqueous ammonium chloride and extracted with ethyl acetate (100 mL×3). The combined organic layers were washed with brine and concentrated. The resulting residue was purified by silica gel column chromatography to afford methyl 6-oxospiro[3.5]nonane-7-carboxylate (4.0 g, 32%) as light yellow oil.

Intermediate 7

Synthesis of Methyl 6-(((trifluoromethyl)sulfonyl)oxy)spiro[3.5]non-6-ene-7-carboxylate

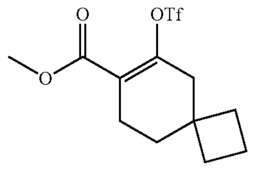 [SMILES: COC(=O)C1=C(OS(=O)(=O)C(F)(F)F)CC2(CCC2)CC1]

To a solution of methyl 6-oxospiro[3.5]nonane-7-carboxylate (4.0 g, 0.02 mol) in tetrahydrofuran (25 mL) were added potassium carbonate (5.6 g, 0.04 mol) and N,N-bis(trifluoromethylsulfonyl)aniline (7.9 g, 0.022 mol). The mixture was stirred at room temperature overnight, diluted with water, and extracted with ethyl acetate (100 mL×3). The combined organic layers were washed with saturated brine, dried over magnesium sulfate and concentrated. The resulting residue was purified by silica gel column chromatography (ethyl acetate/petrol ether 1/50-1/10) to afford methyl 6-(((trifluoromethyl)sulfonyl)oxy)spiro[3.5]non-6-ene-7-carboxylate (5.0 g, 76%) as light yellow oil.

Intermediate 8

Synthesis of Methyl 6-(4-chlorophenyl)spiro[3.5]non-6-ene-7-carboxylate

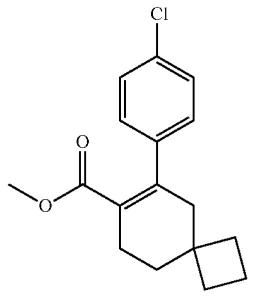 [SMILES: COC(=O)C1=C(c2ccc(Cl)cc2)CC2(CCC2)CC1]

The mixture of methyl 6-(((trifluoromethyl)sulfonyl)oxy)spiro[3.5]non-6-ene-7-carboxylate (5.0 g, 0.015 mol), 4-chlorophenyl boronic acid (2.58 g, 0.017 mol), CsF (4.63 g, 0.03 mol) and $Pd(PPh_3)_4$ (173 mg, 0.15 mol) in 1,2-dimethoxy-ethane (30 ml) and methanol (15 ml) was heated to 70° C. under nitrogen for 2 h. Solvents were removed under reduced pressure and the residue was purified by silica gel column chromatography (ethyl acetate/petrol ether 1/10) to afford methyl 6-(4-chlorophenyl)spiro[3.5]non-6-ene-7-carboxylate (4.0 g, 92%) as colorless oil. $^1$H NMR (400 MHz, $CDCl_3$) δ 7.30 (d, J=8.5 Hz, 2H), 7.06 (d, J=8.5 Hz, 2H), 3.48 (s, 3H), 2.50-2.44 (m, 2H), 2.43 (t, J=2.3 (2.3 or 6.3?) Hz, 2H), 2.02-1.80 (m, 6H), 1.74 (t, J=6.3 Hz, 2H).

Intermediate 9

Synthesis of (6-(4-Chlorophenyl)spiro[3.5]non-6-en-7-yl)methanol

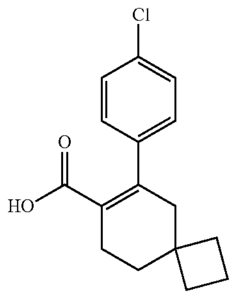 [SMILES: O=C(O)C1=C(c2ccc(Cl)cc2)CC2(CCC2)CC1]

To a solution of methyl 6-(4-chlorophenyl)spiro[3.5]non-6-ene-7-carboxylate (4.0 g, 0.014 mol) in tetrahydrofuran (20 mL) was added a solution of $LiBH_4$ (910 mg, 0.042 mol) in tetrahydrofuran (10 mL). The mixture was stirred at room temperature overnight, quenched by 1N aqueous hydrochloric acid and extracted with ethyl acetate (100 mL×3). The combined organic layers were washed with brine, dried over magnesium sulfate and concentrated. The resulting residue was purified by silica gel column chromatography (ethyl acetate/petrol ether 1/10-1/3) to afford (6-(4-chlorophenyl)spiro[3.5]non-6-en-7-yl)methanol (3.0 g, 81.7%) as a white solid. $^1$H NMR (400 MHz, $CDCl_3$) δ 7.31 (d, J=8.4 Hz, 2H), 7.09 (d, J=8.4 Hz, 2H), 3.93 (d, J=4.2 Hz, 2H), 2.37-2.26 (m, 2H), 2.01-1.77 (m, 8H), 1.74 (t, J=6.3 Hz, 2H).

Intermediate 10

Synthesis of 7-(Chloromethyl)-6-(4-chlorophenyl)spiro[3.5]non-6-ene

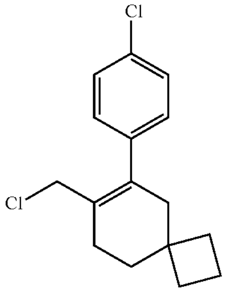 [SMILES: ClCC1=C(c2ccc(Cl)cc2)CC2(CCC2)CC1]

To a solution of (6-(4-chlorophenyl)spiro[3.5]non-6-en-7-yl)methanol (3.5 g, 0.013 mol) and trimethylamine (2.7 g, 0.026 mol) in dichloromethane (20 mL) was added methylsulfonyl chloride (3.0 g, 0.026 mol) dropwise. The mixture was stirred at room temperature for 5 h. Solvent was removed under reduced pressure and the residue was purified by silica gel column chromatography to afford 7-(chloromethyl)-6-(4-chlorophenyl)spiro[3.5]non-6-ene (2.75 g, 75.5%) as yellow oil. $^1$H NMR (400 MHz, $CDCl_3$) δ 7.31 (d, J=8.4 Hz, 2H), 7.09 (d, J=8.5 Hz, 2H), 3.93 (s, 2H), 2.34-2.25 (m, 4H), 1.97-1.78 (m, 6H), 1.74 (t, J=6.3 Hz, 2H).

Intermediate 11

Synthesis of Methyl 2-((1H-pyrrolo[2,3-b]pyridin-5-yl)oxy)-4-bromobenzoate

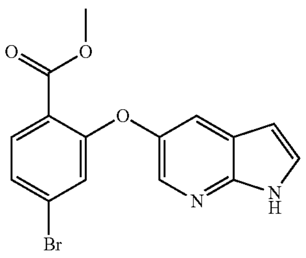 [SMILES: COC(=O)c1ccc(Br)cc1Oc1cnc2[nH]ccc2c1]

A mixture of 1-(triisopropylsilyl)-1H-pyrrolo[2,3-b]pyridin-5-ol (1.91 g), methyl 4-bromo-2-fluorobenzoate (1.70 g), and K3PO4 (1.86 g) in diglyme (20 mL) was stirred at 115° C. for 1 h. The reaction was cooled, diluted with ethyl acetate (100 mL), washed with water followed by brine, and concentrated. The residue was purified by silica gel chromatography (ethyl acetate/hexane 1/3) to afford methyl 2-((1H-pyrrolo[2,3-b]pyridin-5-yl)oxy)-4-bromobenzoate (1.8 g) as white solid. $^1$H NMR (400 MHz, $CDCl_3$) δ 9.28 (s, 1H), 8.18 (d, J=2.5 Hz, 1H), 7.79 (d, J=8.4 Hz, 1H), 7.62 (d, J=2.5 Hz, 1H), 7.40-6.96 (m, 2H), 6.96 (d, J=1.7 Hz, 1H), 6.51-6.48 (m, 1H), 3.89 (s, 3H).

Intermediate 12

Synthesis of 2-((1H-pyrrolo[2,3-b]pyridin-5-yl)oxy)-4-bromobenzoic acid

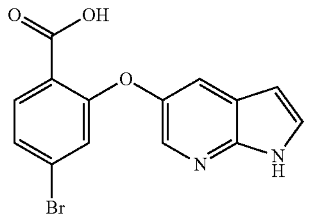 [SMILES: O=C(O)c1ccc(Br)cc1Oc1cnc2[nH]ccc2c1]

To a solution of methyl 2-((1H-pyrrolo[2,3-b]pyridin-5-yl)oxy)-4-bromobenzoate (300 mg, 0.867 mmol) in dioxane (10 mL) was added 1N NaOH (2.2 mL, 2.2 mmol) and the mixture was stirred at room temperature for 2 h. The mixture was acidified by 1N HCl and extracted with ethyl acetate, washed with brine, and dried over anhydrous $MgSO_4$. Evaporation under reduced pressure afforded crude 2-((1H-pyrrolo[2,3-b]pyridin-5-yl)oxy)-4-bromobenzoic acid as a colorless oil. This product was used directly in the next step without further purification.

Intermediate 13

Synthesis of 2-((1H-pyrrolo[2,3-b]pyridin-5-yl)oxy)-4-bromo-N-((3-nitro-4-(((tetrahydro-2H-pyran-4-yl)methyl)amino)phenyl)sulfonyl) benzamide

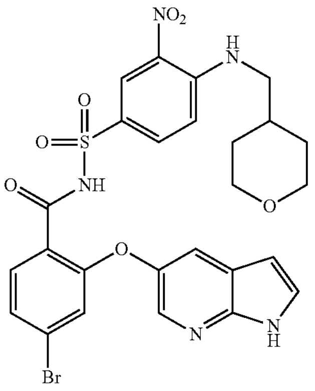 [SMILES: O=C(NS(=O)(=O)c1ccc(NCC2CCOCC2)c([N+](=O)[O-])c1)c1ccc(Br)cc1Oc1cnc2[nH]ccc2c1]

To a solution of 2-((1H-pyrrolo[2,3-b]pyridin-5-yl)oxy)-4-bromobenzoic acid (100 mg, 0.3 mmol) in DCM (10 mL) were added 3-nitro-4-(((tetrahydro-2H-pyran-4-yl)methyl)amino)benzenesulfonamide (95 mg, 0.3 mmol), DMAP (55 mg, 0.45 mmol) and EDCI (115 mg, 0.6 mmol) and the mixture was stirred at room temperature for 24 h. Solvent was removed under reduced pressure and the residue was purified by silica gel chromatography (DCM/MeOH 95/5) to afford 2-((1H-pyrrolo[2,3-b]pyridin-5-yl)oxy)-4-bromoN-((3-nitro-4-(((tetrahydro-2H-pyran-4-yl)methyl)amino)phenyl) sulfonyl)benzamide as a yellow oil (80 mg). MS m/z 630 $[M+H]^+$.

Intermediate 14

Synthesis of (S)—N-((4-(((1,4-Dioxan-2-yl)methyl)amino)-3-nitrophenyl)sulfonyl)-2-((1H-pyrrolo[2,3-b]pyridin-5-yl)oxy)-4-bromobenzamide

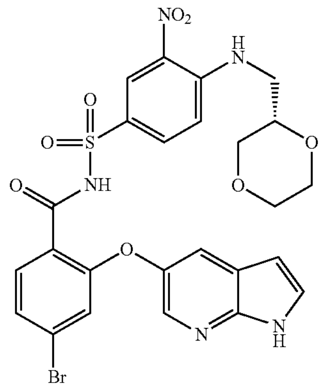 [SMILES: O=C(NS(=O)(=O)c1ccc(NC[C@H]2COCCO2)c([N+](=O)[O-])c1)c1ccc(Br)cc1Oc1cnc2[nH]ccc2c1]

To a solution of 2-((1H-pyrrolo[2,3-b]pyridin-5-yl)oxy)-4-bromobenzoic acid (100 mg, 0.3 mmol) in DCM (10 mL) were added (S)-4-(((1,4-dioxan-2-yl)methyl)amino)-3-nitrobenzenesulfonamide (95 mg, 0.3 mmol), DMAP (55 mg, 0.45 mmol) and EDCI (115 mg, 0.6 mmol) and the mixture was stirred at room temperature for 24 h. Solvent was removed under reduced pressure and the residue was purified by silica gel chromatography (DCM/MeOH 95/5) to afford (S)—N-((4-(((1,4-Dioxan-2-yl)methyl)amino)-3-nitrophenyl)sulfonyl)-2-((1H-pyrrolo[2,3-b]pyridin-5-yl)oxy)-4-bromobenzamide. $^1$H NMR (400 MHz, DMSO-d6) δ 11.79 (s, 1H), 8.59-8.52 (m, 2H), 8.05 (d, J=2.6 Hz, 1H), 7.85 (dd, J=9.2, 2.4 Hz, 1H), 7.66 (d, J=2.6 Hz, 1H), 7.59-7.49 (m, 1H), 7.48 (d, J=8.2 Hz, 1H), 7.34 (dd, J=8.2, 1.8 Hz, 1H), 7.12 (d, J=9.2 Hz, 1H), 6.88 (d, J=1.8 Hz, 1H), 6.50-6.40 (m, 1H), 3.83-3.37 (m, 2H), 3.72-3.56 (m, 2H), 3.56-3.42 (m, 2H), 3.37-3.01 (m, 3H).

Intermediate 15

Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-bromobenzamide

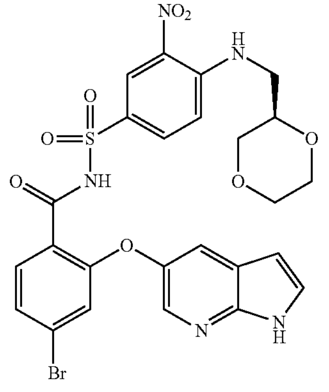 [SMILES: O=C(NS(=O)(=O)c1ccc(NC[C@@H]2COCCO2)c([N+](=O)[O-])c1)c1ccc(Br)cc1Oc1cnc2[nH]ccc2c1]

To a solution of 2-((1H-pyrrolo[2,3-b]pyridin-5-yl)oxy)-4-bromobenzoic acid (100 mg, 0.3 mmol) in DCM (10 mL) were added (R)-4-(((1,4-dioxan-2-yl)methyl)amino)-3-nitrobenzenesulfonamide (95 mg, 0.3 mmol), DMAP (55 mg, 0.45 mmol) and EDCI (115 mg, 0.6 mmol) and the mixture was stirred at room temperature for 24 h. Solvent was removed under reduced pressure and the residue was purified by silica gel chromatography (DCM/MeOH 95/5) to afford (R)—N-((4-(((1,4-dioxan-2-yl)methyl)amino)-3-nitrophenyl)sulfonyl)-2-((1H-pyrrolo[2,3-b]pyridin-5-yl)oxy)-4-bromobenzamide. $^1$H NMR (400 MHz, DMSO-d6) δ 11.79 (s, 1H), 8.59-8.52 (m, 2H), 8.05 (d, J=2.6 Hz, 1H), 7.85 (dd, J=9.2, 2.4 Hz, 1H), 7.66 (d, J=2.6 Hz, 1H), 7.59-7.49 (m, 1H), 7.48 (d, J=8.2 Hz, 1H), 7.34 (dd, J=8.2, 1.8 Hz, 1H), 7.12 (d, J=9.2 Hz, 1H), 6.88 (d, J=1.8 Hz, 1H), 6.50-6.40 (m, 1H), 3.83-3.37 (m, 2H), 3.72-3.56 (m, 2H), 3.56-3.42 (m, 2H), 3.37-3.01 (m, 3H).

Intermediate 16

Synthesis of tert-Butyl-4-(3-((1H-pyrrolo[2,3-b]pyridin-5-yl)oxy)-4-(ethoxycarbonyl)phenyl)piperazine-1-carboxylate

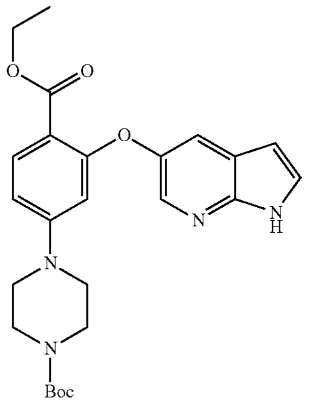 [SMILES: CCOC(=O)c1ccc(N2CCN(C(=O)OC(C)(C)C)CC2)cc1Oc1cnc2[nH]ccc2c1]

A mixture of ethyl 2-((1H-pyrrolo[2,3-b]pyridin-5-yl)oxy)-4-fluorobenzoate (2.1 g, 7 mmol), N-Boc-piperazine (2.61 g, 0.014 mol) and dipotassium hydrogenphosphate (2.44 g, 0.014 mol) in dimethyl sulfoxide was heated to 135° C. overnight. Water was added to the reaction mixture and the mixture was extracted with ethyl acetate (50 mL×3). The combined organic layers were washed with brine, concentrated and purified by silica gel column chromatography to afford tert-butyl 4-(3-((1H-pyrrolo[2,3-b]pyridin-5-yl)oxy)-4-(ethoxycarbonyl)phenyl)piperazine-1-carboxylate (2.4 g, 73%) as a white solid. $^1$H NMR (400 MHz, $CDCl_3$) δ 9.42 (br s, 1H), 8.20 (d, J=2.5 Hz, 1H), 7.95 (d, J=8.9 Hz, 1H), 7.53 (d, J=2.5 Hz, 1H), 7.37 (dd, J=3.5, 2.5 Hz, 1H), 6.66 (dd, J=8.9, 2.5 Hz, 1H), 6.46 (dd, J=3.5, 2.0 Hz, 1H), 6.36 (d, J=2.5 Hz, 1H), 4.28 (q, J=7.1 Hz, 2H), 3.55-3.50 (m, 4H), 3.21-3.17 (m, 4H), 1.47 (s, 9H), 1.26 (t, J=7.1 Hz, 3H).

Intermediate 17

Synthesis of Ethyl 2-((1H-pyrrolo[2,3-b]pyridin-5-yl)oxy)-4-(piperazin-1-yl)benzoate

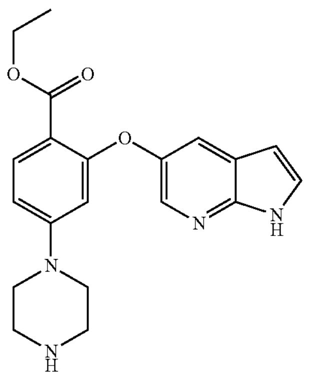 [SMILES: CCOC(=O)c1ccc(N2CCNCC2)cc1Oc1cnc2[nH]ccc2c1]

Trifluoroacetic acid (6 mL) was added to a solution of tert-butyl 4-(3-((1H-pyrrolo[2,3-b]pyridin-5-yl)oxy)-4-(ethoxycarbonyl)phenyl)piperazine-1-carboxylate (2.1 g) in dichloromethane (10 mL) and the mixture was stirred at room temperature for 3 h. Solvent was removed under reduced pressure and the crude ethyl 2-((1H-pyrrolo[2,3-b]pyridin-5-yl)oxy)-4-(piperazin-1-yl)benzoate (2.5 g) was used directly in the next step without further purification.

Intermediate 18

Synthesis of Ethyl 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoate

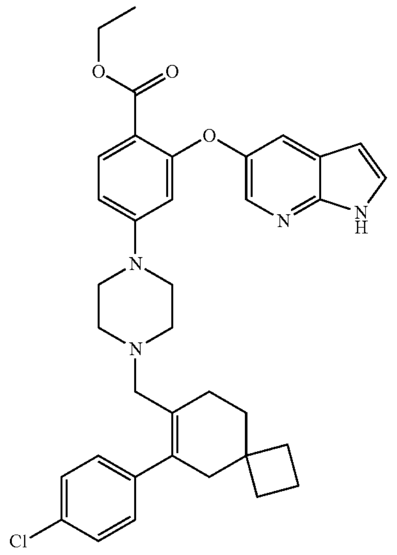 [SMILES: CCOC(=O)c1ccc(N2CCN(CC3=C(c4ccc(Cl)cc4)CC4(CCC4)CC3)CC2)cc1Oc1cnc2[nH]ccc2c1]

To a solution of 7-(chloromethyl)-6-(4-chlorophenyl)spiro[3.5]non-6-ene (851 mg, 3 mmol) in N,N-dimethyl formamide (10 mL) were added potassium carbonate (1.26 g, 9 mmol), potassium iodide (100 mg, 0.6 mmol) and ethyl 2-((1H-pyrrolo[2,3-b]pyridin-5-yl)oxy)-4-(piperazin-1-yl)benzoate (1.53 g, 3.3 mmol). The mixture was stirred at room temperature overnight. The reaction mixture was diluted with water and extracted with ethyl acetate (50 mL×3). The combined organic layers were washed with brine, concentrated and purified by silica gel column chromatography (ethyl acetate/petrol ether 1/5-1/1) to afford ethyl 2-((1H-pyrrolo[2,3-b]pyridin-5-yl)oxy)-4-(4-((6-(4-chlorophenyl)spiro[3.5]non-6-en-7-yl) methyl)piperazin-1-yl)benzoate (1.3 g, 71%) as white solid. $^1$H NMR (400 MHz, $CDCl_3$) δ 9.98 (s, 1H), 8.20 (d, J=2.6 Hz, 1H), 7.91 (d, J=9.0 Hz, 1H), 7.51 (d, J=2.6 Hz, 1H), 7.38 (t, J=3.5 Hz, 1H), 7.28 (d, J=8.3 Hz, 2H), 6.97 (d, J=8.3 Hz, 2H), 6.62 (dd, J=9.0, 2.5 Hz, 1H), 6.45 (dd, J=3.5, 2.0 Hz, 1H), 6.32 (d, J=2.5 Hz, 1H), 4.26 (q, J=7.1 Hz, 2H), 3.20-3.12 (m, 4H), 2.77 (s, 2H), 2.31-2.17 (m, 8H), 1.98-1.72 (m, 6H), 1.68 (t, J=6.3 Hz, 2H), 1.25 (t, J=7.1 Hz, 3H).

Intermediate 19

Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid

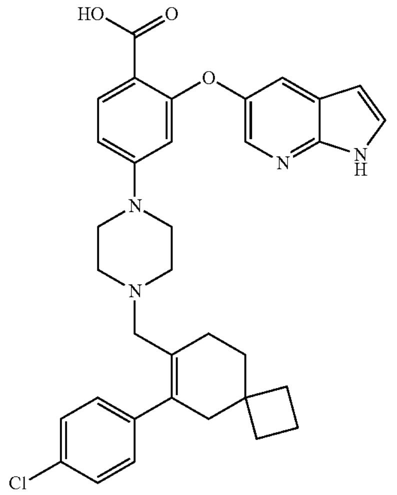

The solution of ethyl 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoate (1.3 g, 2.1 mmol) and 2N potassium hydroxide (12 mL, 0.042 mol) in dioxane (15 mL) was heated to 60° C. overnight. The mixture was neutralized with 1N aqueous hydrochloric acid to pH 7 and extracted with ethyl acetate (50 mL×3). The combined organic layers were washed with brine, dried over magnesium sulfate, and concentrated to afford 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid (1.1 g, 88.7%) as a white solid. $^1$H NMR (400 MHz, $CDCl_3$) δ 10.34 (s, 1H), 8.19 (d, J=2.6 Hz, 1H), 8.02 (d, J=9.0 Hz, 1H), 7.63 (d, J=2.6 Hz, 1H), 7.38-7.34 (m, 1H), 7.27 (d, J=8.3 Hz, 2H), 6.96 (d, J=8.3 Hz, 2H), 6.63 (dd, J=9.0, 2.4 Hz, 1H), 6.44 (dd, J=3.5, 1.5 Hz, 1H), 6.22 (d, J=2.4 Hz, 1H), 3.81 (s, 2H), 3.17-3.10 (m, 4H), 2.80 (s, 2H), 2.30-2.20 (m, 6H), 1.98-1.72 (m, 6H), 1.67 (t, J=6.3 Hz, 2H).

Intermediate 20

Synthesis of 1-(Oxetan-3-ylidene)propan-2-one

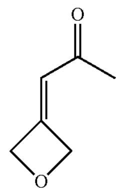

To a solution of oxetan-3-one (20.6 g, 0.28 mol) in DCM (300 ml) was added 1-(triphenylphosphoranylidene)propan-2-one (98.6 g, 0.31 mol). The mixture was stirred at room temperature overnight. DCM was removed under reduced pressure until solid was precipitated. The solid was removed by filtration and the filtrate was concentrated and purified by silica gel column chromatography (ethyl acetate/heptane 1/5~1/3) to afford 1-(oxetan-3-ylidene)propan-2-one (23.3 g, 74.3%) as a yellow oil.

Intermediate 21

Synthesis of 2-Oxaspiro[3.5]nonane-6,8-dione

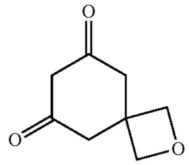 [SMILES: O=C1CC(=O)CC2(COC2)C1]

To a solution of 1-(oxetan-3-ylidene)propan-2-one (23.3 g, 0.21 mol) and methyl malonate (30.2 g, 0.23 mol) in methanol (150 ml) was added sodium methoxide (41.3 g, 30% MeOH solution). The mixture was heated to reflux under nitrogen for 1 h. Solvent was removed under reduced pressure to afford methyl 6-hydroxy-8-oxo-2-oxaspiro[3.5]non-6-ene-5-carboxylate which was used in the next step directly without purification. To an aqueous solution of KOH (2 mol/L, 200 ml) was added methyl 6-hydroxy-8-oxo-2-oxaspiro[3.5]non-6-ene-5-carboxylate. After stirring at room temperature for 30 min, the aqueous solution was extracted with ethyl acetate (150 ml×3). The aqueous layer was adjusted to pH 3-5 with 1 N hydrochloric acid and heated at 50° C. for 4 h. Water was removed under reduced pressure and the residue was purified by silica gel column chromatography to afford 2-oxaspiro[3.5]nonane-6,8-dione (2.5 g, 77.0%) as light yellow solid. This product was used directly in the next step without further purification.

Intermediate 22

Synthesis of 8-isobutoxy-2-oxaspiro[3.5]non-7-en-6-one

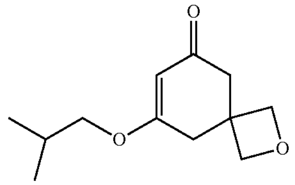

To a solution of 2-oxaspiro[3.5]nonane-6,8-dione (25 g, 0.16 mol) in toluene (150 ml) were added TsOH (238 mg, 0.0016 mol) and isobutyl alcohol (18 g, 0.24 mol). The reaction was completed after stirring at room temperature for 1 h. Solvent was removed under reduced pressure and the residue was purified by silica gel column chromatography (ethyl acetate/petrol ether 1/5~1/3) to afford 8-isobutoxy-2-oxaspiro[3.5]non-7-en-6-one (6 g, 43%) as light yellow oil. $^1H$ NMR (400 MHz, $CDCl_3$) δ 5.34 (s, 1H), 4.47 (d, J=6.1 Hz, 2H), 4.45 (d, J=6.1 Hz, 2H), 3.60 (d, J=6.8 Hz 2H), 2.80 (s, 2H), 2.68 (s, 2H), 2.09-2.01 (m, 1H), 0.98 (d, J=6.8 Hz, 6H).

Intermediate 23

Synthesis of 2-Oxaspiro[3.5]non-7-en-6-one

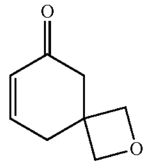

To a solution of 8-isobutoxy-2-oxaspiro[3.5]non-7-en-6-one (14.7 g, 0.07 mol) in toluene (100 ml) was added Red-Al® (40.4 g, 70% in Toluene) dropwise. The mixture was heated to 45° C. for 2 h and quenched by 1 N HCl solution. The mixture was concentrated and purified by silica gel column chromatography (ethyl acetate/petrol ether 1/10~1/5) to afford 2-oxaspiro[3.5]non-7-en-6-one (8.8 g, 91%) as colorless oil. This product was used directly in the next step without further purification.

Intermediate 24

Synthesis of 2-Oxaspiro[3.5]nonan-6-one

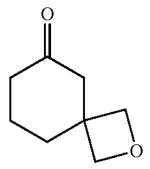

To a solution of 2-oxaspiro[3.5]non-7-en-6-one (8.8 g) in tetrahydrofuran (80 ml) was added Pd/C (1 g). The mixture was hydrogenated under 1 atm hydrogen at room temperature for 2 h. After the reaction was completed, Pd/C was removed by filtration and the solution was concentrated to afford 2-oxaspiro[3.5]nonan-6-one (8.0 g, 89.6%) as colorless oil. This product was used directly in the next step without further purification.

Intermediate 25

Synthesis of Methyl 6-oxo-2-oxaspiro[3.5]nonane-7-carboxylate

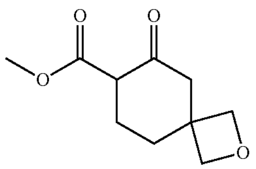

To a suspension of sodium hydride (4.6 g, 0.11 mol) in tetrahydrofuran (150 ml) under nitrogen was added methyl carbonate (25.7 g, 0.28 mol) dropwise. After dropping was completed, the mixture was heated to reflux. A solution of 2-oxaspiro[3.5]nonan-6-one (11.2 g, 0.057 mol) in tetrahydrofuran (30 ml) was then added. The reaction was heated at reflux for 2 h and quenched by saturated aqueous ammonium chloride, and extracted with ethyl acetate (100 ml×3). The combined organic layer was washed with brine, concentrated under reduced pressure and the residue was purified by silica gel column chromatography to afford methyl 6-oxo-2-oxaspiro[3.5]nonane-7-carboxylate (4.5 g, 69%) as colorless oil. This product was used directly in the next step without further purification.

Intermediate 26

Synthesis of Methyl 6-(((trifluoromethyl)sulfonyl)oxy)-2-oxaspiro[3.5]non-6-ene-7-carboxylate

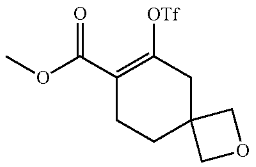 [SMILES: COC(=O)C1=C(OS(=O)(=O)C(F)(F)F)CC2(CC1)COC2]

To a suspension of methyl 6-oxo-2-oxaspiro[3.5]nonane-7-carboxylate (4.5 g, 0.02 mol) and potassium carbonate (6.3 g, 0.046 mol) in DMF (30 ml) was added N,N-bis(trifluoromethylsulfonyl)aniline (8.9 g, 0.025 mol). The mixture was stirred at room temperature overnight, diluted with water, and extracted with ethyl acetate (100 ml×3). The combined organic layer was washed with brine, dried over MgSO4, and concentrated under reduced pressure. The residue was purified by silica gel column chromatography (ethyl acetate/Petrol ether 1/10~1/3) to afford methyl 6-(((trifluoromethyl)sulfonyl)oxy)-2-oxaspiro[3.5]non-6-ene-7-carboxylate (6.6 g, 86%) as light yellow oil. This product was used directly in the next step without further purification.

Intermediate 27

Synthesis of Methyl 6-(4-chlorophenyl)-2-oxaspiro[3.5]non-6-ene-7-carboxylate

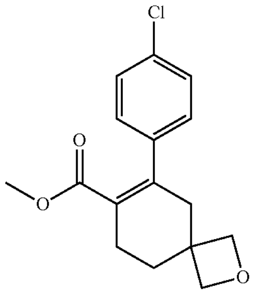 [SMILES: COC(=O)C1=C(c2ccc(Cl)cc2)CC2(CC1)COC2]

To a solution of methyl 6-(((trifluoromethyl)sulfonyl)oxy)-2-oxaspiro[3.5]non-6-ene-7-carboxylate (6.6 g, 0.02 mol) in 1,2-dimethoxy-ethan (30 ml) and methanol (10 ml) were added 4-chloro-phenyl boronic acid (3.13 g, 0.02 mol), CsF (6.08 g, 0.04 mol) and $Pd(PPh_3)_4$ (231 mg, 0.2 mmol) and the mixture was heated to 70° C. under nitrogen for 30 min. Solvents were removed under reduced pressure and the residue was purified by silica gel column chromatography (ethyl acetate/petrol ether 1/5-1/3) to afford methyl 6-(4-chlorophenyl)-2-oxaspiro[3.5]non-6-ene-7-carboxylate (5.1 g, 87.3%) as light yellow solid. $^1$H NMR (400 MHz, $CDCl_3$) δ 7.33 (d, J=8.4 Hz, 2H), 7.07 (d, J=8.4 Hz, 2H), 4.54 (d, J=5.6 Hz, 2H), 4.48 (d, J=5.6 Hz, 2H), 3.48 (s, 3H), 2.74-2.70 (m, 2H), 2.55-2.50 (m, 2H), 2.04 (t, J=6.4 Hz, 2H).

Intermediate 28

Synthesis of (6-(4-Chlorophenyl)-2-oxaspiro[3.5]non-6-en-7-yl)methanol

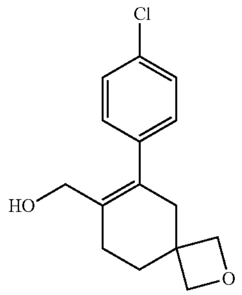 [SMILES: OCC1=C(c2ccc(Cl)cc2)CC2(CC1)COC2]

To a solution of methyl 6-(4-chlorophenyl)-2-oxaspiro[3.5]non-6-ene-7-carboxylate (2.1 g, 0.0072 mol) in tetrahydrofuran (20 ml) was added $LiBH_4$ (475 mg, 0.022 mol) in tetrahydrofuran (10 ml) dropwise at room temperature. The mixture was stirred at room temperature for 4 h, quenched by 1 N HCl solution, and extracted with ethyl acetate (100 ml×3). The combined organic layers were washed with brine, dried over $MgSO_4$ and concentrated. The residue was purified by silica gel column chromatography (ethyl acetate/petrol ether 1/5-1/1) to afford (6-(4-chlorophenyl)-2-oxaspiro[3.5]non-6-en-7-yl)methanol (1.5 g, 78.9%) as white solid. $^1$H NMR (400 MHz, $CDCl_3$) δ 7.34

(d, J=8.4 Hz, 2H), 7.07 (d, 2H, J=8.4 Hz), 4.54 (d, 2H, J=6.0 Hz), 4.46 (d, 2H, J=5.6 Hz), 3.93 (s, 2H), 2.62 (s, 2H), 2.40-2.33 (m, 2H), 2.03 (t, 2H, J=6.4 Hz).

Intermediate 29

Synthesis of 7-(Chloromethyl)-6-(4-chlorophenyl)-2-oxaspiro[3.5]non-6-ene

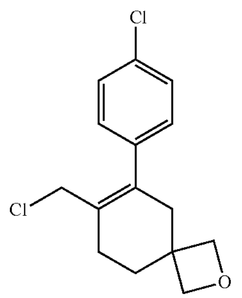 [SMILES: ClCC1=C(c2ccc(Cl)cc2)CC2(CC1)COC2]

To a solution of (6-(4-chlorophenyl)-2-oxaspiro[3.5]non-6-en-7-yl)methanol (1.5 g, 5.7 mmol) and triethylamine (836 mg, 8.6 mmol) in dichloromethane (15 ml) was added methylsulfonyl chloride
(980 mg, 8.6 mmol) and the mixture was stirred at room temperature for 3.5 h. Solvent was removed under reduced pressure and the residue was purified by silica gel column chromatography to afford 7-(chloromethyl)-6-(4-chlorophenyl)-2-oxaspiro[3.5]non-6-ene (1.4 g, 87.0%) as white solid. $^{1}$H NMR (400 MHz, $CDCl_3$) δ 7.35 (d, 2H, J=8.4 Hz), 7.16 (d, 2H, J=8.4 Hz), 4.53 (d, 2H, J=6.0 Hz), 4.45 (d, 2H, J=5.6 Hz), 3.86 (s, 2H), 2.64 (s, 2H), 2.40-2.33 (m, 2H), 2.03 (t, 2H, J=6.4 Hz).

Intermediate 30

Synthesis of Ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate

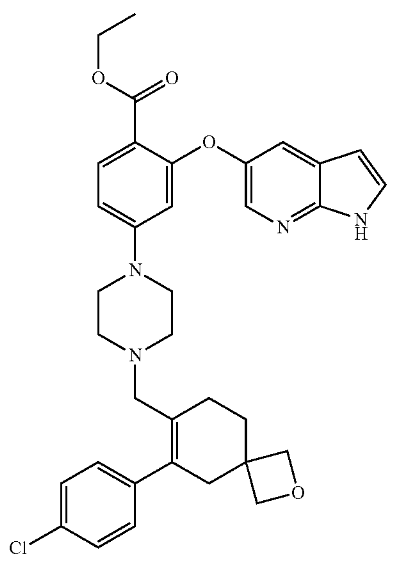 [SMILES: CCOC(=O)c1ccc(N2CCN(CC3=C(c4ccc(Cl)cc4)CC4(CC3)COC4)CC2)cc1Oc1cnc2[nH]ccc2c1]

To a solution of ethyl 2-((1H-pyrrolo[2,3-b]pyridin-5-yl)oxy)-4-(piperazin-1-yl)benzoate (382 mg, 0.82 mmol) in DMF (10 ml) were added 7-(chloromethyl)-6-(4-chlorophenyl)-2-oxaspiro[3.5]non-6-ene (200 mg, 0.75 mmol), potassium carbonate (310 mg, 2.25 mmol), DIPEA (290 mg, 2.25 mmol) and potassium iodide (24.9 mg, 0.15 mmol) and the mixture was stirred at room temperature overnight. The mixture was diluted with water and extracted with ethyl acetate (50 ml×3). The combined organic layers were washed with brine, concentrated and purified by silica gel column chromatography (ethyl acetate/petrol ether 1/5-1/1) to afford ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate (370 mg, 80.6%) as white solid. MS m/z 613 $[M+H]^+$.

Intermediate 31

Synthesis of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid

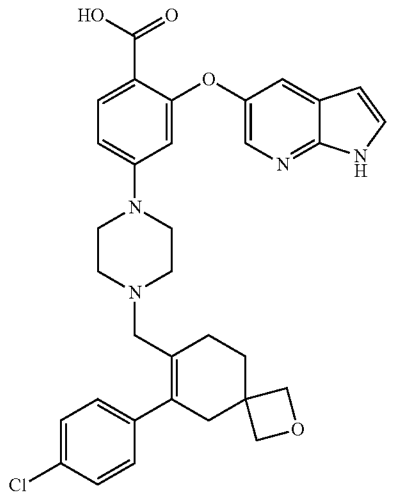 [SMILES: O=C(O)c1ccc(N2CCN(CC3=C(c4ccc(Cl)cc4)CC4(CC3)COC4)CC2)cc1Oc1cnc2[nH]ccc2c1]

To a solution of ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate (370 mg, 0.6 mmol) in dioxane (10 ml) was added 2N potassium hydroxide (6 ml, 12 mmol) and the mixture was stirred at 60° C. overnight. The solution was neutralized with 1N hydrochloric acid to pH 7 and extracted with ethyl acetate (100 ml×3). The combined organic layers were washed with brine, dried over magnesium sulfate and concentrated to afford 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (1.1 g, 88.7%) as white solid. MS m/z 585 $[M+H]^+$.

Intermediate 32

Synthesis of Methyl 2-((1H-pyrrolo[2,3-b]pyridin-5-yl)oxy)-4-(1-((6-(4-chlorophenyl)spiro[3.5]non-6-en-7-yl) methyl)piperidin-4-yl)benzoate

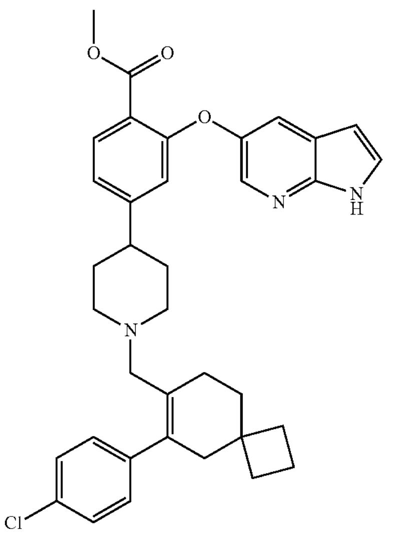 [SMILES: COC(=O)c1ccc(C2CCN(CC3=C(c4ccc(Cl)cc4)CC4(CCC4)CC3)CC2)cc1Oc1cnc2[nH]ccc2c1]

To as solution of 7-(chloromethyl)-6-(4-chlorophenyl) spiro[3.5]non-6-ene (850 mg, 3.04 mmol) in N,N-dimethyl formamide (10 ml) were added potassium carbonate (1.26 g, 2.2 mmol), potassium iodide (100 mg, 0.61 mmol), and methyl 2-((1H-pyrrolo[2,3-b]pyridin-5-yl)oxy)-4-(piperidin-4-yl)benzoate (1.0 g, 3.34 mmol) the mixture was stirred at room temperature overnight. Then the mixture was diluted with water and extracted with ethyl acetate. The combined organic layers were washed with brine and concentrated. The resulting residue was purified by silica gel column chromatography to afford methyl 2-((1H-pyrrolo[2,3-b]pyridin-5-yl)oxy)-4-(1-((6-(4-chlorophenyl)spiro[3.5]non-6-en-7-yl)methyl)piperidin-4-yl)benzoate (1.0 g, 55.2%) as light yellow solid. 1H NMR (400 MHz, $CDCl_3$) δ 9.39 (br s, 1H), 8.19 (d, J=2.6 Hz, 1H), 7.87 (d, J=8.1 Hz, 1H), 7.57 (d, J=2.6 Hz, 1H), 7.39 (dd, J=3.5, 2.5 Hz, 1H), 7.30-7.23 (m, 2H), 7.04-6.93 (m, 3H), 6.72 (d, J=1.6 Hz, 1H), 6.49 (dd, J=3.5, 2.0 Hz, 1H), 3.87 (s, 3H), 2.81-2.75 (m, 2H), 2.73-2.71 (m, 2H), 2.28 (s, 2H), 2.25-2.15 (m, 2H), 1.98-1.76 (m, 6H), 1.75-1.51 (m, 9H).

Example 2—Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide (Compound 2)

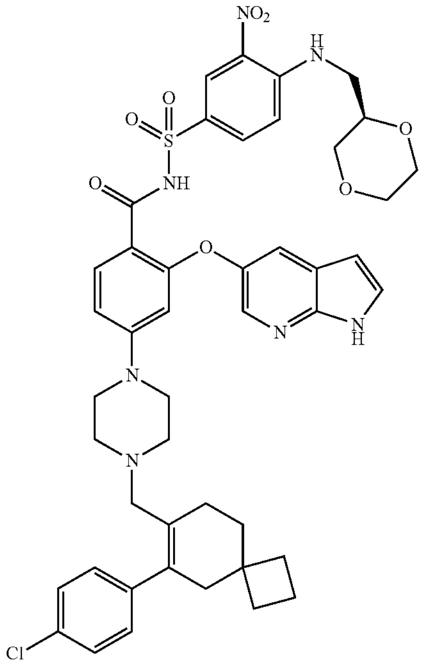 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid, (R)-4-(((1,4-dioxan-2-yl)methyl) amino)-3-nitrobenzenesulfonamide, EDCI and 4-(N,N-dimethylamino)pyridine and dichloromethane was reacted at room temperature overnight, followed by the addition of water. The water layer was extracted with dichloromethane. The combined organic layers were washed with brine, concentrated and purified through silica gel chromatography to afford (R)—N-((4-(((1,4-dioxan-2-yl)methyl)amino)-3-nitrophenyl)sulfonyl)-2-((1H-pyrrolo[2,3-b]pyridin-5-yl) oxy)-4-(4-((6-(4-chlorophenyl)spiro[3.5]non-6-en-7-yl) methyl)piperazin-1-yl)benzamide. $^1$H NMR (400 MHz, Methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Example 3—Synthesis of (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide (Compound 1)

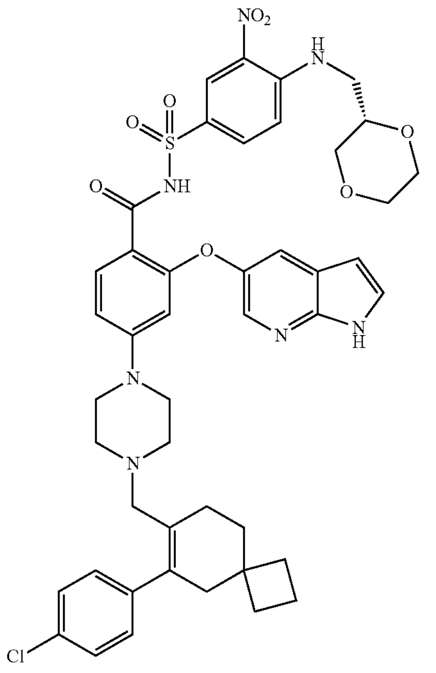 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid, (S)-4-(((1,4-dioxan-2-yl)methyl)amino)-3-nitrobenzenesulfonamide, EDCI and 4-(N,N-dimethylamino)pyridine and dichloromethane was reacted at room temperature overnight, followed by the addition of water. The water layer was extracted with dichloromethane. The combined organic layers were washed with brine, concentrated and purified through silica gel chromatography to afford (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide. $^1$H NMR (400 MHz, Methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Example 4—Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide

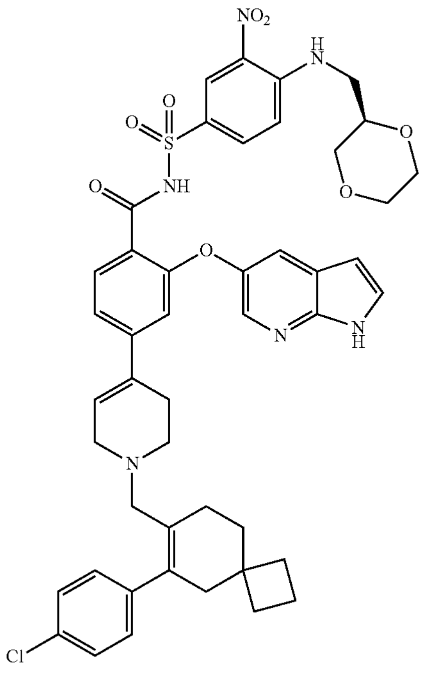 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1]

To a solution of (R)—N-((4-(((1,4-dioxan-2-yl)methyl)amino)-3-nitrophenyl)sulfonyl)-2-((1H-pyrrolo[2,3-b]pyridin-5-yl)oxy)-4-bromobenzamide in 1,2-dimethoxy-ethane (10 ml) and water (1 ml) were added 1-((6-(4-chlorophenyl)spiro[3.5]non-6-en-7-yl)methyl)-4-(4,4,5,5-tetramethyl-1,3,2-dioxaborolan-2-yl)-1,2,3,6-tetrahydropyridine, Pd(dppf)$Cl_2$, and $K_2CO_3$, and the mixture was stirred at 80° C. for 12 h. The reaction was cooled to room temperature and diluted with water. The mixture was extracted with ethyl acetate (30 ml×3), dried over anhydrous $MgSO_4$, and concentrated. The residue was purified by $C_{18}$ reversed phase preparative HPLC to give (R)—N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide. $^1$H NMR (400 MHz, Methanol-$d_4$) δ 8.68 (d, J=2.3 Hz, 1H), 7.97 (d, J=2.6 Hz, 1H), 7.88 (dd, J=9.3, 2.3 Hz, 1H), 7.63 (d, J=8.2 Hz, 1H), 7.50 (d, J=2.6 Hz, 1H), 7.46 (d, J=3.5 Hz, 1H), 7.30 (d, J=8.4 Hz, 2H), 7.16 (dd, J=8.2, 1.7 Hz, 1H), 7.10 (d, J=8.4 Hz, 2H), 6.94 (d, J=9.3 Hz, 1H), 6.85 (d, J=1.7 Hz, 1H), 6.41 (d, J=3.5 Hz, 1H), 5.94-5.90 (m, 1H), 3.95-3.40 (m, 14H), 3.15-3.03 (m, 1H), 2.68-2.45 (m, 2H), 2.43 (s, 2H), 2.30-2.20 (m, 2H), 2.03-1.77 (m, 8H).

Example 5—Synthesis of 2-((1H-pyrrolo[2,3-b]pyridin-5-yl)oxy)-4-(1-((6-(4-chlorophenyl)-2-oxaspiro [3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide

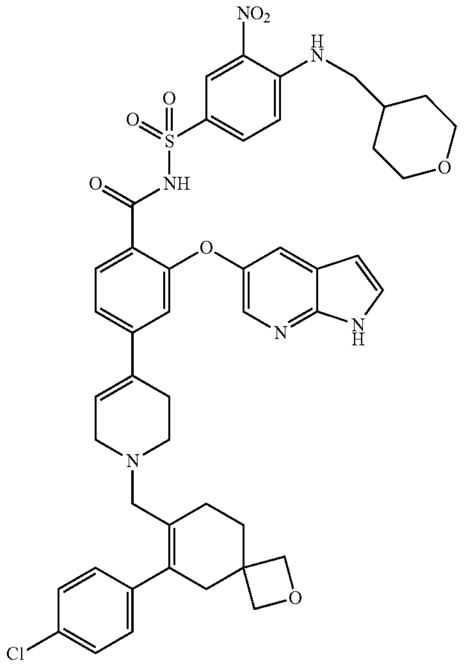 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1]

The title compound was prepared using a procedure similar to the one described for EXAMPLE 4. $^{1}$H NMR (400 MHz, Methanol-$d_4$) δ 8.70 (d, J=2.3 Hz, 1H), 7.99 (d, J=2.5 Hz, 1H), 7.90 (dd, J=9.2, 2.3 Hz, 1H), 7.61 (d, J=8.2 Hz, 1H), 7.57 (d, J=2.5 Hz, 1H), 7.48 (d, J=3.5 Hz, 1H), 7.31 (d, J=8.4 Hz, 2H), 7.20-7.10 (m, 3H), 6.96 (d, J=9.2 Hz, 1H), 6.82 (d, J=1.6 Hz, 1H), 6.44 (d, J=3.5 Hz, 1H), 5.93-5.86 (m, 1H), 4.53 (d, J=5.9 Hz, 2H), 4.49 (d, J=5.9 Hz, 2H), 4.00-3.90 (m, 2H), 3.77-3.33 (m, 7H), 3.26 (d, J=7.0 Hz, 2H), 3.15-3.00 (m, 1H), 2.70-2.65 (m, 2H), 2.63-2.25 (m, 4H), 2.07 (t, J=6.3 Hz, 2H), 2.00-1.85 (m, 1H), 1.75-1.65 (m, 2H), 1.46-1.30 (m, 2H).

Example 6—Synthesis of 2-((1H-pyrrolo[2,3-b]pyridin-5-yl)oxy)-4-(1-((6-(4-chlorophenyl)spiro [3.5]non-6-en-7-yl)methyl)-1,2,3,6-tetrahydropyridin-4-yl)-N-((3-nitro-4-(((tetrahydro-2H-pyran-4-yl) methyl)amino)phenyl)sulfonyl)benzamide

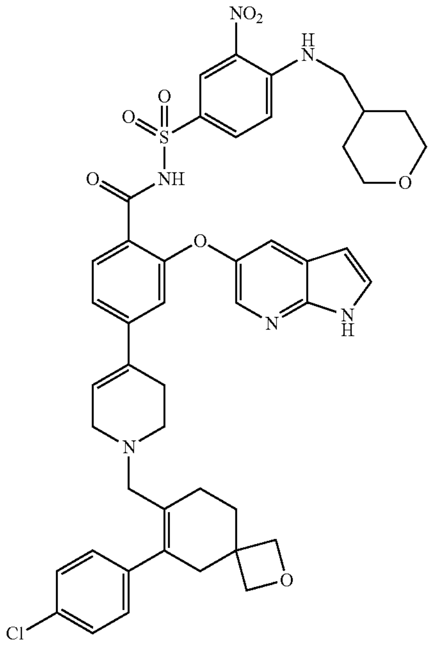 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1]

The title compound was prepared using a procedure similar to the one described for EXAMPLE 4. $^{1}$H NMR (400 MHz, Methanol-$d_4$) δ 8.71 (t, J=1.9 Hz, 1H), 8.00-7.95 (m, 1H), 7.90 (dd, J=9.3, 1.9 Hz, 1H), 7.63 (dd, J=8.1, 1.4 Hz, 1H), 7.56-7.50 (m, 1H), 7.46 (dd, J=3.5, 1.4 Hz, 1H), 7.33-7.26 (m, 2H), 7.18-7.06 (m, 3H), 6.96 (dd, J=9.3, 1.4 Hz, 1H), 6.81 (s, 1H), 6.43 (dd, J=3.5, 1.5 Hz, 1H), 5.93-5.86 (m, 1H), 4.00-3.94 (m, 2H), 3.83-3.36 (m, 7H), 3.26 (d, J=7.0 Hz, 2H), 3.10-3.04 (m, 1H), 2.67-2.40 (m, 4H), 2.30-2.24 (m, 2H), 2.02-1.77 (m, 9H), 1.74-1.67 (m, 2H), 1.45-1.30 (m, 2H).

Example 7—Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chloro-phenyl)-2-oxaspiro[3.5]non-6-en-7-yl)methyl)-1,2,3,6-tetrahydropyridin-4-yl)benzamide

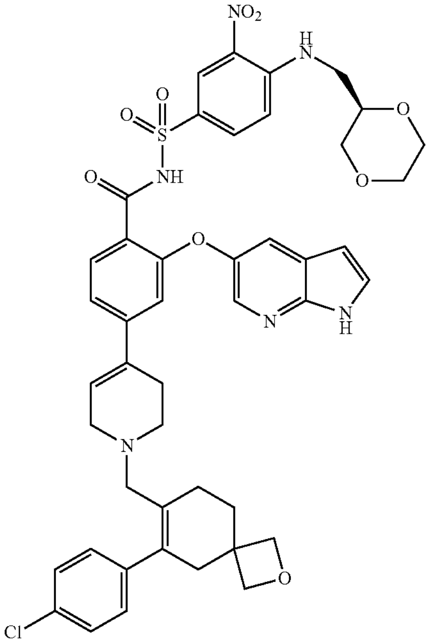 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1]

The title compound was prepared using a procedure similar to the one described for EXAMPLE 4. $^1$H NMR (400 MHz, Methanol-$d_4$) δ 8.68 (d, J=2.3 Hz, 1H), 7.99 (d, J=2.5 Hz, 1H), 7.89 (dd, J=9.2, 2.3 Hz, 1H), 7.65 (d, J=8.2 Hz, 1H), 7.54 (d, J=2.5 Hz, 1H), 7.48 (d, J=3.4 Hz, 1H), 7.33 (d, J=8.4 Hz, 2H), 7.21-7.16 (m, 1H), 7.13 (d, J=8.4 Hz, 2H), 6.95 (d, J=9.3 Hz, 1H), 6.86 (d, J=1.6 Hz, 1H), 6.43 (d, J=3.5 Hz, 1H), 5.94-5.90 (m, 1H), 4.60-4.43 (m, 4H), 3.95-3.40 (m, 14H), 3.15-3.00 (m, 1H), 2.80-2.60 (m, 4H), 2.38-2.25 (m, 2H), 2.08 (t, J=6.3 Hz, 2H).

Example 8—Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chloro-phenyl)-2-oxaspiro[3.5]non-6-en-7-yl)methyl)piperazin-1-yl)benzamide

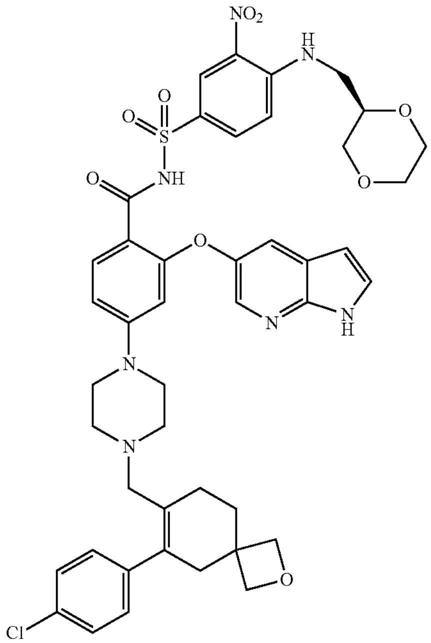 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CC3)COC4)CC2)cc1Oc1cnc2[nH]ccc2c1]

A mixture of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (290 mg, 0.5 mmol), (R)-4-(((1,4-dioxan-2-yl)methyl)amino)-3-nitrobenzene-sulfonamide (236 mg, 0.75 mmol), EDCI (191 mg, 1 mmol), 4-(N,N-dimethylamino)pyridine (591 mg, 0.75 mmol) in dichloromethane (15 ml) was stirred at room temperature overnight. The solvent was removed under vacuum and the resulting residue was purified through a silica gel column to afford (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide (150 mg, 34.1%) as yellow solid. $^1$H NMR (400 MHz, Methanol-$d_4$) δ 8.67 (d, J=2.3 Hz, 1H), 7.99 (d, J=2.3 Hz, 1H), 7.85 (dd, J=9.3, 2.3 Hz, 1H), 7.64 (d, J=8.8 Hz, 1H), 7.52 (d, J=2.3 Hz, 1H), 7.45 (d, J=3.5 Hz, 1H), 7.39 (d, J=8.4 Hz, 2H), 7.13 (d, J=8.4 Hz, 2H), 6.95 (d, J=9.3 Hz, 1H), 6.76 (dd, J=8.8, 2.4 Hz, 1H), 6.41 (d, J=3.5 Hz, 1H), 6.34 (d, J=2.4 Hz, 1H), 4.54 (d, J=5.9 Hz, 2H), 4.48 (d, J=5.9 Hz, 2H), 3.93-3.35 (m, 19H), 2.70-2.65 (m, 2H), 2.33 (s, 2H), 2.08 (t, J=6.3 Hz, 2H).

Example 9—Synthesis of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide

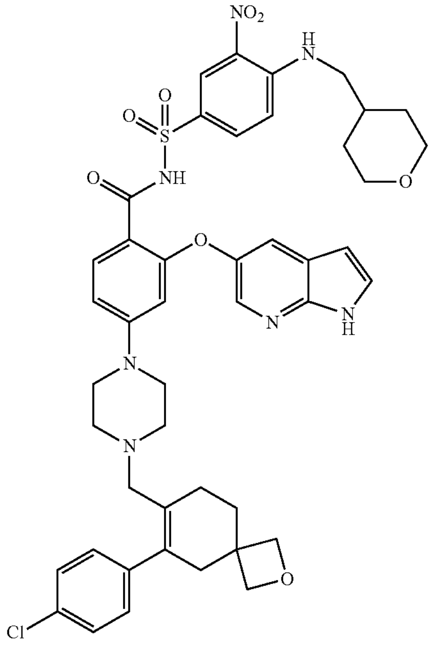 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1]

A mixture of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (250 mg, 0.43 mmol), 3-nitro-4-(((tetrahydro-2H-pyran-4-yl)methyl)amino)benzenesulfonamide (202 mg, 0.64 mmol), EDCI (164 mg, 0.86 mmol), 4-(N,N-dimethylamino)pyridine (78 mg, 0.64 mmol) in dichloromethane (10 ml) was stirred at room temperature overnight, followed by concentration. The resulting residue was purified through silica gel chromatography to afford 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide (150 mg, 39.6%) as a yellow solid. $^1H$ NMR (400 MHz, Methanol-$d_4$) δ 8.70 (d, J=2.3 Hz, 1H), 8.01 (d, J=2.6 Hz, 1H), 7.87 (dd, J=9.2, 2.3 Hz, 1H), 7.66 (d, J=8.8 Hz, 1H), 7.56 (d, J=2.6 Hz, 1H), 7.47 (d, J=3.5 Hz, 1H), 7.39 (d, J=8.4 Hz, 2H), 7.13 (d, J=8.4 Hz, 2H), 6.97 (d, J=9.2 Hz, 1H), 6.76 (dd, J=8.8, 2.4 Hz, 1H), 6.43 (d, J=3.5 Hz, 1H), 6.32 (d, J=2.4 Hz, 1H), 4.54 (d, J=5.9 Hz, 2H), 4.48 (d, J=5.9 Hz, 2H), 4.03-3.94 (m, 2H), 3.67 (s, 2H), 3.55-3.27 (m, 12H), 2.69 (s, 2H), 2.35-2.25 (m, 2H), 2.08 (t, J=6.3 Hz, 2H), 2.05-1.93 (m, 1H), 1.76-1.69 (m, 2H), 1.45-1.35 (m, 2H).

Example 10—Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide

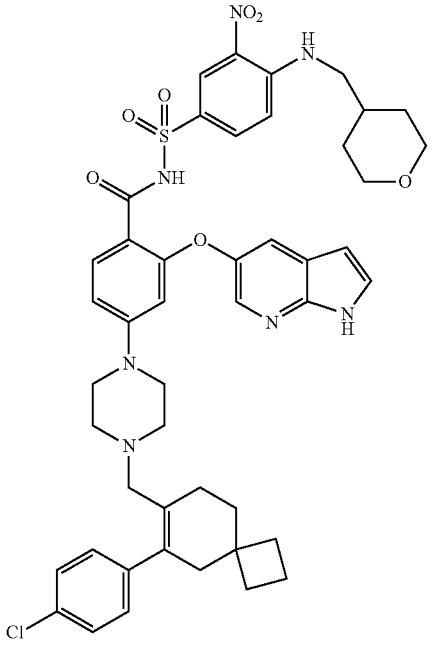 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid (1.75 g, 3 mmol), 3-nitro-4-(((tetrahydro-2H-pyran-4-yl)methyl)amino)benzenesulfonamide (1.43 g, 4.5 mmol), EDCI (1.15 g, 6 mmol) and 4-(N,N-dimethylamino)pyridine (550 mg, 4.5 mmol) and dichloromethane (40 ml) was reacted at room temperature overnight, followed by the addition of water. The water layer was extracted with dichloromethane. The combined organic layers were washed with brine, concentrated and purified through silica gel column to afford 2-((1H-pyrrolo[2,3-b]pyridin-5-yl)oxy)-4-(4-((6-(4-chlorophenyl)spiro[3.5]non-6-en-7-yl) methyl)piperazin-1-yl)-N-((3-nitro-4-(((tetrahydro-2H-pyran-4-yl)methyl)amino)phenyl)sulfonyl) benzamide (1.7 g, 64.4%) as a yellow solid. 1H NMR (400 MHz, Methanol-$d_4$) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

Example 11—Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((3-nitrophenyl)sulfonyl)benzamide

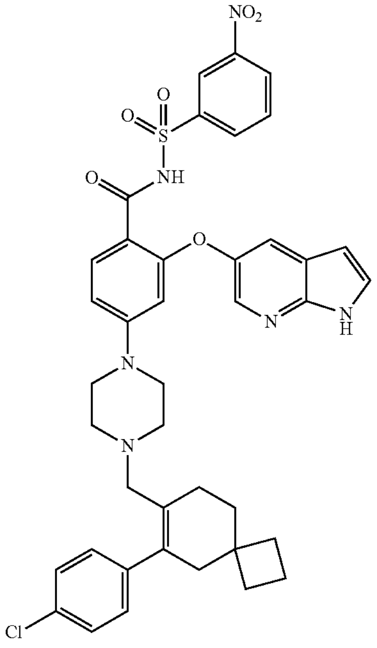 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1]

The title compound was prepared using a procedure similar to the one described for EXAMPLE 10. $^{1}$H NMR (400 MHz, DMSO-$d_6$) δ 11.70 (s, 1H), 9.47 (s, 1H), 8.62 (d, J=2.2 Hz, 1H), 8.44 (d, J=8.3 Hz, 1H), 8.27 (d, J=7.9 Hz, 1H), 8.02-7.97 (m, 1H), 7.84-7.75 (m, 1H), 7.56-7.43 (m, 3H), 7.40 (d, J=8.3 Hz, 2H), 7.11 (d, J=8.3 Hz, 2H), 6.72 (d, J=8.9 Hz, 1H), 6.40-6.35 (m, 1H), 6.30 (s, 1H), 3.80-3.65 (m, 2H), 3.55 (s, 2H), 3.28-2.95 (m, 4H), 2.82-2.65 (m, 2H), 2.31 (s, 2H), 2.22-2.15 (m, 2H), 1.93-1.60 (m, 8H).

Example 12—Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((4-(methylamino)-3-nitrophenyl)sulfonyl)benzamide

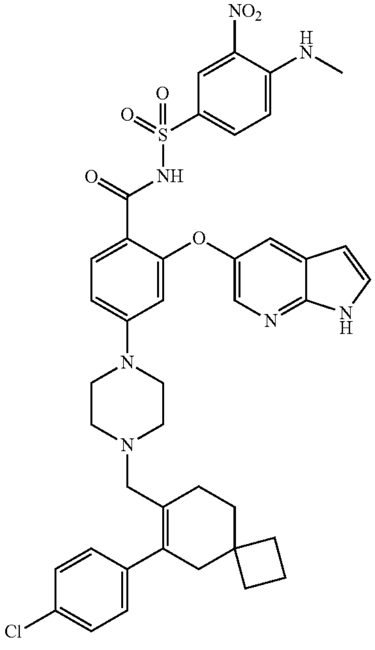 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]]

The title compound was prepared using a procedure similar to the one described for EXAMPLE 10. $^{1}$H NMR (400 MHz, Methanol-$d_4$) δ 8.78 (d, J=2.3 Hz, 1H), 8.05 (d, J=2.6 Hz, 1H), 7.96 (dd, J=9.2, 2.3 Hz, 1H), 7.80 (d, J=8.9 Hz, 1H), 7.61 (d, J=2.6 Hz, 1H), 7.46 (d, J=3.5 Hz, 1H), 7.34 (d, J=8.4 Hz, 2H), 7.01 (d, J=8.4 Hz, 2H), 6.90 (d, J=9.2 Hz, 1H), 6.68 (dd, J=8.9, 2.4 Hz, 1H), 6.46 (d, J=3.5 Hz, 1H), 6.18 (d, J=2.4 Hz, 1H), 3.60 (s, 2H), 3.50-3.12 (m, 8H), 3.06 (s, 3H), 2.38 (s, 2H), 2.30-2.16 (m, 2H), 1.97-1.73 (m, 8H).

Example 13—Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((4-(dimethylamino)-3-nitrophenyl) sulfonyl)benzamide

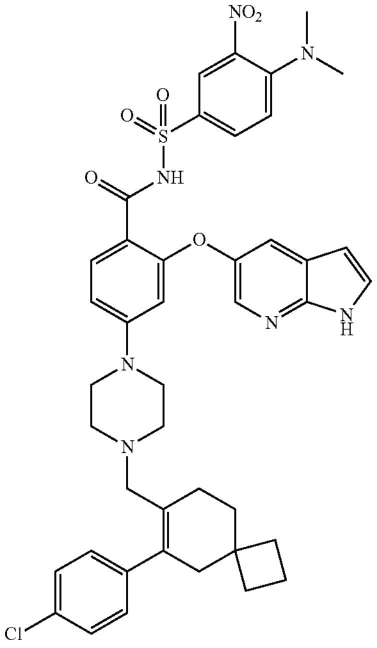 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]]

The title compound was prepared using a procedure similar to the one described for EXAMPLE 10. $^{1}$H NMR (400 MHz, Methanol-$d_4$) δ 8.41 (d, J=2.2 Hz, 1H), 8.08 (d, J=2.5 Hz, 1H), 7.91 (dd, J=9.4, 2.3 Hz, 1H), 7.81 (d, J=8.9 Hz, 1H), 7.68 (d, J=2.3 Hz, 1H), 7.48 (d, J=3.5 Hz, 1H), 7.34 (d, J=8.0 Hz, 2H), 7.04 (d, J=9.4 Hz, 1H), 7.01 (d, J=8.0 Hz, 2H), 6.71-6.63 (m, 1H), 6.51 (d, J=3.5 Hz, 1H), 6.15 (d, J=1.9 Hz, 1H), 3.59 (s, 2H), 3.52-3.20 (m, 8H), 2.98 (s, 6H), 2.38 (s, 2H), 2.25-2.17 (m, 2H), 1.96-1.72 (m, 8H).

Example 14—Synthesis of 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide

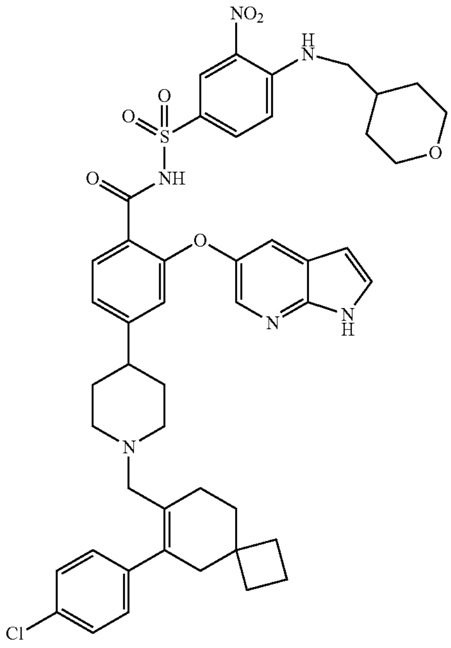 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(1-((6-(4-chlorophenyl)spiro[3.5]non-6-en-7-yl)methyl)piperidin-4-yl)benzoic acid (200 mg, 0.34 mmol), 3-nitro-4-(((tetrahydro-2H-pyran-4-yl)methyl)amino) benzenesulfonamide (162 mg, 0.52 mmol), EDCI (130 mg, 0.68 mmol), 4-(N,N-dimethylamino)pyridine (63.4 mg, 0.52 mmol) in dichloromethane (15 ml) was stirred at room temperature overnight, followed by purification by silica gel column chromatography to afford 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl) methyl)amino)phenyl)sulfonyl) benzamide (170 mg, 57.3%) as a yellow solid. $^{1}$H NMR (400 MHz, DMSO-$d_6$) δ 11.94 (s, 1H), 11.64 (s, 1H), 8.50-8.42 (m, 2H), 7.97 (d, J=2.6 Hz, 1H), 7.76 (dd, J=9.2, 2.2 Hz, 1H), 7.52-7.36 (m, 5H), 7.11 (d, J=7.9 Hz, 2H), 6.99 (d, J=9.2 Hz, 1H), 6.91-6.86 (m, 1H), 6.55 (s, 1H), 6.37 (s, 1H), 3.89-3.79 (m, 2H), 3.35-2.90 (m, 10H), 2.32-2.10 (m, 5H), 1.95-1.15 (m, 17H).

Example 15—Compounds of Formula (I) Inhibit Bcl-2 and Bcl-$X_L$

Fluorescein labeled BIM (81-106), BAK (72-87), and BID (79-99) peptides, named as Flu-BIM, Flu-BAK, and Flu-BID, respectively, were used as the fluorescent probes in FP assays for Bcl-2,
Bcl-$X_L$, and Mcl-1, respectively. By monitoring the total fluorescence polarization values of mixtures composed of fluorescent probes at fixed concentrations and proteins with increasing concentrations up to the full saturation, the $K_d$ values of Flu-BIM to Bcl-2, Flu-BAK to Bcl-$X_L$ and Flu-BID to Mcl-1 were determined to be 0.55±0.15 nM, 4.4±0.8 nM, and 6.9±0.9 nM, respectively. Fluorescence polarization values were measured using an Infinite M-1000 plate reader (Tecan U.S., Research Triangle Park, N.C.) in Microfluor 96-well, black, round-bottom plates (Thermo Scientific). To each well, 1 nM of Flu-BIM, or 2 nM of Flu-BAK or 2 nM of Flu-BID and increasing concentrations of Bcl-2, or Bcl-$X_L$, or Mcl-1 were added to a final volume of 125 μL in the assay buffer (100 mM potassium phosphate, pH 7.5, 100 μg/mL bovine γ-globulin, 0.02% sodium azide, Invitrogen, with 0.01% Triton X-100 and 4% DMSO). Plates were mixed and incubated at room temperature for 1 hour with gentle shaking to assure equilibrium. The polarization values in millipolarization units (mP) were measured at an excitation wavelength of 485 nm and an emission wavelength of 530 nm. Equilibrium dissociation constants ($K_d$) were then calculated by fitting the sigmoidal dose-dependent FP increases as a function of protein concentrations using Graphpad Prism 5.0 software (Graphpad Software, San Diego, Calif.).

$K_i$ values of representative compounds of the disclosure to Bcl-2, Bcl-$X_L$, and Mcl-1 were determined from competitive binding experiments in which serial dilutions of inhibitors were added into 96-well plates containing fixed concentration of the fluorescent probes and proteins in each well. Mixtures of 5 μL of the tested inhibitors in DMSO and 120 μL of pre-incubated protein/probe complexes in the assay buffer were added into assay plates and incubated at room temperature for 2 hours with gentle shaking. Final concentrations of the protein and probe are 1.5 nM and 1 nM for the Bcl-2 assay, 10 nM and 2 nM for the Bcl-xL assay, and 20 nM and 2 nM for Mcl-1 assay, respectively. Negative controls containing protein/probe complex only (equivalent to 0% inhibition), and positive controls containing free probe only (equivalent to 100% inhibition), were included in each assay plate. Fluorescence polarization values were measured as described above. $IC_{50}$ values were determined by nonlinear regression fitting of the competition curves. The $K_i$ values of competitive inhibitors were calculated using an equation described in Nikolovska-Coleska et al., *Analytical Biochemistry* 332:261-73 (2004), based upon the measured $IC_{50}$ values, the values of the probes to the proteins, and the concentrations of the proteins and probes in the competitive assays. $K_d$ values were also calculated using the equation of Huang, *Journal of Biomolecular Screening* 8:34-38 (2003).

The inhibitory activities of representative Compounds of the Disclosure against Bcl-2, Bcl-xL, and Mcl-1 are provided in Table 2.

TABLE 2

| | Inhibitory Activity $IC_{50}$ (nM) | | |
|---|---|---|---|
| Cpd. No. | Bcl-2 | Bcl-$X_L$ | Mcl-1 |
| 1 | 2.0 | 15.7 | >5000 |
| 2 | 1.3 | 14.8 | |
| 3 | 1.4 | 9.2 | |
| 4 | 0.76 | 10.6 | |
| 5 | 1.2 | 13.7 | |
| 6 | 3.1 | 8.6 | |
| 7 | 2.1 | 14 | |
| 8 | 2.4 | 15.7 | |
| 9 | 2.4 | 6.4 | >5000 |
| 10 | 1.9 | 20.6 | |
| 11 | 3.3 | 14.0 | |
| 12 | 11.9 | 77.8 | |
| 13 | 4.4 | 139 | |
| 14 | 3.8 | 19.2 | |
| 15 | 5.0 | 20.7 | |
| 16 | 2.1 | 67.5 | |
| 17 | 2.1 | 13.1 | |
| 18 | 1.3 | 7.1 | |
| 19 | 1.4 | 9.9 | |
| 20 | 2.7 | 12.0 | |

Example 16—MRL/lpr Mouse Model of SLE

Female MRL/MpJ-Fas lpr/J mice (18-20 g, 7-8 weeks old) were obtained from The Jackson Laboratory. These mice are homozygous for the lymphoproliferation spontaneous mutation ($Fas^{lpr}$), and show systemic autoimmunity, massive lymphadenopathy associated with proliferation of aberrant T cells, arthritis, and immune complex glomerulonephrosis. Thus, these mice are useful as a model in the study of of systemic lupus erythematosus (SLE).

Animals were housed and handled in a temperature-controlled environment with a 12-h light/12-h dark cycle. A total of 36 mice were assigned to 3 groups by randomization, based on urine protein concentrations and body weight, followed by 10 weeks of treatment with vehicle (po, qd), 30 mg/kg Compound 1 (po, qd) or 100 mg/kg Compound 1 (po, qd). The protocols and procedures involving the care and use of animals were approved by the Institutional Animal Care and Use Committee (IACUC) of WuXiAppTec (Shanghai) Co., Ltd. (Shanghai, China).

Example 17—Compound 1 Dose-Dependently Reduces the Urine Protein Level in a Mouse Model of SLE Urine protein was individually evaluated in each mouse on a biweekly basis using Coomassie Brilliant Blue (CBB) assay with a urine protein test kit (Nanjing Jiancheng Biotechnology Institute, Jiangsu, China). As seen in FIG. 1, the urine protein level of mice from the vehicle group increased from 304.4±110.0 mg/L at week 8 to 1376.1±391.4 mg/L at week 18. Treatment with Compound 1 dose-dependently reduced the level of urine protein. 30 mg/kg Compound 1 significantly inhibited the increase of urine protein level ($p<0.05$, vs vehicle group), with 536.1±146.8 mg/L protein detected in the urine at the end of the study (week 18). Furthermore, 100 mg/kg Compound 1 maintained the urine protein level throughout the experiment (266.8±37.7 mg/L at week 18; $p<0.0001$, vs vehicle group). Overall, Compound 1 dose-dependently improved lupus nephritis in the spontaneous SLE model in mice.

Figure 2:
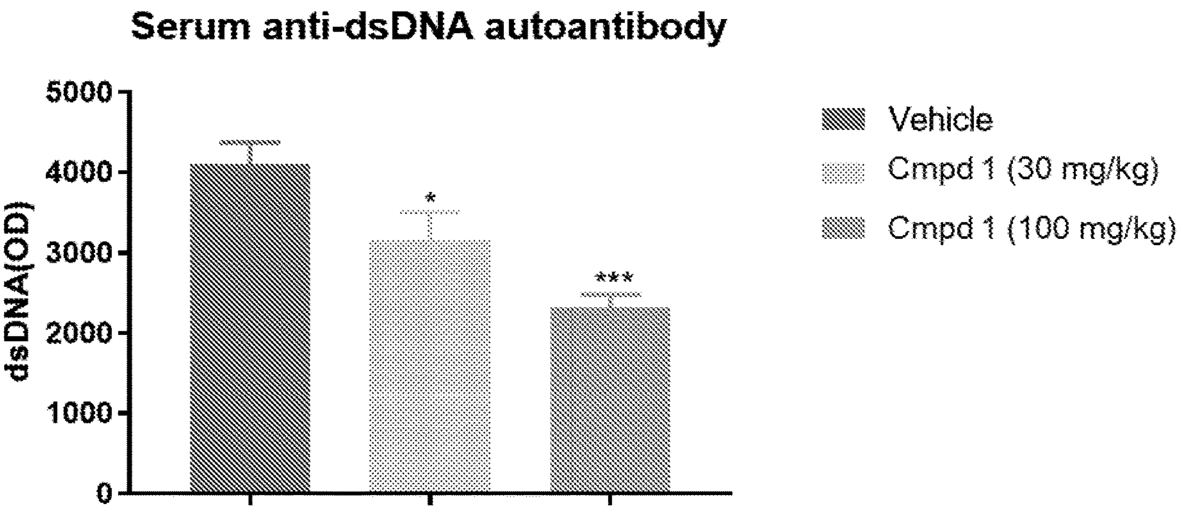
FIG. 2 is a bar chart showing the serum anti-dsDNA autoantibody level in MRL/lpr mice following treatment with vehicle or Compound 1.

Example 18—Compound 1 Dose-Dependently Reduces the Serum Anti-dsDNA Autoantibody Level in a Mouse Model of SLE Anti-dsDNA autoantibody levels were measured by ELISA. Briefly, a 96-well flat plate was coated with 10 μg/mL calf thymus ds-DNA (Sigma-Aldrich, MA, USA) at 4° C. overnight. After washing with PBS containing 0.05% Tween 20 (PBS-T) and blocking with 1% bovine serum albumin, serum samples (4000× dilution) were added and incubated for 1 h at room temperature. Goat anti-mouse IgG-HRP conjugate (Invitrogen, CA, USA) was then added for 1 h at room temperature, followed by washing with PBS-T three times. Lastly, ultra TMB-ELISA substrate solution (Pierce Biotechnology, IL, USA) was added and incubated for another 30 min, and the OD values at 405 nm were recorded after the reaction was stopped. As show in FIG. 2, at the end of the study, the level of serum anti-dsDNA autoantibody in the MRL/lpr mice were reduced to 76.8% ($p<0.05$, vs vehicle group) and 56.4% ($p<0.0001$, vs vehicle group) of the vehicle group after treatment with 30 mg/kg Compound 1 or 100 mg/kg Compound 1, respectively. The above results were in agreement with the therapeutic effect of Compound 1 in reducing urine protein.

Figure 3:
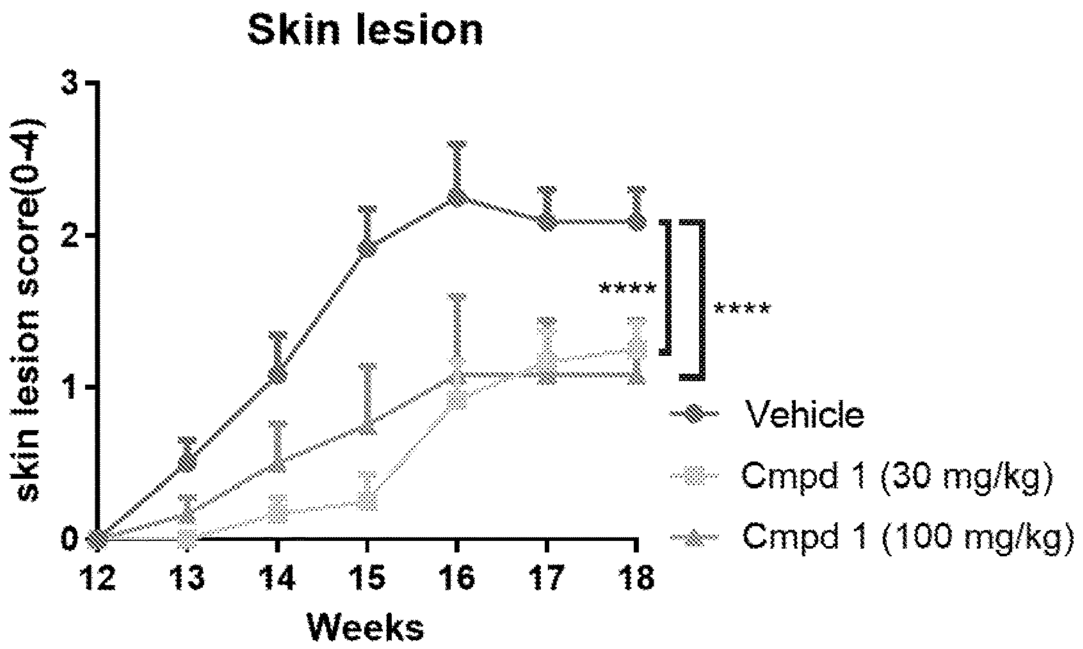
FIG. 3 is a line chart showing the skin lesion score over time in MRL/lpr mice following treatment with vehicle or Compound 1.

Example 19—Compound 1 Dose-Dependently Reduces Skin Lesion Severity in a Mouse Model of SLE Skin lesions were scored every week starting from week 12 and were expressed using a scoring system from 0 to 4 (0—normal; 1—small lesion with diameter between 2 to 4 mm; 2—lesion area <0.5 $cm^2$; 3—lesion area between 0.5 $cm^2$ to 1 $cm^2$; 4—lesion area >1 $cm^2$). As seen in FIG. 3, MRL/lpr mice developed skin lesions at week 13, and the pathologic score reached 2.1±0.2 at the end of the study (week 18). Treatment with Compound 1 at both 30 mg/kg and 100 mg/kg significantly reduced the skin lesion score at week 18 ($p<0.0001$, vs vehicle group).

Figure 4:
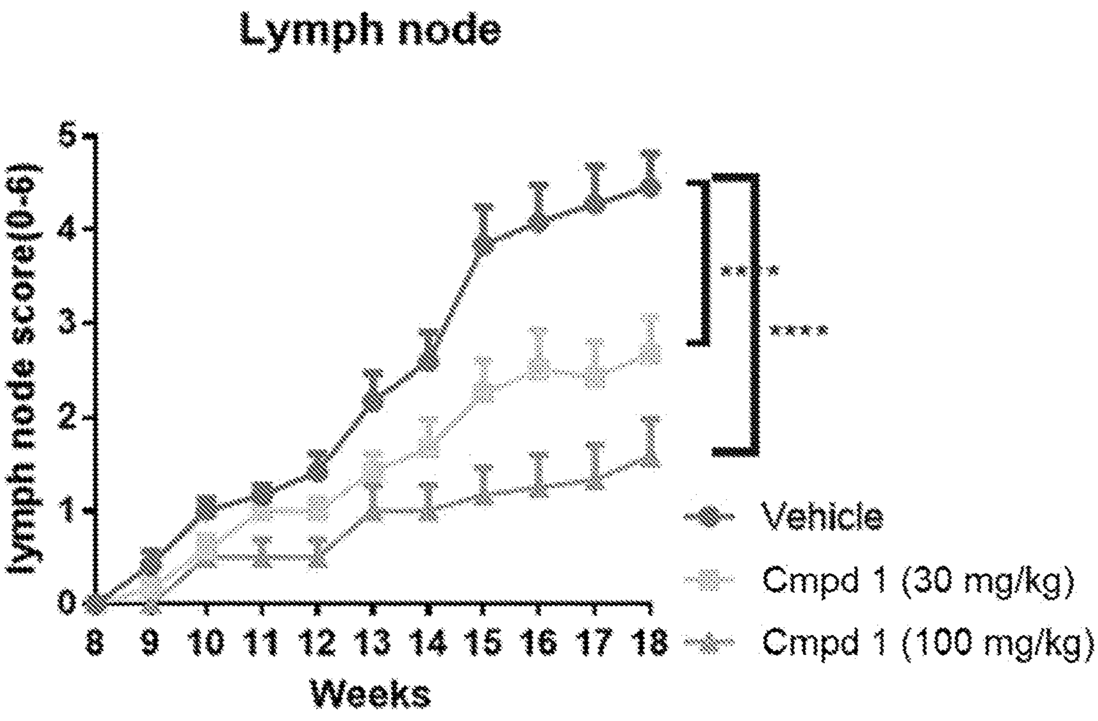
FIG. 4 is a line chart showing the lymph node score over time in MRL/lpr mice following treatment with vehicle or Compound 1.

Example 20—Compound 1 Dose-Dependently Reduces Lymphadenopathy in a Mouse Model of SLE Lymph nodes were scored weekly throughout the study, and were expressed using a scoring system from 0 to 6 based on the diameter of lymph nodes (0—normal; 1—<1 cm in one site; 2—<1 cm in two sites; 3—<1 cm in three sites; 4—>1 cm in one site and <1 cm in two sites); 5—>1 cm in two sites and <1 cm in one site; 6—>1 cm in three sites). As seen in FIG. 4, MRL/lpr mice developed lymphadenopathy at week 9, and the pathologic score reached 4.5±0.4 at the end of the study (week 18). The lymphadenopathy scores were reduced to 2.7±0.4 and 1.6±0.4 when the mice were treated with 30 mg/kg and 100 mg/kg Compound 1, respectively ($p<0.0001$, vs vehicle group).

Example 21—Compound 1 Dose-Dependently Improves the Pathological Scores of Lupus Nephritis in a Mouse Model of SLE At the end of the study, the spleen and lymph nodes were collected and weighed. Kidneys were fixed in formalin, embedded in paraffin, cut into sections of 5-μm thickness and stained with hematoxylin and eosin. The histopathological score was evaluated microscopically in a blinded manner, vide infra.

The histopathological score was evaluated microscopically in a blinded manner. The membranous glomerulonephritis score (GN score) was evaluated using scoring from 0 to 4 (0—normal; 1—mild, focal or early proliferation; 2—moderate or definite proliferation and increased matrix; 3—diffuse and focal or diffuse proliferation; 4—severe diffuse proliferation with crescent/sclerosis). The renal interstitial nephritis score (IN score) was graded from 0 to 4 for inflammation and necrosis (0—normal; 1—occasional, focal or small pockets of mononuclear cells (MNCs, 10-14 cells); 2—focal infiltration of MNCs (15-30 cells); 3—multifocal and extensive infiltration of MNCs; 4—severe infiltration of MNCs with extensive necrosis). Additionally, vasculitis was scored from 0 to 4 (0—normal; 1—occasional perivascular infiltration of MNCs; 2—several foci of perivascular infiltration of MNCs without necrosis; 3—multifocal perivascular infiltration of MNCs with/without necrosis; 4—multifocal or diffuse perivascular infiltration of MNCs, with extensive necrosis).

Figure 5:
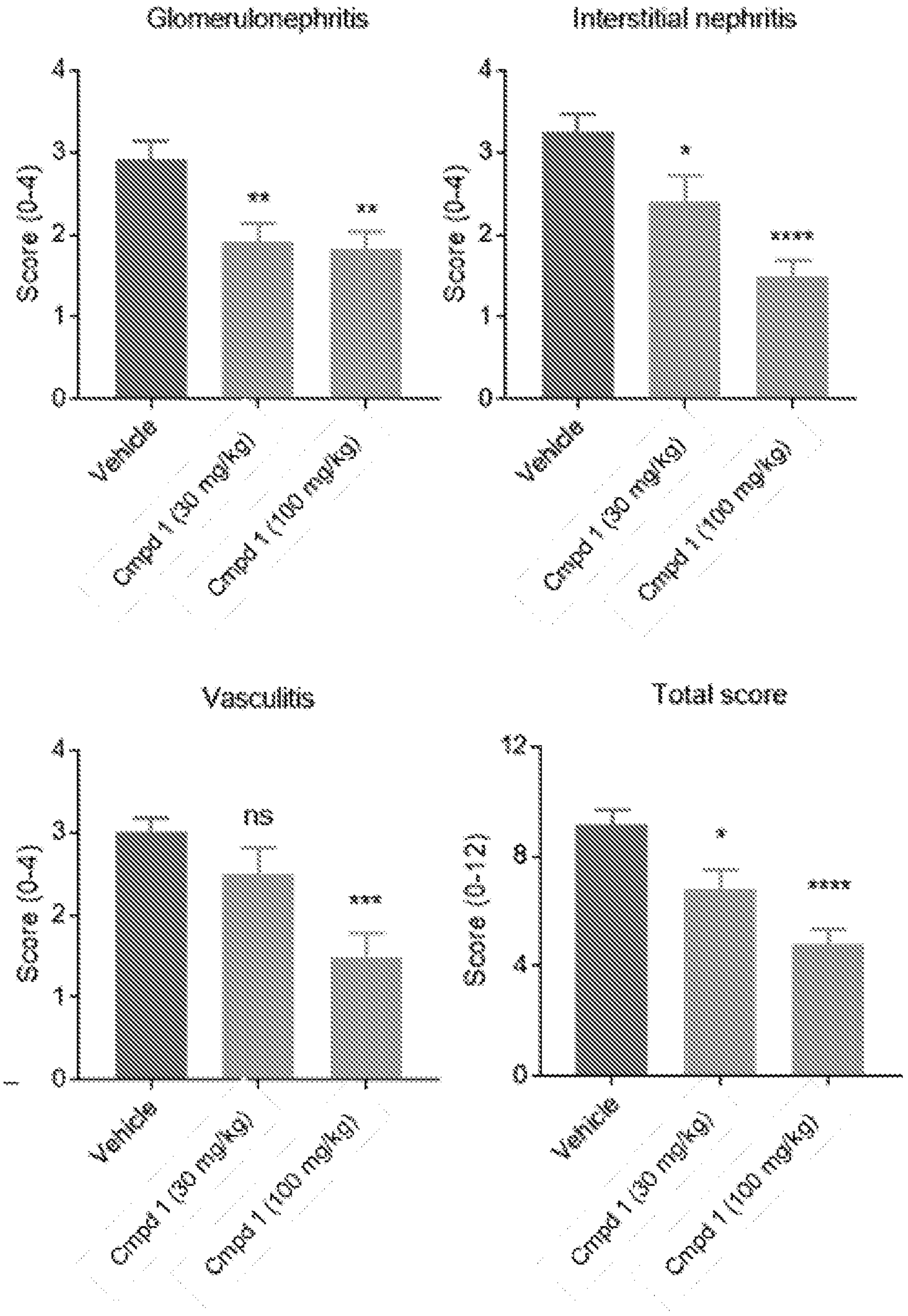
FIG. 5 is a series of bar charts showing the glomerulonephritis, interstitial nephritis, vasculitis, and total lupus nephritis pathology scores in MRL/lpr mice following treatment with vehicle or Compound 1.

As seen in FIG. 5, MRL/lpr mice in the vehicle group developed moderate-to-severe glomerulonephritis, interstitial nephritis and vasculitis at week 18, which was indicated by the pathological scores of around 3.0. Treatment with Compound 1 dose-dependently reduced the pathological score from all the three aspects. Of note, Statistical significance was achieved both in individual and total scores when the mice were treated with 100 mg/kg Compound 1.

Example 22—Compound 1 Significantly Reduces the Number of Lymphocytes in the PBMC, Spleen, and Kidneys in a Mouse Model of SLE The spleens and kidneys were harvested from the mice at the conclusion of the study (week 18) and digested into single-cell suspensions. Peripheral blood mononuclear cell (PBMC) were obtained after lysing red blood cells in the whole blood. Cells were stained with the following florescence-labelled antibodies: PerCP-Cyanine5.5-conjugated anti-mouse CD8a (BD Biosciences), AF700-conjugated anti-mouse CD3 (BD Biosciences), PE-eFluor610-conjugated anti-mouse B220 (BD Biosciences), e506-conjugated anti-mouse CD45 (BD Biosciences), BV605-conjugated anti-mouse CD138 (BioLegend), and BV711-conjugated anti-mouse CD4 (BioLegend).

Figure 6:
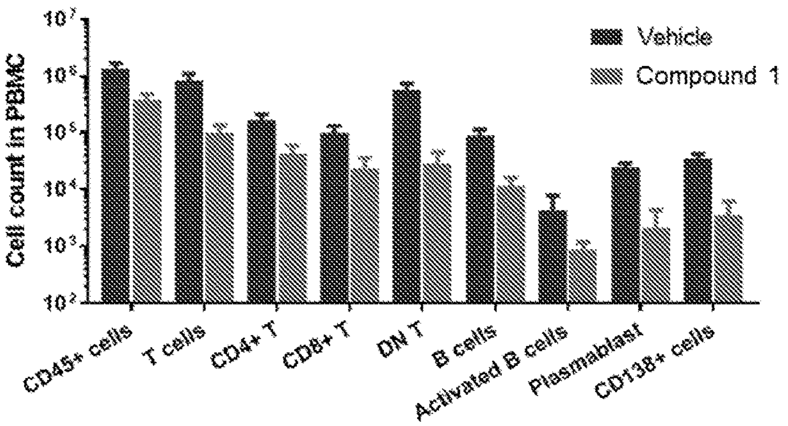
FIG. 6 is a bar chart showing the lymphocyte cell counts in a peripheral blood mononuclear cell (PBMC) panel taken from MRL/lpr mice following treatment with vehicle or Compound 1.
Figure 7:
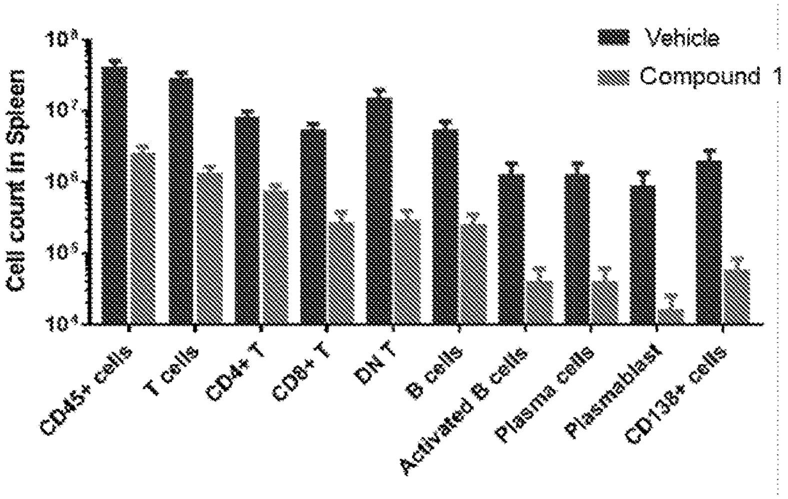
FIG. 7 is a bar chart showing the lymphocyte cell counts in the spleens of MRL/lpr mice following treatment with vehicle or Compound 1.

All cells were primarily gated on live lymphocytes based on forward scatter (FCS) and side scatter (SSC). Samples were analyzed on a flow cytometer (BD FACSCalibur, USA) to count the number of each subtype of lymphocytes. As seen in FIG. 6 and FIG. 7, after treatment with 100 mg/kg Compound 1, the number of total lymphocytes (CD45+), T cells (CD45+CD3+), CD4+ T cells (CD45+CD3+CD4+), CD8+ T cells (CD45+CD3+CD8+), double-negative T cells (CD45+CD3+CD4−CD8−), B cells (CD45+CD3−B220+), activated B cells (CD45+CD3−B220+CD69+), plasmablasts (CD45+CD3−B220+CD138+), plasma cells (CD45+CD3−B220−CD138+) and CD138+ cells (CD45+CD3−CD138+) were significantly reduced.

Figure 8:
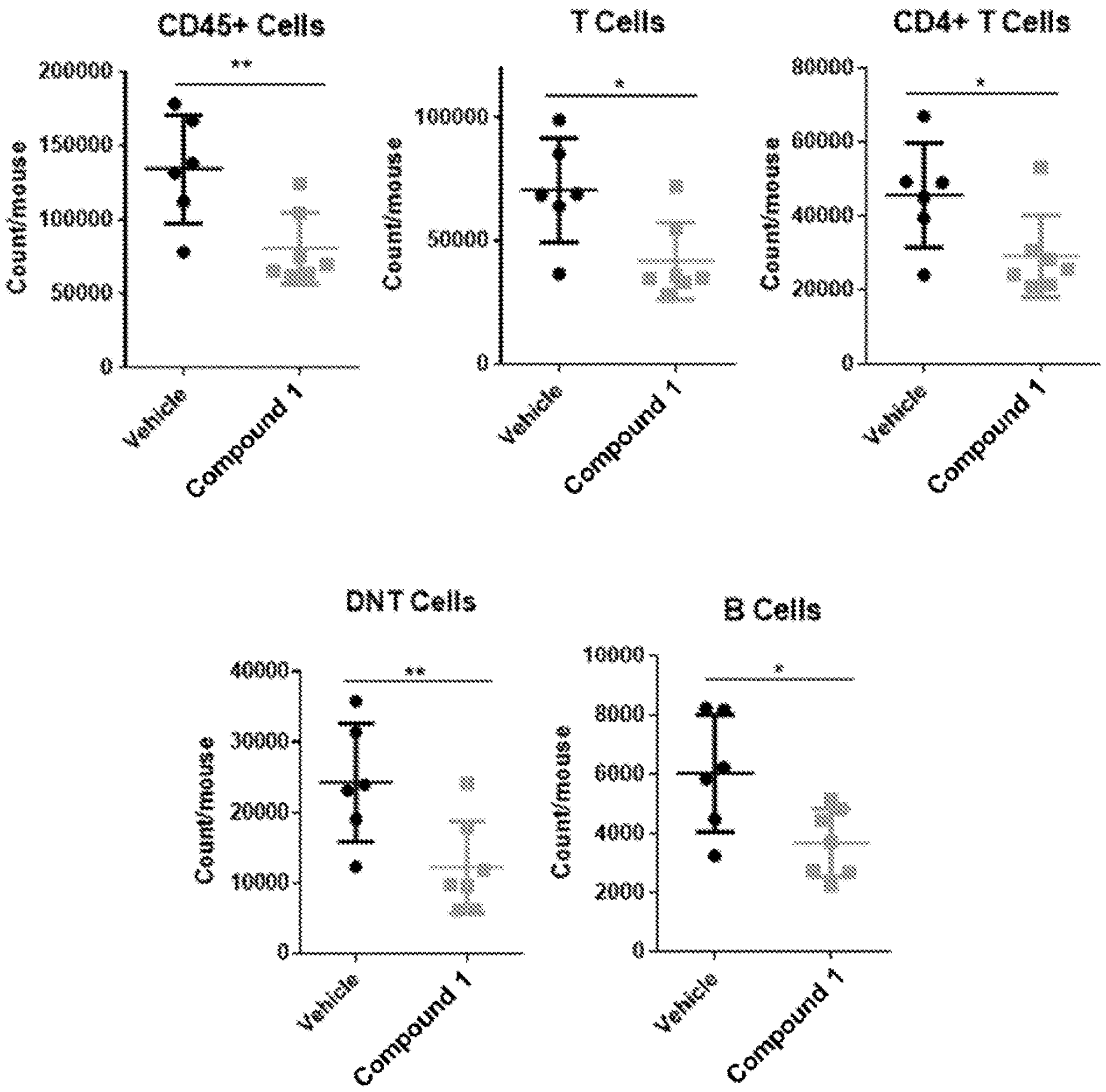
FIG. 8 is a series of plots showing the lymphocyte cell counts in the kidneys of MRL/lpr mice following treatment with vehicle or Compound 1.

Of note, the reduction of double negative T cells were most significant compared to other lymphocytes. Without being bound by theory, the reduced number of autoantibody-secreting plasmablast and plasma cells might be responsible for the reduced serum anti-dsDNA autoantibody results of Example 7 and the observed reduction of lupus nephritis severity. The number of lymphocytes infiltrating in the kidney are shown in FIG. 8. Treatment with 100 mg/kg Compound 1 significantly reduced the number of pro-inflammatory CD4+ T cells and double-negative T cells in the kidney. Without being bound by theory, the reduced infiltration by pro-inflammatory CD4+ cells and double-negative T cells may be responsible in part for the observed efficacy in treating lupus nephritis.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. Furthermore, the foregoing Description and Examples are exemplary of the present invention and not limiting thereof. The scope of the invention is therefore set out in the appended claims.

All patents and publications cited herein are fully incorporated by reference herein in their entirety.

What is claimed is:

1. A method of treating systemic lupus erythematosus in a patient comprising administering to the patient in need thereof a therapeutically effective amount of a compound of formula (II):

(II)

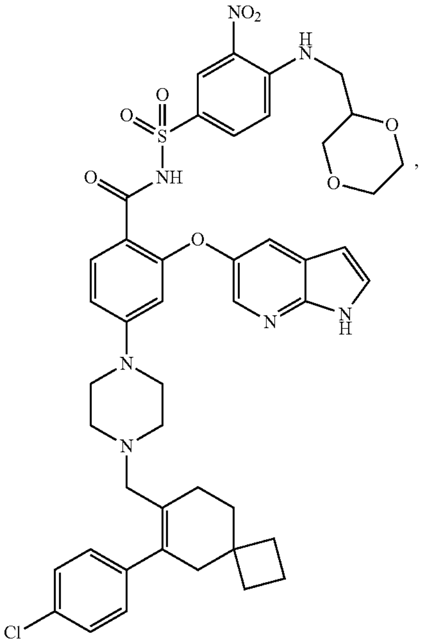

or a pharmaceutically acceptable salt, solvate, hydrate, stereoisomer, or tautomer thereof

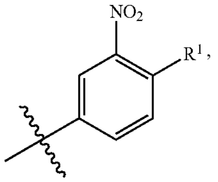

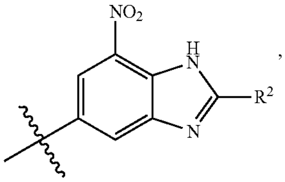

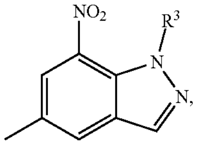

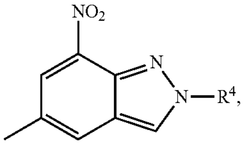

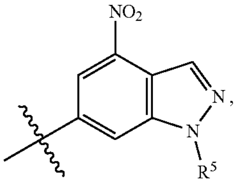

and

-continued

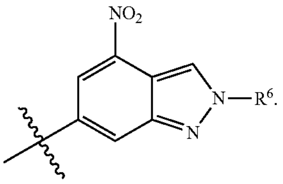

2. The method of claim 1, wherein the compound is selected from the group consisting of:

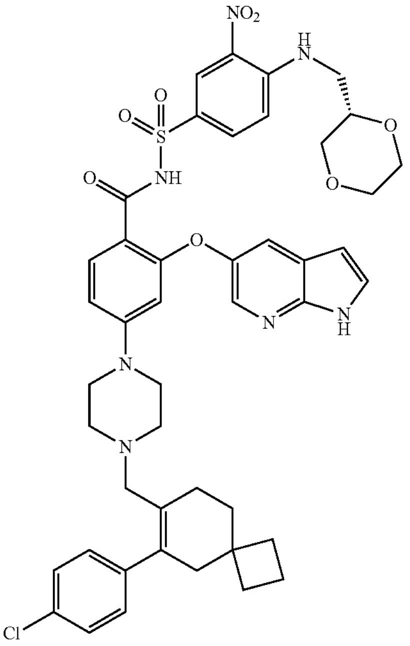

and

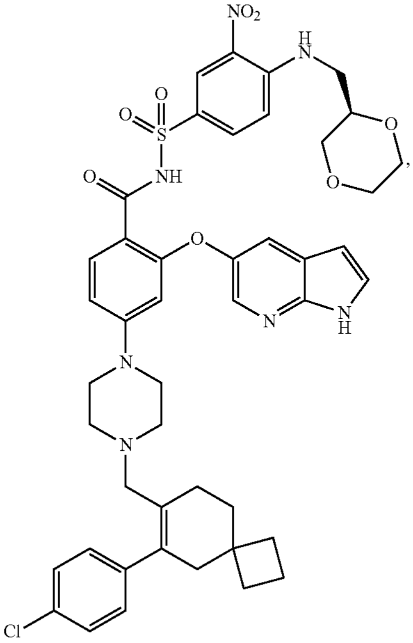

or a pharmaceutically acceptable salt, solvate, hydrate, or tautomer thereof.

3. The method of claim 2, wherein the compound is

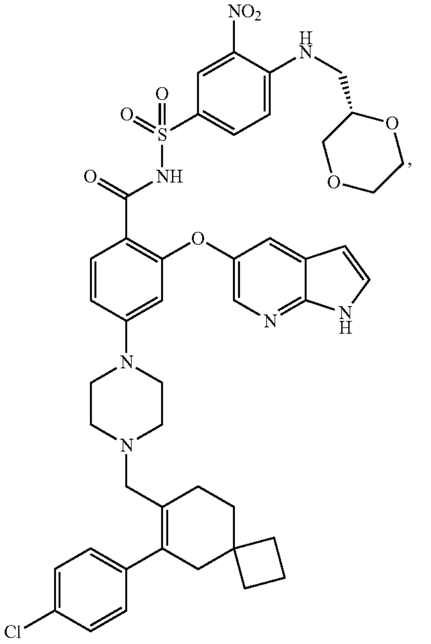 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, solvate, hydrate, or tautomer thereof.

4. The method of claim 2, wherein the compound is

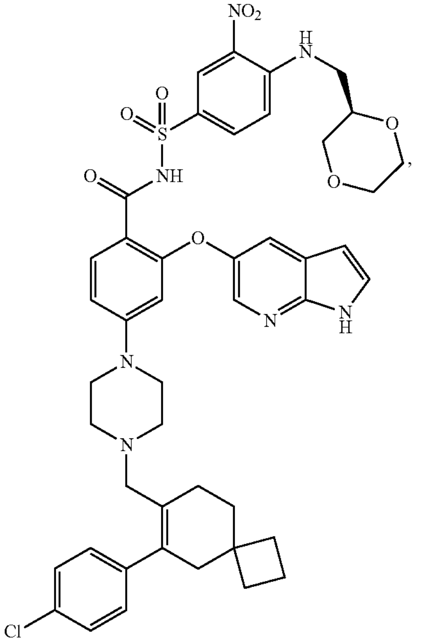 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, solvate, hydrate, or tautomer thereof.

5. The method of claim 1, wherein the compound of formula (II) or a pharmaceutically acceptable salt, solvate, hydrate, stereoisomer, or tautomer thereof is formulated in a form of a pharmaceutical composition.

6. The method of claim 1, wherein the patient is diagnosed as having lupus nephritis.

7. The method of claim 1, wherein the compound of formula (II) or a pharmaceutically acceptable salt, solvate, hydrate, stereoisomer, or tautomer thereof is administered to the patient in need thereof at a dose sufficient to elicit one or more effects selected from the group consisting of: reduced excretion of protein in the urine of the patient, reduced serum anti-dsDNA autoantibody levels in the patient, reduced skin lesion severity in the patient, reduced lymphadenopathy severity in the patient, reduced glomerulonephritis severity in the patient, reduced interstitial nephritis severity in the patient, reduced vasculitis severity in the patient, reduced lymphocyte cell counts in a peripheral blood mononuclear cell (PBMC) panel taken from the patient, reduced lymphocyte cell counts in the spleen of the patient, and reduced lymphocyte infiltration of the kidneys of the patient.

8. The method of claim 7, wherein the method reduces excretion of protein in the urine of the patient.

9. The method of claim 7, wherein the method reduces serum anti-dsDNA autoantibody levels in the patient.

10. The method of claim 7, wherein the method reduces skin lesion severity in the patient.

11. The method of claim 7, wherein the method reduces lymphadenopathy severity in the patient.

12. The method of claim 7, wherein the method reduces glomerulonephritis severity in the patient.

13. The method of claim 7, wherein the method reduces interstitial nephritis severity in the patient.

14. The method of claim 7, wherein the method reduces vasculitis severity in the patient.

15. The method of claim 7, wherein the method reduces lymphocyte cell counts in a peripheral blood mononuclear cell (PBMC) panel taken from the patient.

16. The method of claim 7, wherein the method reduces lymphocyte cell counts in the spleen of the patient.

17. The method of claim 7, wherein the method reduces lymphocyte infiltration in the kidneys of the patient.

* * * * *